(12) United States Patent
Yao et al.

(10) Patent No.: US 8,557,837 B2
(45) Date of Patent: Oct. 15, 2013

(54) SINOMENINE DERIVATIVES, SYNTHETIC METHODS AND USES THEREOF

(75) Inventors: Zhujun Yao, Shanghai (CN); Bing Sun, Shanghai (CN); Yangtong Lou, Shanghai (CN); Zhenyu Yang, Shanghai (CN); Aizhong Chen, Shanghai (CN); Zhao Ma, Shanghai (CN)

(73) Assignees: Shanghai Institute of Organic Chemistry, Chinese Academy of Sciences, Shanghai (CN); Shanghai Institutes for Biological Sciences, Chinese Academy of Sciences, Shanghai (CN)

( * ) Notice: Subject to any disclaimer, the term of this patent is extended or adjusted under 35 U.S.C. 154(b) by 0 days.

(21) Appl. No.: 13/578,499

(22) PCT Filed: Feb. 9, 2011

(86) PCT No.: PCT/CN2011/070893
§ 371 (c)(1),
(2), (4) Date: Aug. 10, 2012

(87) PCT Pub. No.: WO2011/098035
PCT Pub. Date: Aug. 18, 2011

(65) Prior Publication Data
US 2012/0308589 A1 Dec. 6, 2012

(30) Foreign Application Priority Data
Feb. 10, 2010 (CN) .......................... 2010 1 0108675

(51) Int. Cl.
*A61K 31/439* (2006.01)
*C07D 221/22* (2006.01)

(52) U.S. Cl.
USPC ............................................ 514/289; 546/74

(58) Field of Classification Search
USPC ........................................... 514/289; 546/74
See application file for complete search history.

(56) References Cited

FOREIGN PATENT DOCUMENTS

CN            101265266     *    9/2008     .................... 514/289

* cited by examiner

*Primary Examiner* — Samantha Shterengarts
(74) *Attorney, Agent, or Firm* — Osha Liang LLP

(57) ABSTRACT

The invention relates to sinomenine derivatives, methods for their synthesis and their applications. The sinomenine derivatives include oxidation derivatives, and C-10 substituted sinomenine derivatives. Based on the readily oxidizable phenol group on sinomenine structure, using oxidation, oxidative dearomatization, or conjugated addition aromatization, one can introduce C-10 substitutions to synthesize the sinomenine derivatives. The sinomenine derivatives of the invention have the following structures:

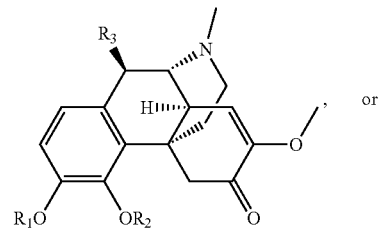

or
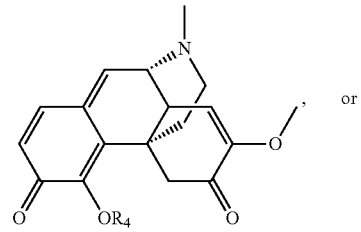
or

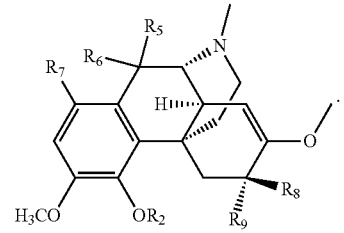

Using in vitro TNF-α inhibition assay, the activities of the synthetic compounds are assessed. Results from these assays shown that most compounds have anti-inflammatory effects, and some compounds have better activities than that of sinomenine. These compounds may be used in treating immune diseases such as rheumatoid arthritis (RA).

16 Claims, 3 Drawing Sheets

SINOMENINE DERIVATIVES, SYNTHETIC METHODS AND USES THEREOF

CROSS REFERENCE TO RELATED APPLICATIONS

This is a national stage application of PCT/CN2011/070893, filed on Feb. 9, 2011, which claims priority of Chinese Patent Application No. 201010108675.X, filed on Feb. 10, 2010. This application claims the priorities and benefits of these prior applications and incorporates their disclosures by reference in their entirety.

FIELD OF THE INVENTION

The present invention relates to sinomenine derivatives, synthetic methods and uses of these derivatives. The derivatives include oxidized sinomenine derivatives and sinomenine with C-10 substitutions. Sinomenine derivatives can be obtained from sinomenine or its analogs by oxidation (oxidative transformation), oxidative dearomatization, conjugated addition rearomatize to introduce substitutions at C-10. The present invention also relates to properties and uses of these sinomenine derivatives as TNF-α inhibitors in the treatment or prevention of immune diseases and diseases associated with abonormal TNF-α in mammals.

BACKGROUND ART

*Sinomenium acutum* is a common Chinese medicinal plant. The name "*Sinomenium acutum*" first appeared in the Song Dynasty. It is recorded in detail in "Atalas of Matria Medica" and "Catalogs of Materia Medica." It has anti-rheumatioid and analgesic properties. It has been used in the treatment of rheumatoid arthritis (RA), pain and numbness in extremities, injuries and inflammation. It is mostly distributed in Shanxi, Henan, Hubei, Jiangsu, Anhui, Zhejiang, Jiangxi, and Fujian provinces in China. The stem and roots of *Sinomenium acutum* contain sinomenine, sinoacutine, disinomenine, ethylsinomenine, isosinomenine, sinactine, acutumine, acutumidine, tuduranine, and magnoflorine. It also contains small amounts of stepherine, mechelalbine, dl-syngaresinol, β-sitosterol, and stigmasterol.

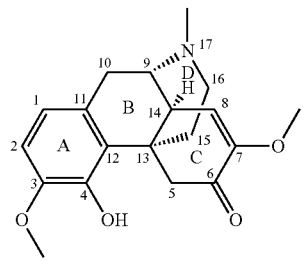

Sinomenine 1

Sinomenine, 1, is an isoquinoline alkaloid isolated from *Sinomenium acutum*. Its chemical name is (9a,13a,14a)-7,8-didehydro-4-hydroxy-3,7-dimethoxy-17-methyl-morphonan-6-one. Its molecular formula is $C_{19}H_{23}NO_4$, and its molecular weight is 329.38, and its optical rotation is $[\alpha]_{20}^{D}=-71°$, (c=2.1, ethanol). The structure of sinomenine is similar to that of morphinoids and is composed of a hydrophenanthrene nucleus with a ethylamine bridge, containing four rings and three optical active centers. Its structure and compound number are as shown in the above figure.

Sinomenine has anti-inflamatory, immune suppression, analgesic, anti-hypertension, anti-irrythmia pharmacological activities. It is used in the clinics to treat rheumatoid arthritis and irrythmia. Treatment of rheumatoid arthritis is the best defined clinical use of sinomenine. Currently, the dosages used in the clicnic include Zhenqingfeng pain relief tablets, sinomenine slow release tablets, sinomenine HCl injection, and sinmenine tablets. The main route of administration is oral administration, intramuscular injection, injection at the acupuncture points, and iontophoresis. Rheumatoid arthritis is an autoimmune disease characterized with inflammation at synovial joint. Repeated occurrence of synovial joint inflammation can lead to damages of cartilage and bone in the joint, impairment of joint function, and even disability. Rheumatoid arthritis still has no effective treatment; most treatments still remain at controlling the inflammation and the after-effects. At the moment, medications used in the treatment of rheumatoid arthritis are mainly non-steroidal anti-inflamatory drugs (NSAID), as represented by Aspirin, corticoid steroid drugs, disease modulator such as gold containing preparations (Auranofin), penicillamine, chloroquine, levamisole, immune suppresors (such as Methotrexate (MTX)), Chinese medicine Tripterygium Wilfordii, yunnan begonia, and sinomenine Relative to other medications, sinomenine has a unique structure. As compared with the well studied NSAID, research of sinomenine is very preliminary. Therefore, it is uniquely valuable to study the properties of sinomenine.

Sinomenine when used as a single agent in the clinic has the following drawbacks: the in vivo half life of sinomenine is relatively short and large doses are needed. In addition, it is typically taken orally for a long time. Sinomenine has a strong histaminic effect. In clinical use, it often causes skin rash, and it is often accompanied with gastric intestinal irritation side effects. Furthermore, sinomenine is unstable to light and heat; it is susceptible to degradation.

Therefore, there have been a wide range of research and reports on the dosage of sinomenine with respect to how to enhance its therapeutic effects, lower its toxic side effects, and change its irritative properties and instability. By using a proper dosage form, such as new dosage forms of slow release, controlled release, gels, and sprays, the clinical therapeutic effects of sinomenine to some extent are indeed improved and the adverse reaction is reduced, resulting in certain outcome. However, it is difficult to completely alleviate the above noted drawbacks of sinomenine simply by changing the dosage forms. To achieve that goal, it is necessary to modify the structure of sinomenine, to embark on medicinal chemistry research and improvement, in order to achieve new sinomenine derivative with high potencies and low toxicities.

To date, many research institutions in China have initiated research projects on sinomenine. This provides a unique Chinese perspective on sinomenine. Xianrong Ye (Pharmaceutical Report, 2004, 39(3), 180-183) reported structure modifications of sinomenine C. The research group of Guowei Qin at Shanghai Institute of Materia Medica has used sinomenne as a lead compound to develop memory enhancing drugs (WO 2004/0483401 A1). The research group of Yi Pan at Nanjing University (CN 1785976A, CN 1786977A, CN 1821244A), the research group of Jianxin Lee at Nanjing University (CN 101265266A, CN 101148437A), Hunan Zhenqing Pharmaceutical Group, Ltd. Co. (CN 1876634A), Xichuan University (CN 1800164A, CN 1948291A), our research group (CN 1687065A, CN 1687070A), and WO 2007/07070 all have studied structure modifications of sinomenine chemicals with respect to their anti-inflamatory and anti-immune activities.

The chemical structure of sinomenine contains a phenol group, which is easily oxidized in the presence of an oxidant. Therefore, we studied the reactivity of sinomenine under oxidative conditions and obtained a series of derivatives with novel structures. Furthermore, using TNF-α inhibition experiments, we have assessed the activities of these new derivatives.

The cellular origins of TNF-α covers a wide range, including various immune cells, endothelial cells, fibroblasts, epithelial cells, keratinocytes, smooth muscle cells, asterocytes, osteoblasts, etc. The macrophages in heart tissue are good sources for the inflamatory cytokine, TNF-α. Human TNF-α gene encodes a propeptide; its signal peptide sequence anchors the propeptide to the cell membrane, resulting in an active transmembrane interferon. After cleavage of the signal peptide by an enzyme, it produces a secretory TNF-α, with a molecular weight of 17 kD. NF-κB and p38-MAPK signal pathways participate in the expression of TNF-α. TNF-α has a wide range of biological activities, such as involvement in inflamation reaction and immune response, antitumor, involvement in the endotoxic shock pathological processes, leading to cachexia. TNF-α has dual functions: on the one hand, it plays an important role in organism immune regulation, physiological function, and counter infections. On the other hand, if TNF-α is continuously produced or over-produced, it will lead to fever, shock, and cachexia. At the same time, TNF-α can further induce IL-6, IL-8, and IL-10 cytokine productions. These inflamatory cytokines are involved in accute response and fever responses, which result in the release of chemotatic peptides, and activation of endothelial cells, which results in the increased permeability of the blood vessels.

The functions of TNF-α in rheumatoid arthritis: TNF-α is a pro-inflamatory cytokine that plays a central role in the mechanism underlying the development of rheumatoid arthritis; it is involved in the initiation and development of rheumatoid arthritis. TNF-α is mainly produced by macrophages. It can induced the production of other inflammation factors such as interleukin-1 (IL-1) and interleukin-6 (IL-6). It can activate adhesion molecules, enhance the production of metallo proteases, inhibit the synthesis of cartilage proteoglycans, leading to bone and cartilage damages. Currently, clinical treatments of autoimmune rheumatoid arthritis mainly use anti-TNF-α antibodies and soluble TNF-α receptor fusion proteins. Good treatment results have been obtained. Using in vitro assays to assess the inhibition of TNF-α by chemical compounds, one can effectively evaluate the anti-inflamatory and immune suppression activities of the compounds.

SUMMARY OF INVENTION

The first object of this invention is to provide several products obtained from oxidation of sinomenines and derivatives based on these oxidative products. The second object of this invention is to provide methods for the preparation of the above derivatives. The third object of this invention is to provide uses of the above sinomenine derivatives as inhibitors of TNF-α in the treatment and prevention of immune diseases and diseases associated with abnormal TNF-α activities in mammals. The fourth object of the invention is to provide a method for treating immune diseases and diseases associated with abnormal TNF-α activities in a subject, the method comprises administering a sinomenine derivative of the invention to a subject in need of such a treatment.

In the first aspect, the invention provides a sinomenine derivative or its isomer or a pharmaceutically acceptable salt, ester or solvate thereof. The sinomenine derivative has the following structure:

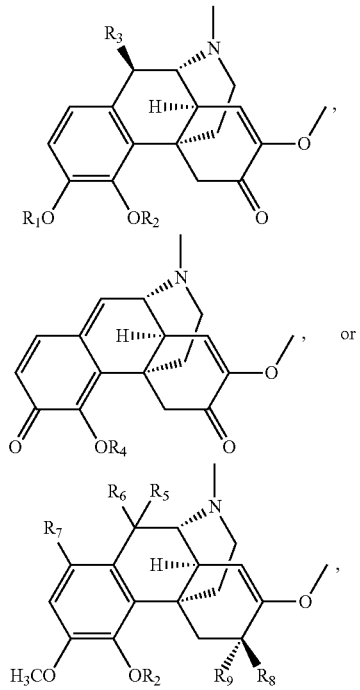

wherein $R_1$=H or $R_{10}CO$; $R_2$=H or $R_{10}CO$; $R_3$=$R_{11}O$, $R_{12}S$, $R_{13}R_{14}N$, OH, $R_{10}COO$ or

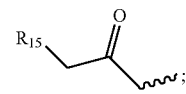

$R_4$=H or $R_{16}R_{17}R_{18}Si$; $R_5$=$R_{11}O$, OH or $CH_3COO$; $R_6$=H or $R_{11}O$; or $R_5$, $R_6$ together form an oxo group (=O); $R_7$=H, halogen or hydroxymethyl; $R_8$=—OH or H; $R_9$=—OH or H; or $R_8$, $R_9$ together form an oxo group (=O); $R_{10}$=$C_{1\sim10}$ hydrocarbyl (i.e., hydrocarbon group, including alkyl, alkenyl, and alkynyl) (preferably, $C_{1\sim6}$ hydrocarbyl, more preferably, $C_{1\sim4}$ hydrocarbyl, more preferably $C_{1\sim6}$ alkyl, more preferably $C_{1\sim4}$ alkyl); $R_{11}$=$C_{1\sim10}$ hydrocarbyl; $R_{12}$=$C_{1\sim10}$ hydrocarbyl, a 5-membered or 6-membered aromatic ring optionally containing 1-3 substituents or unsubstituted, a 5-membered or 6-membered nitrogen-containing heterocycle optionally containing 1-3 substituents or unsubstituted, a 5-membered or 6-membered oxygen-containing heterocycle optionally containing 1-3 substituents or unsubstituted, a 5-membered or 6-membered sulfur-containing heterocycle optionally containing 1-3 substituents or unsubstituted, wherein the substituent is $C_{1\sim10}$ hydrocarbyl, halogen, $C_{1\sim4}$ alkyl, $C_{1\sim4}$ fluoroalkyl, —$NO_2$, —CN, —$OCH_3$ or —OH; $R_{13}$=$C_{1\sim10}$ alkyl, a 5-membered or 6-membered aromatic ring optionally containing 1-3 substituents or unsubstituted, a 5-membered or 6-membered nitrogen-containing heterocycle optionally containing 1-3 substituents or unsubstituted, a 5-membered or 6-membered oxygen-containing heterocycle optionally containing 1-3 substituents or unsubstituted, a 5-membered or 6-membered sulfur-containing heterocycle optionally containing 1-3 substituents or unsubstituted, wherein the substituent is $C_{1-10}$ hydrocarbyl, halogen, $C_{1-4}$ alkyl, $C_{1-4}$ fluoroalkyl, —$NO_2$, —CN, $C_{1-4}$ alkoxy or —OH; $R_{14}$=H or $C_{1-10}$ hydrocarbyl; or $R_{13}$ and $R_{14}$ together with the nitrogen atom, to which they are attached, form a 5-membered or 6-membered nitrogen-containing heterocycle optionally containing 1-3 substituents or unsubstituted, wherein the substituent is halogen, $C_{1-4}$ alkyl, $C_{1-4}$ fluoroalkyl, —$NO_2$, —CN, $C_{1-4}$ alkoxy or —OH; $R_{15}$=H or $C_{1-10}$ alkyl; $R_{16}$=$C_{1-10}$ hydrocarbyl or phenyl; $R_{17}$=$C_{1-10}$ hydrocarbyl or phenyl; $R_{18}$=$C_{1-10}$ hydrocarbyl or phenyl.

Preferably, the 5-membered or 6-membered aromatic ring is cyclopentene or phenyl; the 5-membered or 6-membered nitrogen-containing heterocyclic ring is pyrrole, imidazole, pyrazole, or pyridine; the 5-membered or 6-membered oxygen-containing heterocyclic ring is furan or pyran; the 5-membered or 6-membered sulfur-containing heterocyclic ring is thiophen.

Preferably, $R_1$=H or $R_{10}CO$; $R_2$=H or $R_{10}CO$; $R_3$=$R_{11}O$, $R_{12}S$, $R_{13}R_{14}N$, OH, $R_{10}COO$ or

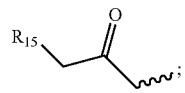

$R_4$=H or $R_{16}R_{17}R_{18}Si$; $R_5$=$R_{11}O$, OH or $CH_3COO$; $R_6$=H or $R_{11}O$; or $R_5$, $R_6$ together form an oxo group (=O); $R_7$=H, halogen or methoxy; $R_8$=—OH or H; $R_9$=—OH or H; or $R_8$, $R_9$ together form an oxo group (=O); $R_{10}$=$C_{1-6}$ alkyl; $R_{11}$=$C_{1-6}$ alkyl; $R_{12}$=$C_{1-6}$ alkyl, a phenyl optionally containing 1-3 substituents, an imidazole optionally containing 1-3 substituents, a furna or pyran optionally containing 1-3 substituents, a thiophen optionally containing 1-3 substituents, wherein the substitutent is halogen, $C_{1-4}$ alkyl, $C_{1-4}$ fluoroalkyl, —$NO_2$, —CN, $C_{1-4}$ alkyl or —OH; $R_{13}$=$C_{1-6}$ alkyl, a phenyl optionally containing 1-3 substituents, an imidazole optionally containing 1-3 substituents, a furna or pyran optionally containing 1-3 substituents, a thiophen optionally containing 1-3 substituents, wherein the substitutent is halogen, $C_{1-4}$ alkyl, $C_{1-4}$ fluoroalkyl, —$NO_2$, —CN, $C_{1-6}$ alkyl or —OH; $R_{14}$=H or $C_{1-6}$ alkyl; or $R_{13}$≠$R_{14}$ together with the nitrogen atome to which they are attached form an imidazole optionally containing 1-3 substituents, wherein the substitutent is halogen, $C_{1-4}$ alkyl, $C_{1-4}$ fluoroalkyl, —$NO_2$, —CN, $C_{1-4}$ alkoxy or —OH; $R_{15}$=H or $C_{1-6}$ alkyl; $R_{16}$=$C_{1-6}$ alkyl or phenyl; $R_{17}$=$C_{1-6}$ alkyl or phenyl; $R_{18}$=$C_{1-6}$ alkyl or phenyl.

More preferably, $R_1$=H or $R_{10}CO$; $R_2$=H or $R_{10}CO$; $R_3$=$R_{11}O$, $R_{12}S$, $R_{13}R_{14}N$, OH, $R_{10}COO$ or

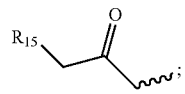

$R_4$=H or $R_{16}R_{17}R_{18}Si$; $R_5$=$R_{11}O$, OH or $CH_3COO$; $R_6$=H or $R_{11}O$; or $R_5$, $R_6$ together form an oxo group (=O); $R_7$=H, halogen or methoxy; $R_8$=—OH or H; $R_9$=—OH or H; or $R_8$, $R_9$ together form an oxo group (=O); $R_{10}$=$C_{1-4}$ alkyl; $R_{11}$=$C_{1-4}$ alkyl; $R_{12}$=$C_{1-4}$ alkyl, a phenyl optionally containing 1-3 substitutents, wherein the substitutent is halogen, $C_{1-4}$ alkyl, $C_{1-4}$ fluoroalkyl, —$NO_2$, —CN, $C_{1-4}$ alkoxy or —OH; $R_{13}$=$C_{1-4}$ alkyl, a phenyl optionally containing 1-3 substitutents, wherein the substitutent is halogen, $C_{1-4}$ alkyl, $C_{1-4}$ fluoroalkyl, —$NO_2$, —CN, $C_{1-4}$ alkoxy or —OH; $R_{14}$=H or $C_{1-6}$alkyl; or $R_{13}$ and $R_{14}$ together with the nitrogen atom to which they are attached form an imidazole optionally containing 1-3 substituents, wherein the substitutent is halogen, $C_{1-4}$ alkyl, $C_{1-4}$ fluoroalkyl, —$NO_2$, —CN, $C_{1-4}$ alkoxy or —OH; $R_{15}$=H or $C_{1-4}$ alkyl; $R_{16}$=$C_{1-4}$ alkyl; $R_{17}$=$C_{1-4}$ alkyl; $R_{18}$=$C_{1-4}$ alkyl.

The preferred sinomenine derivative has the following structure:

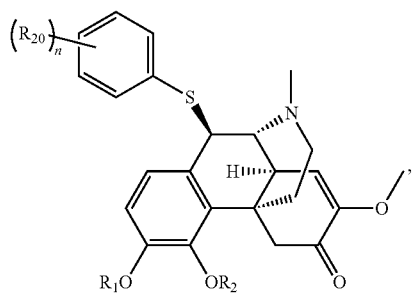

wherein $R^1$=H or $R_{10}CO$; $R_2$=H or $R_{10}CO$, wherein $R_{10}$ is $C_{1-6}$alkyl, preferably $C_{1-4}$ alkyl, $R_{20}$ represents H or a substituent selected from the following: halogen, $C_{1-4}$ alkyl, $C_{1-4}$ fluoroalkyl, —$NO_2$, —CN, $C_{1-4}$ alkoxy, or —OH; n=1, 2, or 3.

Further preferred sinomenine derivatives have the following structures:

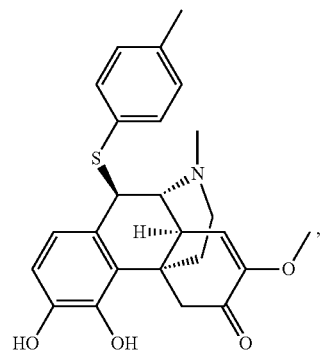

1

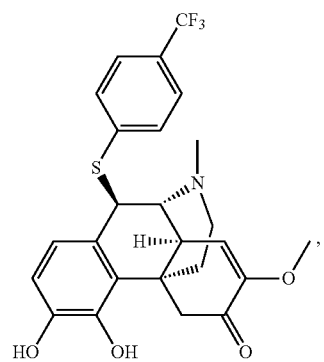

2

3
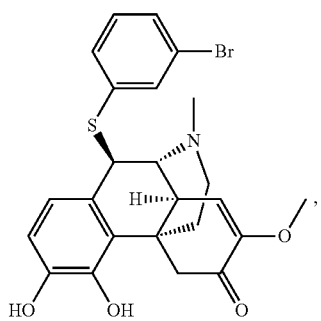
4
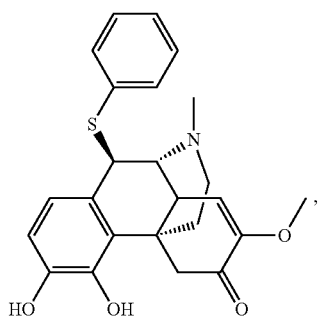
5
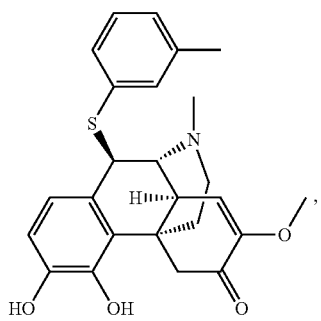
6
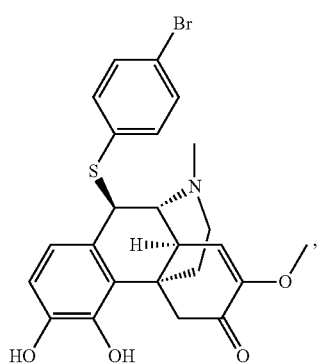
7
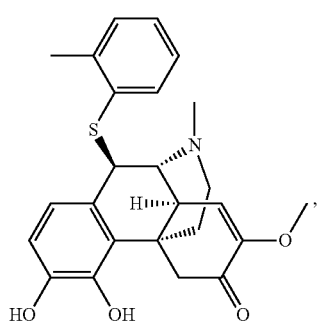
8
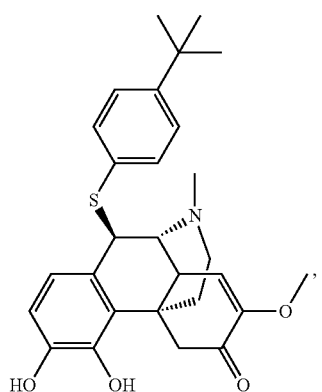
9
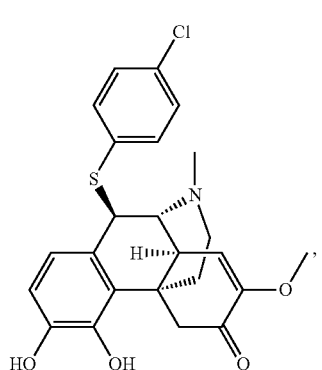
10
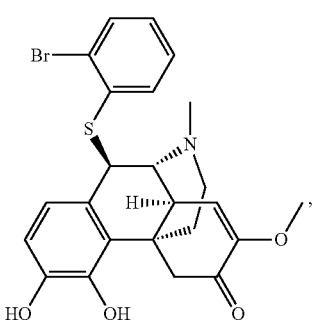
11
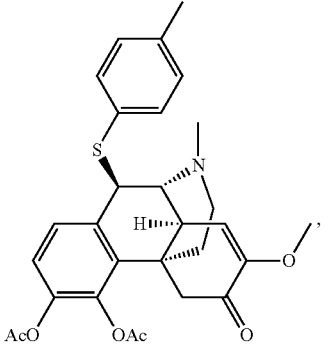

12
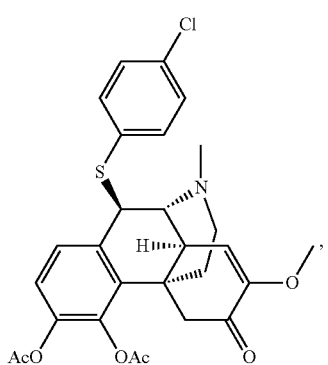
13
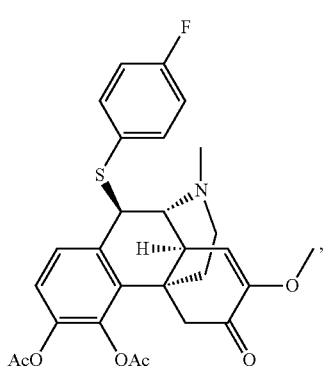
14
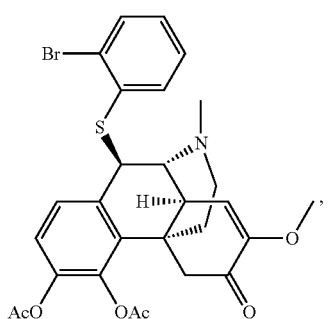
15
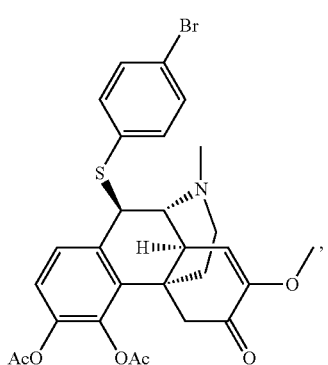
16
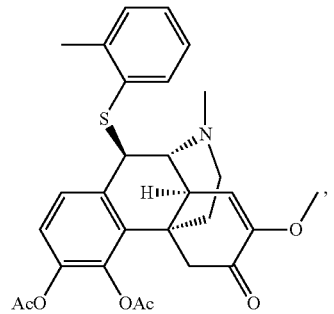
17
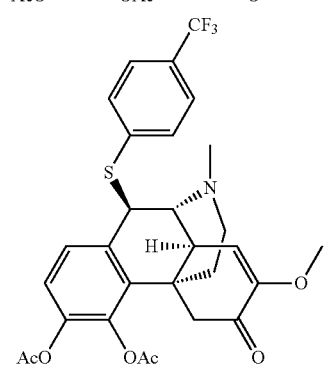
18
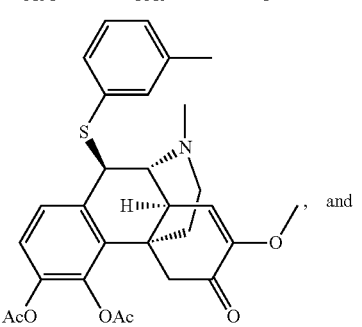
, and
19
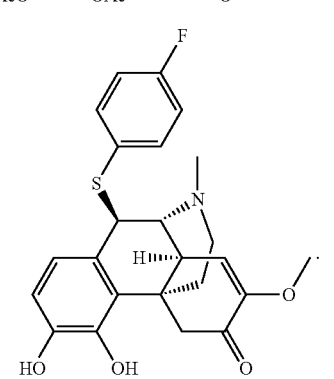
.
Sinomenine derivatives of the invention may also include the following compounds:
20
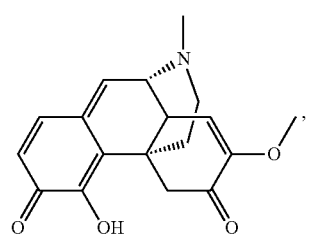

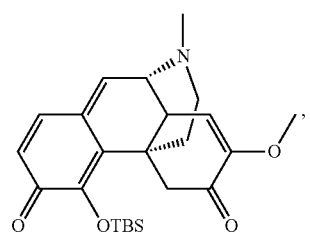
21
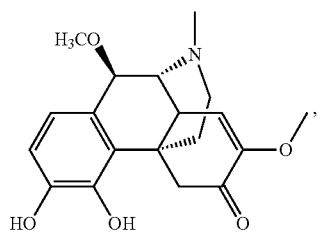
22
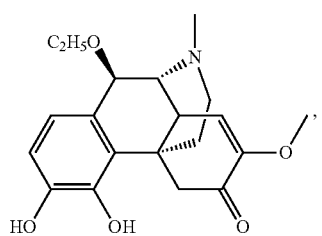
23
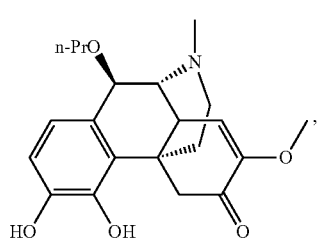
24
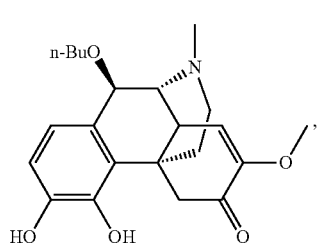
25
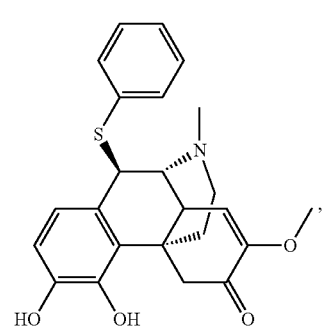
4
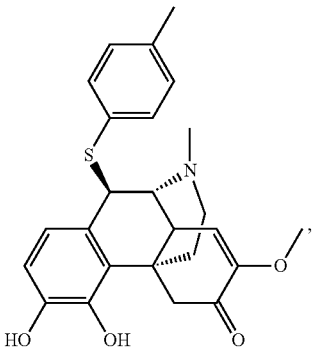
1
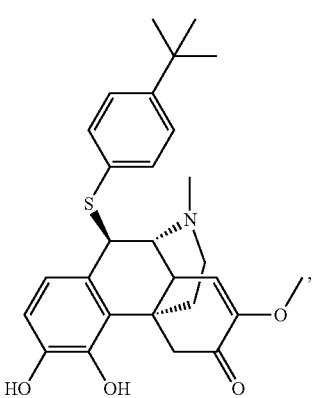
8
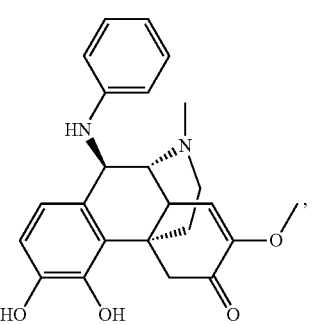
26
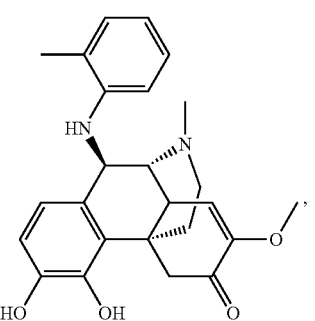
27

28
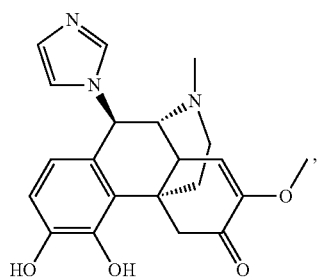
29
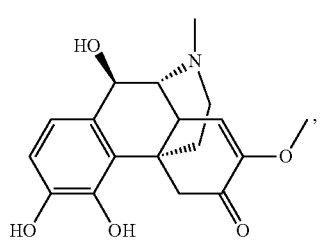
30
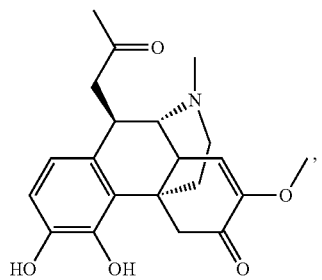
31
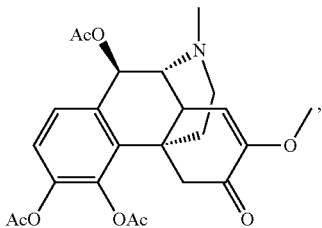
32
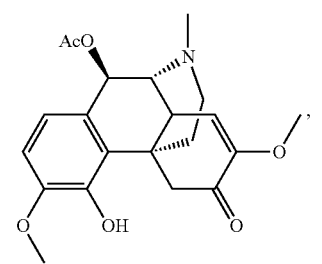
33
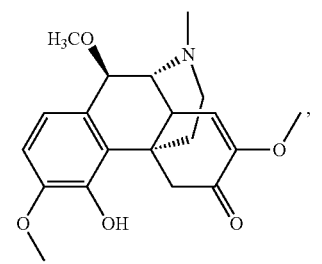
34
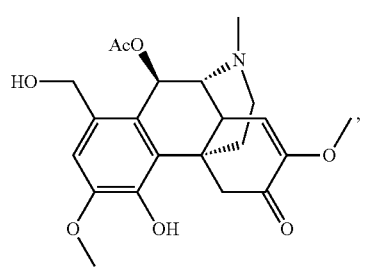
35
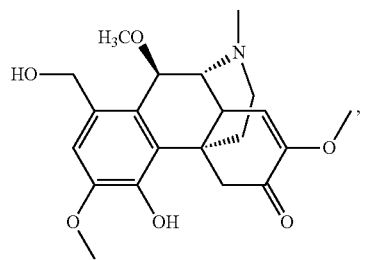
36
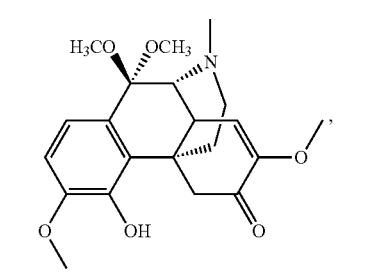
37
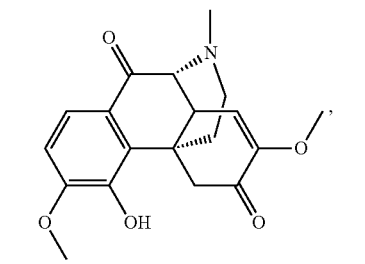
38
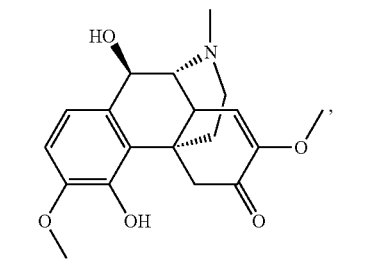
39
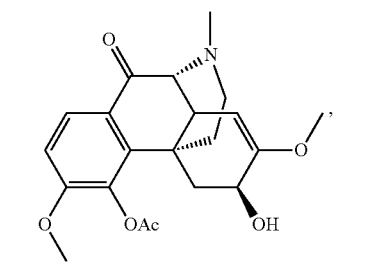

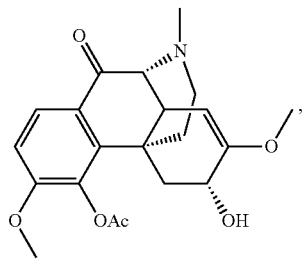

40

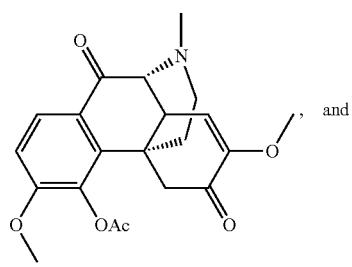

41 and

42

In the second aspect, the present invention provides a method for preparing the sinomenine derivatives of the invention, which can include one or more of the following steps (1) through (7):

(1) Sinomenine (or its hydrochloride salt) is reacted with iodobenzene diacetate (DIB) in an aqueous solution at room temperature for 0.5~4 hours to obtain compound C1. The molar ratio of sinomenine (or its HCl salt) to DIB is 1:1~2.

(2) Compound C1 is reacted with $R_{11}OH$, $R_{12}SH$, $R_{13}R_{14}NH$, $H_2O$,

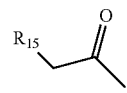

or $(R_{10}CO)_2O$ in an organic solvent to produce compound C2. Or, compound C1 is reacted with $R_{16}R_{17}R_{18}SiX$ in an organic solvent to obtain compound C3. The reaction time is 0.5~48 hours. The molar ratio of Compound C1 to $R_{11}OH$, $R_{12}SH$, $R_{13}R_{14}NH$, $H_2O$,

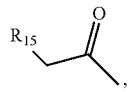

$(R_{10}CO)_2O$ or $R_{16}R_{17}R_{18}SiX$ is 1:1~10.

(3) Sinomenine or its derivative is reacted with DIB in methanol at room temperature for 0.5~48 hours to obtain Compound C4 or Compound C5, wherein the molar ration of sinomenine or its derivative to DIB is 1:1~2.

(4) Compound C4 dissolved in an organic solvent, kept at a temperature between ice bath and room temperature, is reduced with sodium borohydride for 1~24 hours to obtain Compound C7, wherein the molar ratio of Compound C4 to sodium borohydride is 1:1~4. Alternatively, Compound C4 in organic solvent may be heated under reflux with aluminium trichloride ($AlCl_3$) for 1~24 hours to obtain Compound C6, wherein the molar ratio of Compound C4 to aluminium trichloride is 1:1~5.

(5) Compound C5 dissolved in an organic solvent, kept at a temperature between ice bath and room temperature, is reduced with sodium borohydride for 1~24 hours to obtain Compound C8, wherein the molar ratio of Compound C4 to sodium borohydride is 1:1~4. Alternatively, Compound C5 with an aqueous solution of lithium hydroxide, kept at a temperature between ice bath and room temperature, may be hydrolyzed for 0.5~24 hours to obtain Compound C6, wherein the molar ratio of Compound C5 to lithium hydroxide is 1:1~10.

(6) Sinomenine or its derivative dissolved in an organic solvent, kept at a temperature between ice bath and room temperature, is reacted with acyl chloride or acid anhydride for 0.5~24 hours to obtain Compound C9, wherein the molecular ration of sinomenine or its derivative to acyl chloride or acid anhydride is 1:1~5. Compound C9 is reacted at room temperature with chromium trioxide in aqueous sulfuric acid solution for 1~24 hours to obtain Compound C10, wherein the molar ration of Compound C9 to chromium trioxide is 1:1~4.

(7) Compound C10 dissolved in an organic solvent, kept at a temperature between ice bath and room temperature, is reduced with sodium borohydride for 1~24 hours to obtain Compound C11, wherein the molecular ration of Compound C10 to sodium borohydride is 1:1~4. Alternatively, Compound C10 and aqueous lithium hydroxide solution is hydrolyzed in an ice bath or at room temperature for 0.5~24 hours to obtain Compound C11, wherein the molar ratio of Compound C10 to lithium hydroxide is 1:1~10.

The chemical reactions are as follows:
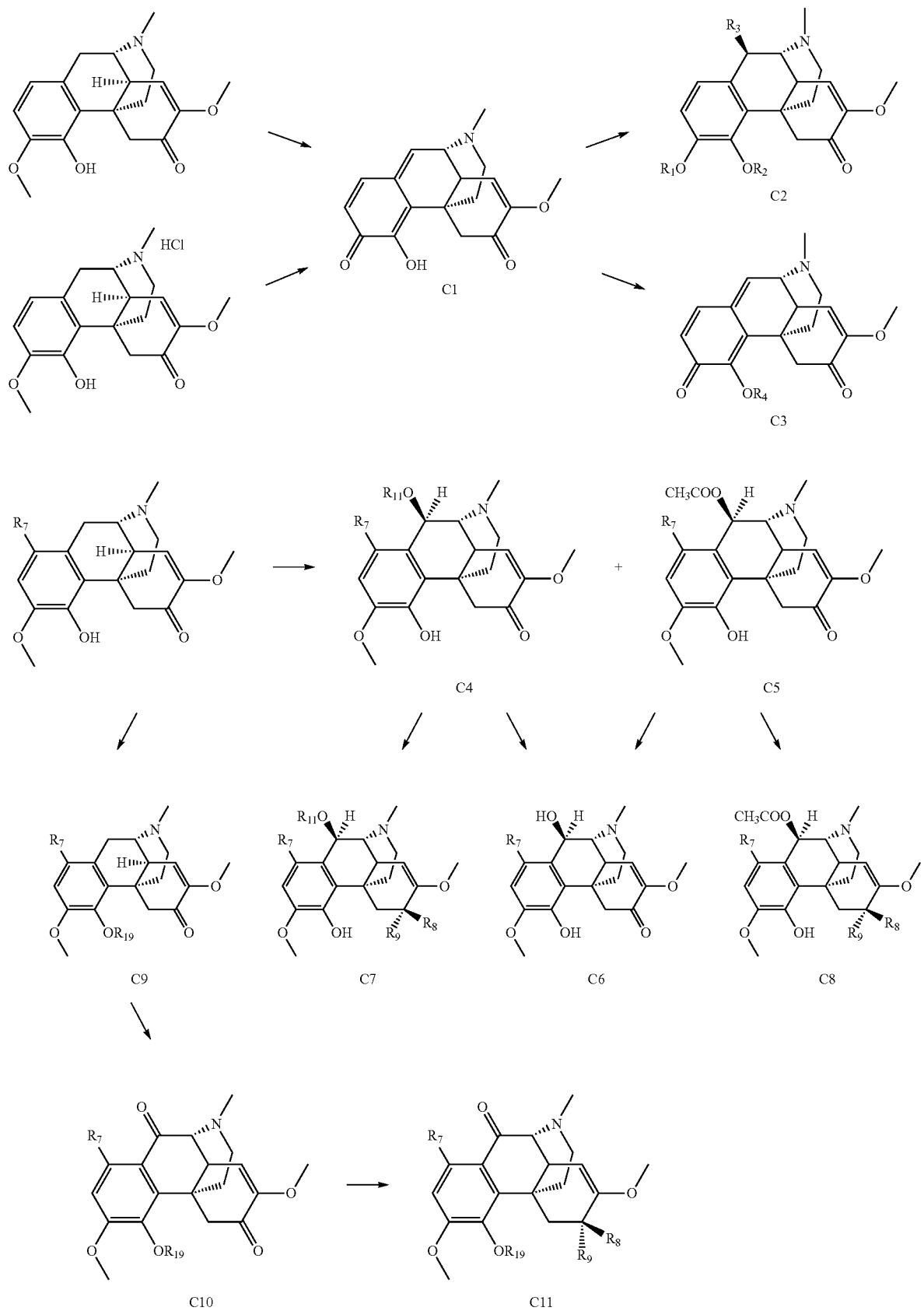

The Structures of Compounds C1-C11 are as follows:

wherein $R_1, R_2, R_3, R_4, R_5, R_6, R_7, R_8, R_9, R_{10}, R_{11}, R_{12}, R_{13}, R_{14}, R_{15}, R_{16}, R_{17}, R_{18}$ are as described above; $R_{19}$=H or $R_{10}$CO; wherein X is halogen, including chloro, bromo, or iodo.

The organic solvens referred to above includes, but are not limited to, methanol, ethanol, n-propanol, n-butanol, iso-propanol, dichloromethane, chloroform, 1,2-dichloroethane, carbon tetrachloride, ethyl ether, tetrahydrofuran, benzene, toluene, xylene, acetone, butanone, acetonitrile, N,N-dimethylformamide, and dimethylsulfoxide.

Sinomenine derivatives may be obtained with the following steps: Compound C1 and $R_{12}$SH are reacted in an organic solvent to obtain Compound C2. The reaction time is 0.5~48 hours, wherein the molar ration of Compound C1 to $R_{12}$SH is 1:1~10; wherein $R_{12}$ represents

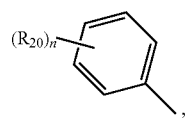, $R_{20}$ represents H or a substituent selected from the following group: halogen, $C_{1-4}$ alkyl, $C_{1-4}$ fluoroalkyl, —$NO_2$, —CN, $C_{1-4}$ alkoxy or —OH; n=1, 2, or 3; wherein Compound C1 is as previously described and Compound C2 has the following structure:

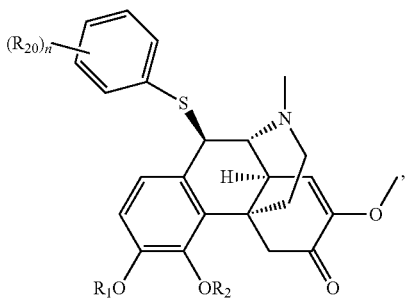

wherein $R_1$=H or $R_{10}$CO; $R_2$=H or $R_{10}$CO; $R_{10}$=$C_{1-6}$ alkyl, preferably $C_{1-4}$ alkyl.

Alternatively, it is recommended to use the following step (1) or steps (1)~(2) to obtain the desired compounds:

(1) Compound C1 and $R_{12}$SH are reacted in an organic solvent to obtain Compound C2-1, wherein the molar ratio of Compound C1 to $R_{12}$SH is 1:1~10.

(2) Compound C2-1 is reacted with an acyl chloride or an acid anhydride in an organic solvent, at a temperature between an ice bath temperature and room temperature, for 0.5~24 hours to obtain Compound C2-2, wherein the molar ration of sinomenine or its derivative to acyl chloride or acid anhydrice is 1:1~5.

The chemical reactions are as follows:

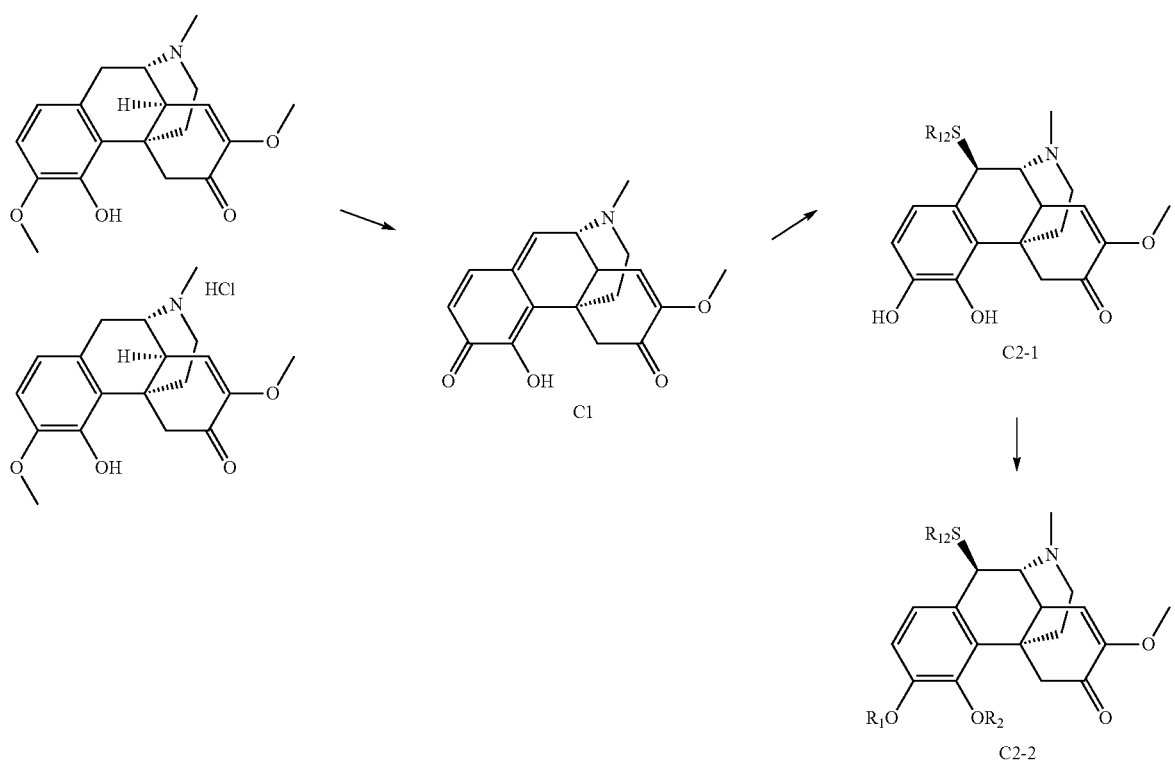

The structures of Compounds C1, C2-1 and C2-2 are as follows:

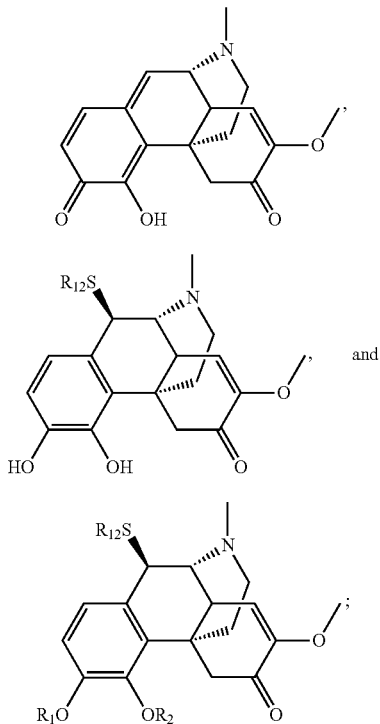

wherein $R_1$ represents $R_{10}CO$, $R_2$ represents $R_{10}CO$; $R_{12}$ represents

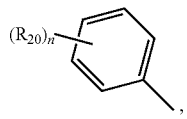

$R_{20}$ represents H or a substituent selected from the following group: halogen, $C_{1-4}$ alkyl, $C_{1-4}$ fluoroalkyl, —$NO_2$, —CN, $C_{1-4}$ alkoxy and —OH; n=1, 2, or 3; $R_{10}$=$C_{1-6}$ alkyl, preferably $C_{1-4}$ alkyl.

The third aspect of the invention provides a pharmaceutical composition, which comprises a therapeutically effective amount of a sinomenine derivative of the invention, its isomer, or a pharmaceutically acceptable salt, ester, or solvate thereof, a pharmaceutically acceptable carrier, excipient, or diluant.

In a preferred embodiment, the composition further comprises another therapeutical reagent for immune diseases.

In a preferred embodiment, the therapeutical reagent for immune diseases is selected from NSAID, glucocorticoids, or immune suppressants.

The fourth aspect of the invention provides uses of the sinomenine derivatives in the preparation of medicaments for treating immune diseases.

In a preferred embodiment, the immune diseases include inflammatory gastric intestinal diseases, inflammation, rheumatoid arthritis, juvenile rheumatoid arthritis, psoriatic arthritis, osteoarthritis, resilient rheumatoid arthritis, chronic rheumatoid arthritis, Crohn's disease, and asthma.

The fifth aspect of the invention provides a method for treating immune diseases in a subject, wherein the method comprises administering a sinomenine derivative to a subject in need of such treatments.

The sixth aspect of the invention provides a use of sinomenine derivatives in the preparation of a medicament for treating ore preventing a deases associated with abnormal TNF-α activities in a mammal.

In a preferred embodiment, the diseases associated with abnormal TNF-α activities include: inflammatory intestinal diseases, inflammation, rheumatoid arthritis, juvenile rheumatoid arthritis, psoriatic arthritis, osteoarthritis, resilient rheumatoid arthritis, chronic rheumatoid arthritis, osteoporosis/bone resorption, Crohn's disease, septic shock, endotoxin shock, atherosclerosis, ischemia-reperfusion injury, coronary heart disease, casculitis, amyloidosis, multiple sclerosis, septicemia, chronic recurrent uveitis, hepatitis C infection, malaria, alcerative colitis, cachexia, psoriasis, Wegenrer's granulomatosis, meningitis, plasmocytoma, endometriosis, Behcet's disease, AIDS, HIV infection, autoimmune disease, immune deficiency, common variable immune deficiency (CVID), chronic graft versus host disease, trauma and graft rejection reaction, adult respiratory distress syndrome, pulmonary fibrosis, recurring ovarian cancer, multiple myeloma, myeloproliferative disease, diabetes, juvenile diabetes, ankylosing spondylitis, delayed skin allergy, Alzheimer disease, systemic lupus erythrematosus, and allergic asthma.

In addition, the present invention provides a method for treating or preventing diseases associated with abnormal TNF-α activities in mammals. The method comprises administering to a subject in need thereof an effective amount of a sinomenine derivative of the invention. The sinomenine derivatives may be as described in preferred embodiments. Preferably, a pharmaceutical composition comprises one or more sinomenine derivatives.

The anti-inflamatory activities and anti-immune activities of sinomenine derivatives are assessed using in vitro TNF-α inhibition assays (Results see FIG. 1, FIG. 2, and FIG. 3).

This invention makes use of the easily oxidized phenol groups in sinomenine structuresto prepare a series of sinomenine derivatives by oxidation. These methods are unique and the product structures are novel. Using in vitro TNF-α inhibition assays, the activities of these sinomenine derivatives are evaluated. The results show that most compounds have anti-inflamatory activities, and some compounds have better activities as compared with sinomenine itself. These derivatives can potentially be used in the treatment of immune diseases such as rheumatoid arthritis. In addition, Compounds33, 34, and 35 showTNF-α stimulatory activities; these compounds deserve further studies.

DETAILED DESCRIPTION

Figure 1:
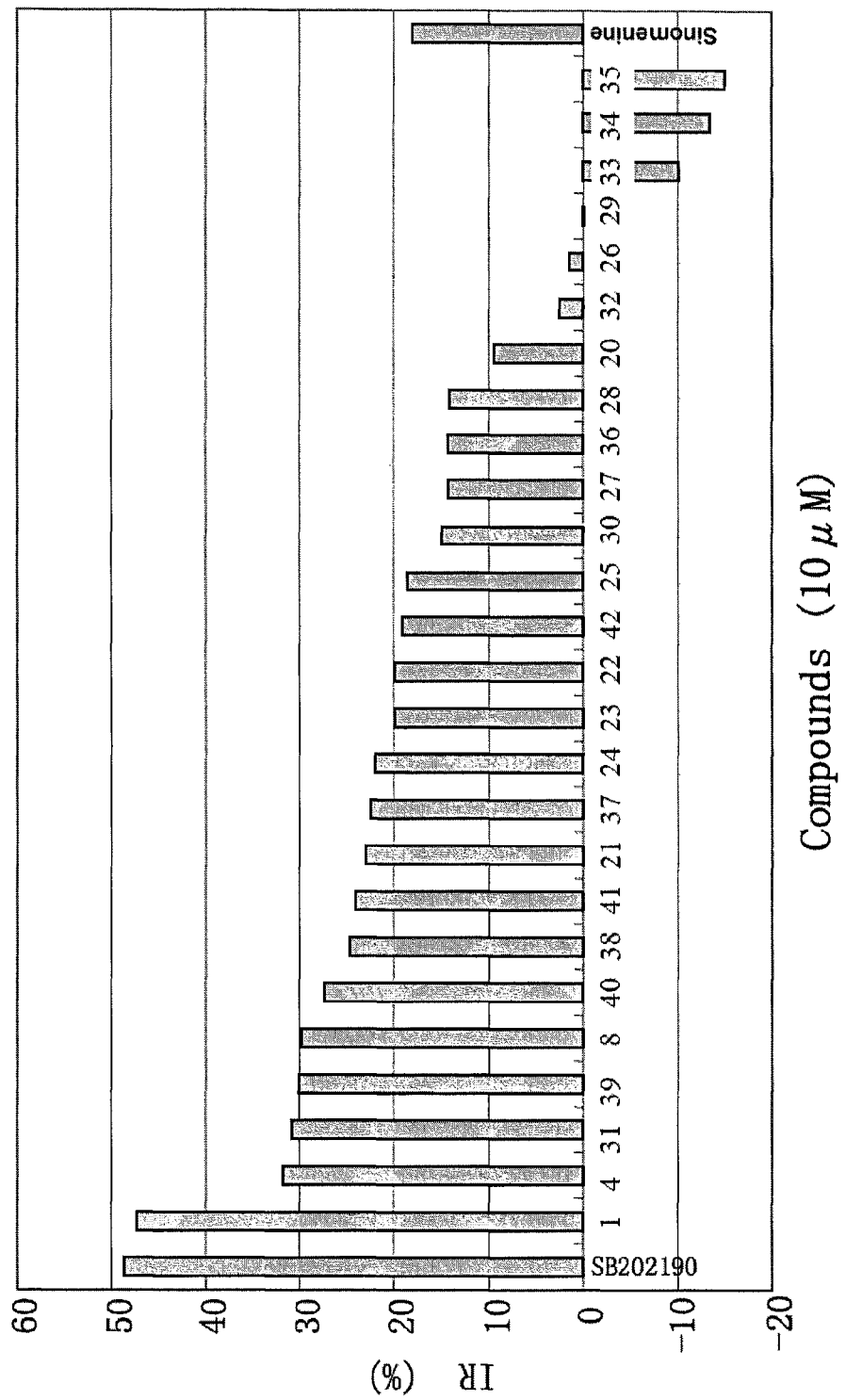
FIG. 1 shows results of anti-inflamatory and immune suppression activities of some compounds of the invention based on in vitro TNF-α inhibition assays. The horizontal axis indicates the compound numbers corresponding to the examples, and the vertical axis indicates the inhibition rate (IR) of TNF-α. The concentration used in the assays is 10 μM.

TNF-α exerts its functions mainly through two TNF receptors: TNF receptor I (renamed as CD 120a) and TNF receptor II (renamed as CD 120b). Most TNF-α functions are mediated by CD120a transduction. CD120b receptor is inducible and it preferably interacts with the membrane-bound TNF-α. Tartaglia et al., (1992), Vandenabeele et al., (1995), and Grell et al., (1995) have thoroughly investigated the physiological functions of TNF-α and described interference with TNF-α activities, such as organic compounds that can inhibit TNF-α activities are useful in the treatments of various diseases (symptoms).

TNF-α is a major cytokine secreted by monocyte in response to immune stimulation. To animals and human, application of TNF-α can cause inflammation, fever, abnormal cardiovascular functions, bleeding, coagulation, and a series of acute responses associated with acute infection and shock. In animals or human, excess production or controlled production of TNF often indicates one of the following diseases: endotoxemia and/or toxic shock syndrome (Tracey et al., Nature 330, 662-4 1987; Hinshaw et al., Circ Shock 30, 279-92 (1990)); cachexia (Dezube et al., Laucet, 335 (8690), 662 (1990)); adult respiratory distress syndrome (ARDS) (Millar et al., Laucet 2(8665), 712-714 (1989)).

TNF-α also plays an important role in bone absorption type diseases, including arthritis (Betolinni et al., Nature 319, 16-8 (1986)). Based on in vitro and in vivo test, it has been shown that TNF-α, by stimulation of osteoclast production or activation, can stimulate bone resorption and inhibit bone generation.

To date, the most relevant TNF-α related diseases are the release of TNF-α by tumor and host tissues and alignant tumor-related hypercalcemia (Calci. Tissue Int. (US), 46 (Suppl.), S3-10 (1990)). In bone marrow transplant patients, immune response is tightly associated with plasma TNF-α concentrations (Holler et al., Blood, 75 (4), 1011-1016 (1990)).

Lethal super acute neurological syndrome cerebral malaria is also related to the blood TNF-α levels. Cerebral malaria is the most dangerous type of malaria. When disease occurs, plasma TNF-α levels are directly correlated with disease conditions, and it often occurs in acute malaria patients (Grau et al., N. Engl. J. Med. 320 (24), 1586-91 (1989)).

TNF-α also plays an important role in chronic pneumonia. When lung accumulates silica, it will develop pneumosilicosis. Pneumosilicosis arises from fibrotic response of lung tissue, which leads to progressive respiratory failure. In animal pathologicl models, TNF-α antibodies can completely block silica induced lung fibrotic progession in mice (Pignet et al., Nature, 344:245-7 (1990)). In animal test, it has also been shown that animals with silica dust or asbestos dust induced fibrosis also have abnormally high levels of TNF-α in plasma (Bissonnette et al., Inflammation 13(3), 329-339 (1989)). Pathological studies reveal that lung tissues of patients with sarcoidosis also have substantially higher levels of TNF-α, as compared with normal individuals (Baughman et al., J. Lab. Clin. Med., 115 (1), 36-42 (1990). These observations suggest that inhibitors of TNF-α may have significant uses in the treatment of chronic lung diseases and lung injuries.

The reasons for inflammation in ischemia-reperfusion injury patients may be related to the abonormal levels of TNF-α in these patients. Furthermore, TNF-α is thought to be primary culprit of tissue damages caused by ischemia (Uadder et al, PNAS 87, 2643-6 (1990)).

Experiments have shown that TNF-α may initiate the replication of retroviruses, including HIV-1 (Duh et al., Proc. Nat. Acad. Sci., 86, 5974-8 (1989)). Before entry into T-cells, HIV virus needs to activate the T-cells. Furthermore, once an activated T-cell is infected by HIV virus, the T-cells must remain in the activated state in order for the HIV virus to express properly its genes and/or to replicate properly. Cytokines, especially TNF-α, play important functions in the T-cell regulated processes of HIV protein expression or virus replication. Therefore, inhibition of TNF-α production can inhibit HIV virus replication in T-cells (Poll et al., Proc. Nat. Acad. Sci., 87, 782-5 (1990); Monto et al., Blood 79, 2670 (1990); Poll et al., AIDS Res. Human Retrovirus, 191-197 (1992)).

cAMP can regulate manu cellular functions, such as inflammatory reactions, including asthma and inflammation (Lome and Cheng, Drugs of the futune, 17 (9), 799-807, 1992). During inflammation, cAMP concentration in leukocytes increase, resulting in inhibition of leukocyte activation, followed by the release of inflammation regulatory factors, including TNF-α, to aggravate inflammation in patients. Therefore, inhibition of TNF-α release can alleviate inflammatory diseases, including asthma.

Recently, Yanyan Yu et al. discovered that TNF-α plays an important role in hepatonecrosis in patients with viral hepatitis (Yanyan Yu et al., Chinese Internal Med. 1996, 35: 28-31), suggesting that inhibitors of TNF-α can be significant agents for the treatment of chronic liver diseases and liver injuries.

Yingxu Li et al. found that chronic liver disease patients have significantly higher levels of monocyte production and TNF secretion in the peripheral blood, and induction of other cytokine secretions (such as Il-1β, Il-6 and Il-8) and participate in the liver cell injury process (Qiqihaer Medical College Journal, 22(10): 1199-1120, 2001). Their results are consistent with results from Yoshioka et al. (Hepatology, 1989, 10:769-777) and Xin Wang et al. (China Infectious Disease Journal, 1997, 15(2): 85-88). They further showed that small molecule TNF-α inhibitors could significantly inhibit the secretion of TNF-α by peripheral monocytes in hepatitis patients, thereby providing pathological basis for TNF-α inhibitors in the treatment of hepatitis, cirrhosis, and hepatoma.

TNF, through stimulation of inflammatory cytokine production and section (Abboud H. E. Kidney Int., 1993; 43:252-267), stimulation of cell adhesion molecule expression (Egido J. et al, Kidney Int. 1993; 43 (suppl 39): 59-64j), and stimulation of the production and secretion of prostaglandin Gi (PGEz) and platelet activating factor (PAF) (Camussi G. et al., Kidney Int., 43 (suppl 39): 32-36), can lead to inflammatory reactions, such as inflammatory cell aggregation and adhesion, capillary dilation and permeability increase, induction of fever, increase of circulatory neutrophils and changes in blood dynamics, thereby leading to kidney cell injuries. Many researches suggest that TNF-α plays an important role in the initiation and progression of nephritis.

TNF-α, through activation of macrophage, immuno stimulation of T lymphocyte amplification, regulation of B lymphocyte differentiation, and enhancement of natural killer (NK) cell cytotoxicity effects, can participate in the regulation of immune functions. Therefore, reduction in TNF-α levels in patients and/or increasein cAMP levels in patient can provide an effective strategy for the treatment of many inflammatory, infectious, immuno or malignant tumor like diseases, including but not limited to sepsis shock, endotoxin shock, hemodynamic shock, sepsis syndrome, post ischemic reperfusion injury, malaria, mycobactrial infection, meningitis, psoriasis, congestive heart failure, fibrotic disease, cachexia, transplant immune rejection, cancer, autoimmune disease, opportunistic infection in AIDS, rheumatoid arthritis, hepatitis, nephrosis, rheumatoid spondylitis, etc.

Inflammatory cytokines, such as TNF, are involved in pathogenesis of psoriasis (B onifati and Ameglio, Int. J. Derm. 38: 241-251, 1999). Leonardi et al. (New Eng. J. Med. 349: 2014-2022, 2003) discovered that after a 24-week treatment of psoriasis using TNF antagonist, etanercept, the severity of the disease is significantly reduced. Boyman et al. (J. Exp. Med. 199: 731-736, 2004) transplanted a human tissue section from a symptomless prepsoriatic skin keratinocyte into AGR129 mice, which lacks interferon I and interferon II and Rag2, and therefore lacks B and T cells and has deverely impaired NK cell activities. After transplantation, human T cells undergo local multiplication, which is critical for the phenotype of psoriasis that displays papillomatosis and Jujube skin disease. Immunochemistry analysis of preposriatic skin, before and 8 weeks after transplantation, showed that in the transplant tissue, keratinocytes, dendritic cells, endothelial cells and immune cells are activated. T cells proliferation and the subsequence disease progression rely on TNF production, which can be inhibited by TNF antibodies or soluble fragments of the receptor. Boyman et al. concluded: that TNF-dependent activation of resident T cells is necessary and sufficient for the progression of psoriasis.

Based on studies in mice (Flynn et al., Immunit. 2: 561-572, 1995) and observations in patients receiving Infliximab (remicade) treatments for rheumatoid arthritis and regional ileitis (IBD 1; (Keane et al., N. Eng. J. Med. 345: 1098-1104, 2001), it is found that antibody mediated TNF neutralization can enhance sensitivity to tuberculosis. However, excess TNF may be related to severe TB pathology (Barnes et al., J. Immun. 145: 149-154, 1990). Using path and race segregation analysis and controlling environmental difference, Stein et al. (Hum. Hered. 60: 109-118, 2005) assessed the TNF secretion levels in TB patients in Uganda. The results show that mainly due to genetics, there is a strong genetic influence of TNF expression in TB, and there are possible heterozygote advantages. Common environment has least influence on TNF expression. Stein et al. concluded that TNF is an endophenotype of TB; it can provide improved detection of this disease—i.e., susceptibility loci.

Cytokine gene regulatory region single nucleotide polymorphism (SNPs) is related to susceptibility of many complicated diseases. TNF is an inflammatory cytokine, which provides the host with quick defense to infections. However, excess TNF can be lethal. Because TNF is used against various pathogens, each of which involves different risk and benefit, it can be predicted that this will promote the diversity of genetic elements that regulate TNF production.

Hemnann et al. (Europ. J. Clin. Invest. 28: 59-66, 1998) use PCR-SSCP and sequencing to screen for complete coding region and 1,053 bases upstream of the transcription start site in the TNF-α gene to investigate polymorphism. Five (5) polymorphisms are identified: four are located at positions −857, −851, −308, and −238 upstream of the transcription start site, and one is found at position +691 in the nontranscribed region. Three polymorphs (SNPs) located close to the TNF transcription start site at 238, −308, and −376 all have guanine replaced by adenine. Knight et al. (Nature Genet. 22: 145-150, 1999) disclosed that the allelic types are: 23861-238A, −3086/−308A, and 3766/−376A. They showed that changes in TNF-α promoter region are related to the following subsceptibilities: cerebral malaria (McGuire et al., Nature. 371: 508-511, 1994), mucocutaneous leishmaniasis (Cabrera et al., J. Exp. Med., 182: 1259-1264, 1995), death resulting from meningococcal diseases ((Nadel et al., J. Infect, Dis., 174: 878-880, 1996), lepra lepromatosa (Roy et al., J. Infect. Dis., 176: 530-532, 1997), scar trachoma (Conway et al., Infect. Immun. 65: 1003-1006, 1997), and asthma (Moffatt and Cookson, Hum. Molec. Genet., 6: 551-554, 1997).

Flora et al. (Hum. Molec. Genet. 12: 375-378, 2003) tested the connection between the polymorphism in the MHC region and mild malaria. Two point analysis revealed a linkage between mild malaria and TNFd (lod score=3.27), a high polymorphism marker in the MHC region. Multi-point analysis further revealed evidence for the linkage between mild malaria and the MHC region; it showed peak value similarity with TNF ((lod score=3.86). The authors speculated that genetic mutations in TNF may influence subsceptibility to mild malaria. However, polymorphisms TNF-238, TNF-244, and TNF-308 cannot explain the linkage between mild malaria and the MHC region.

Based on statistical analysis of Funayama et al. (Invest. Ophthal. Yis. Sci. 45: 4359-4367, 2004), it was shown that among the Japanese patients having POAG, possible interactions between optineurin polymorphisms and the TNF gene may increase the risk of developing glaucoma and potential progression.

By testing the regions 500 bp upstream of the transcription start site for the TNF and TNFR superfamily members, Kim et al. (Immunogenetics. 57:297-303, 2005) identified 23 new regulatory SNPs from Korean volunteers. Sequence analysis reveals that among these SNPs, 9 altered the predicted transcription factor binding sites. SNP database analysis reveals that the SNP allelic gene frequency is similar to that of Japanese test subjects, but different from those of Caucasian and African subjects.

Zinman et al. (J. Clin. Endocr. Metab. 84: 272-278, 1999) studied the Canadian native groups that live in isolation and have unusually high occurrence of NIDDM and found a relationship between TNF-α and body measurement and physiological variables in insulin-resistant and diabetic patients. Using homeostatic model assessment (HOMA) to assess insulin resistance, they found a moderate but statistically significant correlation between TNF-α and fasting insulin level, HOMA insulin resistance, waistline, fasting triglycerides, and systolic blood pressure. Under all conditions, the correlation coefficient is higher for female than for male. The authors conclude that among Canadian natives, within glucose tolerance range, there is a positive correlation between circulating TNF-α concentration and insulin resistance. The data indicate possible uses of TNF-α in pathophysiology of insulin resistance.

Obayashi et al. (J. Clan. Endocr. Metab., 85: 3348-3351, 2000) studied adult onset diabetic patients and identified the effect of TNF-α on insulin dependence. These patient have type I diabetes (IDDM)—HLA haplotype. They analyzed TNF-α in 3 groups of DRB 1*1502-DQB 1*0601—positive diabetic patients. In the beginning, these patients did not have ketosis or non-insulin dependent diabetes for more than 1 year. Group A includes 11 patients tested positive for antibodies against glutamic acid decarboxylase (GADab). These patients developed insulin dependence within 4 years of diabetes onset. Group B includes 11 patients tested positive for GADab. These patients maintained non-insulin dependence for over 12 years. Group C includes 12 type II diabetic patients tested positive for GADab. These patients developed insulin dependence within 4 years of diabetes onset. In addition, a control group includes 18 test subjects without diabetes. Among the test subjects in Group C and the Control group, there is a strong relationship between DRB 1*1502-DQB 1*0601 and TNF-α-13 allele. Among the Group A patients, there is a strong correlation between DRB 1*1502-DQB 1*0601 and TNF-α-12 allele. However, this is not the case in Group B. Interestingly, in Group B, none of the plasma samples from patients, who do not have TNF-α-12 and TNF-α-13, reacted with GAD65 in Western blot analysis. The author concluded that among the patients initially diagnosed as having type II diabetes and positive for GADab IDRB 1*1502-DQB 1*0601, TNF-α is related to the progression of insulin dependency. Furthermore, ascertaining the TNF-α genotypes of these patients would allow one to better predict the clinical outcome.

To study whether TNF-α gene is the gene responsible for diabetic changes, Li et al. (J. Clin. Endocr. Metab. 88: 2767-2774, 2003) investigated, among type II diabetes patients from families with type I and type II diabetes (type I/II family) or families with common type II diabetes, and adult onset type I diabetes, and control test subjects, the relationship between TNF-α promoter polymorphism (G to A substitution at location −308 and −238) and HLA-DQB 1 gene. TNF-α (308) AA/AG genotype frequency in adult onset type I diabetes patients increases (55%, 69 our of 12). However, as compared to the control group (33%, 95/284; for type I, P<0.0001), type II diabetic patients from the type I/II families (35%, 33/93) or from the common type II families (31%, 122 of 395) show similar frequencies. TNF-α (308) A and DQB 1*02 allelic gene in type I patients (Ds=0.81; P<0.001, relative to Control Group, Ds=0.25) and type II diabetic patients from the type I/II families (relative to the Control Group, Ds=0.59, P<0.05) exhibit linkage imbalance. However, this is not the case in type II diabetic patients (Ds=0.39). Among the type II patients from the type I/II families, only those with DQB*02 exhibit a relationship between polymorphism and insulin defect phenotype. Compared to patients with the GG polymorphism, common type II patients with the AA/AG polymorphisms have a lower waist-to-hip ratio [0.92 (0.12) vs. 0.94 (0.11), P=0.008] and a lower fasting serum C concentration [0.48 (0.47) vs. 0.62 (0.46) nmol/L, P=0.020], regardless whether DQB 1*02 is present. The authors concluded that TNF-α is unlikely the second gene on the short arm of chromosome 6 that is responsible for the changes in the phenotype of type II diabetic patients. The type II diabetic patients are from the type I/II diabetic families.

Shbaklo et al. (Hum. Immunol. 64: 633-638, 2003) assessed, among the 210 diabetic patients in Paris, the relationship between TNF-α promoter −863 and −1031 polymorphisms and type I diabetes. Their results show that in this group, the C allelic gene of −863 polymorphism has advantages, while A allelic gene is very rare (2%). However, at location −1031, the distribution of C and T allelic genes in patients (respectively, 17.8% vs. 82.2%) is similar to the Control Group ((21.4% n vs. 79.6%). They did not find a relationship between TNF-α gene location 1031 polymorphism and type I diabetes. This result is consistent with those proven by family association test and transmission disequilibrium test. However, when comparing patient genotypes, it was found that type I male patients have a recessive CC genotype, but the female patients do not have the recessive CC geneotype.

In a study with 641 patients with myocardial infarction and 710 control test subjects, Hemnann et al. (Europ. J. Clin. Invest. 28: 59-66, 199) concluded that it is unlikely that TNF-α gene polymorphism is involved in a significant manner to enhance the risk of coronary heart disease. However, the 308 mutation might be related to obesity should be further studies.

Because it has been reported that TNF-α expression is increased in obese rodent model and in obese human fat tissue, TNF-α is thought to be a candidate gene for obesity. Norman et al. (J. Clin. Invest. 96: 158-162, 1995) evaluated gene loci of three polymorphic dinucleotide repeat sequences near the TNF-α gene in Pima Indians. In sibling-paired linkage analysis, for example through hydrostatic weight measurements, body fat percentages and the nearest (10 kb) TNF-α marker are linked (304 sibling pairs, P=0.002). Through variable analysis, the same marker and body mass index (BMI) are found to be related (P=0.01). To search for DNA mutations in TNF-α that might be helpful for obesity, they performed SSCP analysis on genes from 20 obese test subjects and 20 relatively skinny test subjects. No evidence was found to link the promoter region single base polymorphism allelic gene with body fat percentages.

Rosmond et al. (J. Clin. Endocr. Metab. 86: 2178-2180, 2001) used 284 unrelated Swedes born in 1944 to study possible effects of the G-to-A substitution at location −308 in the TNF-α gene promoter region on the estimation of obesity and insulin, glucose, and lipid metabolism, as well as circulating hormones (including salivary cortisol). Genotype reveals that the allelic gene frequency for an allelic G is 0.7, while the allelic gene frequency for an allelic A is 0.23. Among the TNF-α genotypes, detection of different levels of salivary corticol indicates tha, as compared to other genotypes, among the rare allelic gene homozygotes, in the morning before stimulation with standard lunch and 30 and 60 minutes after stimulation with standard lunch, the levels of cortisol are significantly higher. In addition, as compared with other genotype groups, rare allelic gene homozygotes exhibit a trend toward higher average values for BMI, waist-to-hip ratio, and abdominal radial diameter. The results also show that there is a weaker trend toward higher insulin and glucose levels in subjects with the A/A genotype. Rosmond suggests that the relationship between the increased cortisol secretion and such polymorphisms may be the previously observed endocrine system that relates to correlation between NcoI TNF-α polymorphism and obesity, as well as insulin resistance.

To evaluate the function of TNF-α in the pathogenesis of hyperandrogenism, Escobar-Morreale et al. (J. Clin. Endocr. Metab. 86:3761-3767, 2001) assessed the plasma TNF-α levels and polymorphisms in the TNF-α gene promoter region in a group of 60 BMI-matched hyperandrogenism patients and a control group of 27 healthy subjects. Compared to the control group, the hyperandrogenism patients have slightly increased plasma TNF-α levels. When the test subjects are categorized according to body weights, plasma TNF-α levels in relatively obese patients are increased as compared with relatively skinny subjects. When compared between obese patients with obese control subjects, the difference is statistical insignificant. The TNF-α gene polymorphisms are found to be equally distributed between hyperandrogenism patients and control subjects. However, in the patients and the control subjects, carriers of 308A mutation have significantly increased basal and leuprorelin acetate-stimulated plasma androgen and 17-hydroxy progesterone levels. The authors concluded that TNF-α system may facilitate the pathogenesis of hyperandrogenism.

De Groof et al. (J. Clin. Endocr. Metab. 87: 3118-3124, 2002) evaluated the GH/IGF 1 axis (growth hormone/insulin-like growth factor I axis) and the levels of IGF binding protein (IGFBPs), IGFBP3 protease, glucose, insulin, and cytokine in 27 children with severe septic shock due to meningococcal septicemia during the first 3 days after admission. The medium age of these patients was 22 months. Nonsurvivors had extremely high GH levels that were significant different compared with mean GH levels in survivors during a 6-h GH profile. Significant differences were found between nonsurvivors and survivors for the levels of total IGF-I, free IGF-I, IGFBP-1, IGFBP-3 protease activity, IL-6, and TNF-α. The pediatric risk of mortality score correlated significantly with levels of IGFBP-1, IGFBP-3 protease activity, IL-6, and TNF-α and with levels of total IGF-I and free IGF-I. GH levels and IGFBP-1 levels were extremely elevated in non-survivors, whereas total and free IGF-I levels were markedly decreased and were accompanied by high levels of the cytokines IL-6 and TNF-α.

Mira et al. (J.A.M.A. 282: 561-568, 1999) reported results of their multicenter case-controlled studies of TNF2 allele 3086-A polymorphism frequency among the septic shock patients. They investigated 89 patients with septic shock and 87 healthy unrelated blood donors. Mortality among patients with septic shock was 54%. The polymorphism frequencies of the controls and the patients with septic shock differed only at the TNF2 allele (39% vs 18% in the septic shock and control groups, respectively, P=0.002). TNF2 polymorphism frequency was significantly greater among those who had died (52% vs 24% in the survival group, P=0.008). Concentrations of TNF-α were higher in 68% and 52% with the TNF2 and TNF1 polymorphisms, respectively, but their median values were not statistically different. Mira et al. estimated that patients with the TNF2 allele had a 3.7-fold risk of death.

Because lethal cerebral malaria correlates with high levels of TNF-α, McGuire et al. (Natune, 371: 508-511, 1994) performed a large scale case comparison study in Gambia children. Their study revealed that homozygotes for the TNF2 allele have a relative risk of 7 for death or severe neurological sequeale due to cerebral malaria. The TNF2 allele is a variant of the TNF-α gene promoter region (Wilson et al., Hum. Molec. Genet., 1: 353, 1992). Although the TNF2 allele is in linkage disequilibrium with several neighbouring HLA alleles, McGuire et al. showed that this disease association is independent of HLA class I and class II variation. These data suggest that regulatory polymorphisms of cytokine genes can affect the outcome of severe infection. The maintenance of the TNF2 allele at a gene frequency of 0.16 in The Gambia implies that the increased risk of cerebral malaria in homozygotes is counterbalanced by some biological advantage.

Hill (Proc. Assoc. Am. Phys. 111: 272-277, 1999) described the genetic basis for malaria susceptibility and resistance, and listed 10 genes that affect *plasmodium* falciparum and/or *plasmodium vivax* susceptibility and resistance. He pointed out that the linkage between a regulated variant of TNF gene promoter (Wilson et al., Hum. Molec. Genet. 1: 353, 1992) and cerebral malaria (McGuire et al., Nature 371: 508-511, 1994) has promoted evaluation of pharmaceuticals that may reduce the activity of this cytokine (van Hensbroek et al., J. Infect. Dis. 174:1091-1097, 1996).

Through systematic DNA fingerprinting of the TNF promoter region, Knight et al. (Nature Genet. 22: 145-150, 1999) identified a SNP that can induce helix-turn-helix transcription factor OCT 1 (POU2F 1) to bind to a new region for protein-DNA complex interactions and alter the gene expression in human monocytes. About 5% of African population was found to have the OCT1 binding genotype. In a large scale comparative case and control study between West African and East African populations, after correcting for other HLA alleles known to be related to TNF polymorphism and linkage, it was found that this genotype is related to the increased susceptibility to cerebral malaria.

Galbraith and Pandey (Hum. Genet., 96: 433-436, 1995) investigated tumor necrosis factor alpha (TNF-α) phenotypes of two polymorphic systems in 50 patients with alopecia areata. Wilson et al. (Hum. Molec. Genet., 1: 353, 1992) identified the first double allelic TNF-α polymorphism, which includes a single G-A base change at location −308 in the promoter region of this gene. The −308 A polymorphism (referred to as TNF2) results in significantly higher transcription frequency of the rare allele in IDDM patients. However, this is determined by the increase in the cooccurrence in HLA-DR3. HLA-DR3 is related to T2. Based on the report of D'Alfonso and Richiardi (Immunogenetics 39: 150-154, 1994), the TNF-α polymorphism also includes a −238 location G-to-A transition in that gene. Galbraith and Pandey (Hum. Genet., 96: 433-436, 1995) discovered that in alopecia areata patients, the distribution of TNF-α T1, T2 phenotypes differed between patients with the patchy form of disease and patients with totalis/universalis disease. There was no significant difference in the distribution of TNF-α G, A phenotypes between patient groups. The results of this study indicate the existence of genetic heterogeneity between the two forms of alopecia areata, and suggest that the TNF-α gene is closely linked with the major histocompatibility complex on chromosome 6 and that it may play a role in the pathogenesis of the patchy form of disease.

Mulcahy et al. (Am. J. Hum. Genet., 59:676-683, 1996) determined the inheritance of five microsatellite markers in the TNF gene region in 50 multiplex rheumatoid arthritis (RA) families. Overall, 47 different haplotypes were observed. One of these haplotypes was present in 35.3% of the affected, but in only 20.5% of unaffected, individuals (P<0.005). This haplotype accounted for 21.5% of the parental haplotypes transmitted to affected offspring and only 7.3% not transmitted to affected offspring (P=0.0003). Additional studies showed that the tumor necrosis factor-lymphotoxin (TNF-LT) region appears to influence susceptibility to RA, distinct from HLA-DR. These studies uses transmission disequilibrium test (TDT) as reported in Spielman et al. (Am. J. Hum. Genet., 52: 506-516, 1993).

TNF-α may be involved in the pathogenesis of ankylosing spondylitis and rheumatoid arthritis. Gorman et al. (New Engl. J. Med. 346: 1349-1356, 2002) assessed the efficacy of TNF-α in the treatment of ankylosing spondylitis. They used etanercept, which is a human 75-kD chimeric fusion protein joined with human IgG 1 $F_c$ fragment, to treat 40 patients with active inflammatory diseases for 4 months, resulting in fast, significant, and sustained improvement.

Ota et al. (Genes Immunity 1: 260-264, 2000) used dinucleotide repeat sequence polymorphism located near TNF gene to test the genetic linkage between osteoporosis and osteopenia phenotypes and allelic variations at the TNF gene loci from 192 sibling paired adult Japanese women from 136 families. Evidence of linkage between TNF-α gene loci and osteoporosis show: the average allele sharing among the inconsistent pairs is 0.478 (P=0.30), and the average allele sharing among the consistently affected pairs is 0.637 (P=0.001). The linkage between TNF and osteoporosis among the consistently affected pairs is also significant ((P=0.017). The analysis limited to the same age group postmenopause women shows a similar or even stronger linkage between the two pheonotypes.

Winchester et al. (Hum. Genet., 107: 591-596, 2000) studied the association of a G-308A variant of TNF-α and an insertion/deletion (I/D) variant of angiotensin converting enzyme (ACE) with a self-reported history of childhood asthma, in two population groups. The TNF-α-308A allele (−308A) was significantly associated with self-reported childhood asthma in the UK/Irish group, but not in the South Asian population. The ACE DD genotype was not associated with childhood asthma in either population group. Therefore, the TNF-α-308A allele or a linked major histocompatibility complex (MHC) variant may be a genetic risk factor for childhood asthma in the UK/Irish sample.

Koss et al. (Genes Immun. 1: 185-190, 2000) found that TNF-α-308A promoter polymorphism was more frequent in women, but not in men, with extensive colitis compared to distal colitis. This difference was even greater for the combined TNF-2-LT alpha-2 haplotype. These women also have a lymphotoxin alpha (LTA) gene containing A instead of C at location 720. The polymorphism is related to the significantly higher TNF production in patients with Crohn's disease, while in ulcerative colitis patients, this polymorphism is related to the lower production of TNF gene having an A substituting for G at location 238 in the TNF gene.

Sashio et al. (Immunogenetics 53:1020-1027, 2002) studied the role of TNF gene and TNFRSF 1 B gene polymorphism in ulcerative colitis and Crohn's disease susceptibilities. They studies 124 Crohn's disease patients, 106 ulcerative colitis patients, and 111 unrelated healthy control subjects. They investigated two SNPs, −3086A and −2386A, of the TNF-α gene. Between the ulcerative colitis patients and the control subjects, there is a difference in the carrier frequency for the AGC308A, −2386 haplotype (odd ratio 4.76).

Van Heel et al. (Hum. Molec. Genet. 11:1281-1289, 2002) pointed out that TNF expression was increased in inflammatory bowel disease (IBD) and TNF mapped to IBD3 susceptibility locus. Transmission disequilibrium and case—control analyses, in two independent Caucasian cohorts, showed a novel association of the TNF-857C promoter polymorphism with IBD (overall P=0.001 in 587 IBD families). Further genetic associations of TNF-857C with IBD sub-phenotypes were seen for ulcerative colitis and for Crohn's disease, but only in patients not carrying common NOD2 mutations. The genetic data suggest a recessive model of inheritance. The transcription factor OCT1 binds TNF-857T but not TNF-857C, and interacts in vitro and in vivo with the pro-inflammatory NF-κB transcription factor p65 subunit at an adjacent binding site. The authors speculated that, in digestive tissues, the interactions between these transcription factors and specific TNF allele may be related to IBD pathogenesis.

In a case-control study involving 304 Australian Crohn's disease patients and 231 healthy control subjects, Fowler et al. (J. Med. Genet. 42:523-528, 2005) discovered significant association of higher producing IL10-1082G and TNF-α-857C alleles with strictureing behavior, which was strongest when these alleles were combined and persisted after multivariate analysis.

To study whether TNF-α promoter polymorphism is associated with the clearance of hepatitis virus B, Kim et al. (Hum. Molec. Genet., 12:2541-2546, 2003) investigated the genotype of 1,400 test subjects. Among the test subjects, 1,109 are chronic HBV carriers and 291 have spontaneously recovered. The TNF-α promoter alleles that were previously reported to be associated with higher plasma levels, i.e. the presence of the −308A allele or the absence of the −863C (TNF-α−863C/C) variant, were strongly associated with the resolution of HBV infection. Haplotype analysis also revealed that TNF-α haplotype 1 (−1031T; −863C; −857C; −308G; −238G; −163G) and haplotype 2 (−1031C; −863A; −857C; −308G; −238G; −63G) were significantly associated with HBV clearance, showing protective antibody production and persistent HBV infection, respectively (P=0.003-0.02).

Pharmaceutical compositions in preferred embodiments may be used in the treatment of diseases medicated by TNF-α activities. Furthermore, methods for treating diseases medicated by TNF-α activities are provided. A treatment includes administering to subject in need thereof an effective amount of a compound of the preferred embodiments, for example using a pharmaceutical composition. Embodiments of the invention also provide uses of compounds of the preferred embodiments in the manufacture of pharmaceuticals. The pharmaceuticals, for example, include pharmaceutical compositions for treating diseases medicated by TNF-α activities. Treatments include treating existing diseases or symptom, as well as prevention of the diseases or symptoms.

Examples of disease include those that can be treated by inhibiting or blocking TNF-α using compounds of preferred embodiments of the invention, including those mediated by TNF-α activities. The diseases include chronic inflammatory disease, allergic disease, autoimmune disease, cardiovascular disease, neurodegenerative disease, viral disease (e.g., retroviral disease), cancer, pain, and post-transplantation disease. More specifically, the diseases include rheumatoid arthritis, osteoarthritis, osteoporosis, multiple sclerosis, atherosclerosis, psoriasis, systemic lupus erythematosus (SLE), (acute) glomerular nephritis, asthma, asthmatic bronchiectasis, chronic obstructive pulmonary disease (COPD), acute respiratory distress syndrome (ARDS), inflammatory bowel diseases (e.g., cicatrizing enteritis), colitis (e.g., ulcerative colitis), septicemia, malaria (e.g., cerebral malaria), altered mental status (AMS), neurodegenerative disease (e.g., Alzheimer's disease), Parkinson disease, Bertolotti-Barcin syndromes, graft versus host disease (GvHD), vasculitis, uveitis, (insulin-dependent) diabetes (e.g., diabetes), consequences of (adult) (multiple) trauma (e.g., multiple organ failure), acute and chromic pain (e.g., nerve pain, primary and subsequent inflammatory dermatitis), atopic dermatitis, trichomadesis (hair loss), rhinitis (allergic), allergic conjunctivitis, meningitis, myasthenia gravis, scleroderma, sarcoidosis, and cancer (e.g., blood system cancers).

Definition

Unless otherwise defined, the term "hydrocarbyl" by itself or as part of other substituents means a straight chain (i.e., unbranched) or branched, or cylic hydrocarbyl or a combination thereof. It can be saturated, monounsaturated, or polyunsaturated, containing the designated number of atoms (e.g., $C_1$-$C_{10}$ means 1-10 carbon atoms). Saturated hydrocarbyls include, but are not limited to, the following: methyl, ethyl, propyl, isopropyl, n-butyl, iso-butyl, tert-butyl, cyclohexyl, cyclohexylmethyl, cyclopropylmethyl, such as, n-pentyl, n-hexyl, n-heptyl, n-octyl, their homologs or isomers, and the like. Unsaturated hydrocarbyls include, but are not limited to, ethenyl, 2-propenyl, butenyl, 2-iso-pentenyl, 2-butadienyl, penta-2,4-dienyl, 3-penta-1,4-dienyl, ethynyl, 1-propynyl, "Alkyl" represents a straight chain, branched chain, or cyclic hydrocarbyl. The term includes straight chain alkyl, such as methyl, ethyl, propyl, butyl, pentyl, hexyl, heptyl, octyl, nonyl, decyl, undecyl, dodecyl, and the like. This term also include branched chain isomers of these groups, which include, but are not limited to, —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), CH$_2$CH$_2$CH(CH$_3$)$_2$, —CH$_2$CH$_2$CH(CH$_3$)(CH$_2$CH$_3$), CH$_2$CH$_2$CH(CH$_2$CH$_3$)$_2$, CH$_2$CH$_2$C(CH$_3$)$_3$, —CH$_2$CH$_2$C(CH$_2$CH$_3$)$_3$, CH(CH$_3$)CH$_2$CH(CH$_3$)$_2$, —CH(CH$_3$)CH(CH$_3$)CH(CH$_3$)$_2$, —CH (CH$_2$CH$_3$)CH(CH$_3$)CH(CH$_3$)(CH$_2$CH$_3$), etc. The term "alkyl" also includes cycloalkyl, such as cyclopropyl, cyclobutyl, cyclopentyl, cyclohexyl, cycloheptyl, and cyclooctyl. Furthermore, these cyclic compounds may be substituted with the straight chain or branched chain alkyls described above. Therefore, preferred alkyls include straight chain alkyls and branched chain alkyls having 1-10 carbon atoms, more preferably C$_{1-6}$ alkyl, e.g., C$_{1-4}$ alkyl.

In this description, the term "C$_{1-4}$ fluoroalkyl" means a C$_{1-4}$ alkyl containing 1-9 fluorine atoms.

In this description, the term "alkyloxy" means "alkyl-O—," wherein the alkyl group is as defined above.

In this description, the term "aryl" means single ring or multi-ring aromatic groups having 5-14 carbon atoms. Carbon ring aromatic group means aromatic groups containing only carbon atoms in the ring. Examples of aromatic rings include benzyl, naphthyl, etc.

In this description, the term "heterocycle" or "heterocyclyl" means a C$_3$-C$_{20}$ cyclic group containing 1-3 hetero atoms and the remaining atoms on the ring are carbon atoms, wherein the hetero atoms are selected from O, S, or N. Heterocycles include nitrogen-containing heterocycles, oxygen-containing heterocycles, and sulfur-containing heterocycles. In this description, examples of the 5-membered 6-membered ring nitrogen-containing heterocycles include pyrrolyl, imidazolyl, pyrazolyl, pyridyl, pyrimidyl, etc. Examples of the 5-membered 6-membered ring oxygen-containing heterocycles include furanyl or pyranyl. Examples of the 5-membered 6-membered ring sulfur-containing heterocycles include thienyl.

The term "oxo" means an oxygen attached to a carbon atom via a double bond.

The term "halo" or "halogen" means F, Cl, Br, or I.

The invention includes sinomenine derivatives described herein and pharmaceutically acceptable salts thereof.

Examples of pharmaceutically acceptable salts include salts formed between the sinomenine derivatives of the invention and inorganic and organic acids. Examples of usable inorganic acids include hydrochloric acid, hydrobromic acid, nitric acid, sulfuric acid, and phosphoric acid, etc. Examples of organic acids include formic acid, oxalic acid, acetic acid, tartaric acid, methanesulfonic acid, benzenesulfonic acid, malic acid, toluene-p-sulfonic acid, etc. The salts further include salts of basic amino acids, such as arginine, lysine, and ornithine, and salts of acidic amino acids, such as aspartic acid and glutaric acid. Examples of pharmaceutically acceptable salts further include salts formed between the sinomenine derivatives of the invention and inorganic and organic bases. Examples of usable inorganic bases include alkaline metal hydroxides (e.g., sodium hydroxide, potassium hydroxide, etc.), alkaline earth metal hydroxides (e.g., calcium hydroxide, magnesium hydroxide, etc.), and aluminium hydroxide, ammonium hydroxide, etc. Examples of usable organic bases include trimethyl amine, triethyl amine, pyridine, picoline, ethanolamine, diethanolamine, triethanolamine, dicyclohexyl amine, N,N'-dibenzyl-ethylenediamine, etc.

The sinomenine derivatives of the invention may include their enantiomers, diastereomers, tautomers, and cis/trans conformers. All these isomers are included in the preferred embodiments of the invention, including mixtures of these compounds. Compounds of preferred embodiments may have chiral centers. For example they may include asymmetric carbon atoms, and they may exist as anatiomers, diastereomers, and their mixtures, such as racemates. Asymmetirc carbon atoms may exist in (R)-, (S)-, or (RS)-configurations, preferably in (R)- or (S)-configurations, or as mixtures.

According to the need, the pure isomers may be purified from isomer mixtures using conventional methods. Compounds of preferred embodiments may also include tautomers, when the tautomers may exist.

In addition, compounds of preferred embodiments may exist in multiple crystal forms, which may be included in preferred embodiments. Furthermore, compounds of some preferred embodiments may form solvates with water or other organic solvents. These solvates are also within the scope of preferred embodiments.

Compositions

The present invention includes compositions that include the sinomenine derivatives of the invention.

In this invention, one may use convention methods to mix sinomenine derivatives of the invention with pharmaceutically acceptable carriers, binders, or diluents to form compositions of the invention. The compositions may be pharmaceutical compositions. The carriers may include (but are not limited to): saline, buffers, glucose, water, glycerol, ethanol, and a combination thereof.

The compositions of the invention may be in solid forms (e.g., granules, tablets, freeze dried powders, suppositories, capsules, sublingual tablets) or liquid forms (e.g., oral liquids, or injections, etc.), or in other suitable forms. The active ingredients in the compositions of the invention typically account for 0.01~99% by weight, preferably 0.1~95%, more preferably 0.1~90%, and most preferably 1-80%.

Compositions of the invention may be in single dose form or in multiple dose form. According to administration dosages, they generally contain 1~1000 mg/dose, preferably 2~500 mg/dose, more preferably 5~100 mg/dose.

Compositions of the invention may be administered by conventional methods, which include (but are not limited to): oral, intramuscular injection, hypodermic injection, intravenous injection, etc. Preferred embodiments use oral administration. The amounts of compositions of the invention administered are calculated based on the active ingredients, generally 0.01~500 mg/kg body weight/day, more preferably 0.1~50 mg/kg body weight/day.

Pharmaceutical Compositions and Their Uses

The present invention also provides a pharmaceutical composition, which includes: (a) an effective amount of a sinomenine derivative of the invention, and (b) a pharmaceutically acceptable carrier, diluent or excipient.

As used in this description, the term "a composition of the invention" includes pharmaceutical compositions, as long as it contains a sinomenine derivative of the invention as an active ingredient.

In this invention, the term "containing" means various components may be used together with a mixture or composition of the invention.

In this invention, "pharmaceutically acceptable" ingredient is suitable for use in human and/or animals without excessive adverse effects (e.g., toxicity, irritation, and allergic reaction), i.e., a substance with reasonable efficacy/risk ratios.

In this description, the term "an effective amount" means an amount of a therapeutic agent that can treat, alleviate or prevent the target disease or condition, or an amount that can exhibit a detectable therapeutic or prevention effects. To a specific subject, the precise effective amount is determined by the subject's body types and health condition, nature and extent of the disease, as well as the selected therapeutic agent and/or combinations of therapeutic agents. Therefore, it is useless to preselect a precise effective amount. However, under a given condition, an effective amount can be ascertained using routine experiments, and a clinician can assess an effective amount.

For purposes of this invention, an effective amount to be given to a subject may be about 0.01 mg/kg to about 500 mg/kg, preferably 0.05 mg/kg~200 mg/kg body weight, of an active substance of the invention. In addition, an active substance of the invention may be used together with other therapeutic agents.

Pharmaceutical compositions may also include pharmaceutically acceptable carrier. The term "pharmaceutically acceptable carrier" refers to a carrier used in administering therapeutical agents; it meets the following conditions: the carriers themselves do not induce production of antibody harmful to the subject being treated with the composition, and do not have excessive toxicity after administration. These carriers are well known to one of ordinary skill in the field. In Remington's Pharmaceutical Sciences, Mack Pub. Co., N.J. (1991), there is detailed discussion of pharmaceutically acceptable carriers. Such carriers include (but are not limited to): saline, buffer, glucose, water, glycerol, ethanol, adjuvant, and combinations thereof.

In therapeutic compostions, pharmaceutically acceptable carriers may include liquids, such as water, saline, glycerol and thanol. In addition, these carriers may contain auxiliary materials, such as moisturizing agents or emulsifiers, pH buffers, etc.

The compounds or pharmaceutically acceptable salts therefore and their compositions may be administered orally and by intravenous injections, intramuscular injections, or hypodermic injection, preferably by oral administration. Solid carriers include: starch, lactose, dicalcium phosphate, microcrystalline cellulose, sucrose, and kaolin. Liquid carriers include: sterile water, polyethylene glycol, nonionic surfactants, and cooking oil (e.g., corn oil, peanut oil, and sesame oil), as long as they are compatible with the characteristics of the active ingredient and the requirement of the delivery modes. In the preparation of pharmaceutical composition, the commonly used auxiliary agents may also be advantageously included, such as flavoring agents, coloring agents, preservatives, and antioxidants, e.g., vitamin E, vitamin C, BHT (butylated hydroxytoluene) and BHA (butylated hydroxyanisole).

Compositions of the invention and their pharmaceutical compositions may also be stored in a sterilized device suitable for injection of infusion. Generally, in a pharmaceutical composition of the invention, a sinomenine derivative function as an active ingredient may account for 0.01~99% of the total weight, preferably 0.1~95%, more preferably 0.1~90%, most preferably 1~80%, and the remaining is pharmaceutically acceptable carriers and other additives.

Administration and Dosage Forms

Pharmaceutical compositions of the invention may be prepared as any conventional dosage forms using conventional methods.

The dosage forms of pharmaceutical compositions of the invention may vary, as long as the active ingredient can be effectively delivered into a body of a mammal Compositions may be prepared as various forms suitable for the administration methods. For example, pharmaceutical composition may be prepared as a tablet, pill, powder, lozenge, bag, cachet, elixir, suspension, emulsion, solution, syrup, spray (in a solid or liquid substrate), ointment, soft gel and hard gel capsules, suppository, sterile injection solution, powders in sterile packages, etc. Sinomenine derivatives of the invention preferably are stored in a suitable solid or liquid carrier or a diluent solution.

Sinomenine derivative compositions of the invention preferably are administered orally. Oral dosage forms include, but are not limited to, tablets, capsules, dispersible powders, particles or suspensions (e.g., containing about 0.05~5% suspension agent), syrup 9 containing about 10~50% sugar), and elixirs (containing about 20~50% alcohol). Alternatively, sinomenine derivative compositions may exist as sterile solution for injection or suspension form (containing about 0.05~5% suspension agent in an isotonic medium) for non-gastrointestinal administration. For example, these pharmaceutical preparations may include 25~90%, generally about 5~60% (by weight), of active ingredients.

Once a composition of the invention is prepared, it may be given directly to the subject. The target for prevention or treatment may be animals, particularly human. A pharmaceutical composition containing an active ingredient of the invention may be administered by oral administration, hypodermic injection, intradermal injection or intravenous injection, etc. a therapeutic dosage regimen may be a single dose regimen or multi-dose regiment.

The sinomenine derivatives of the invention and their compositions may also be administered parenterally or intraperitoneally. They can also be mixed in water containing surfactants (e.g., hydroxypropyl cellulose) to prepare solutions or suspensions containing these active ingredients. They may also be mixed with glycerol, liquids, polyethylene glycol to prepare dispersions. Under conventional storage and use conditions, these preparations may include preservatives to prevent microbe growth.

The dosage forms suitable for injection include: sterile aqueous solution or dispersion or sterile powders (for instantaneous preparation of sterile injection solutions or dispersions). Under all conditions, such dosage forms should be sterile and should be fluids to facilitate extrusion of fluids from injectors. These dosage forms should be stable under the preparation and storage conditions, and they should contamination by microbes. Carriers may be solvents or dispersant media, which contain liquids such as water, alcohol (e.g., glycerol, propylene glycol, and liquid polyethylene glycol), a suitable mixture thereof, and vegetable oil.

The effective amounts of the active ingredients can be varied according to the delivery modes and the severity of the disease conditions. However, in general, active ingredients of to invention, when used at about 1-300 mg/kg body weight, can produce satisfactory effects, preferably the therapeutic amounts are separated into 1-3 doses each day, or they are given as slow release forms. For most large mammals, the daily total dose may be about 5-1000 mg, preferably about 10-500 mg. Dosage forms suitable for internal administration include those containing 1-200 mg active ingredients mixed with solid or liquid pharmaceutically acceptable carriers. These doses may be adjusted to provide the best therapeutic responses. For example, according to the urgent requirements of the disease conditions, the compositions may be given in several separate doses each day or the doses may be accordingly reduced.

The compositions or pharmaceuticals of the invention may also contain other active ingredients, such as nonsteroid anti-inflammatory drugs, glucocorticoids, immune suppressants, etc.

When two or more pharmaceuticals are administered together, they generally produce effects that are superior to the effects of individual pharmaceuticals. Preferably, these pharmaceuticals or other preparations, when used together with sinomenine derivatives of the invention, do not interfere with the therapeutic efficacies of the sinomenine derivatives.

EXAMPLES

The present invention is further illustrated with the following specific examples. However, it should be understood that these examples are used for illustrating the invention and are not used to limit the scope of the invention. In the experimental procedures of the following examples, if specific conditions are not given, they are generally performed under conventional conditions or are performed according to the conditions recommended by the manufacturers.

Example 1

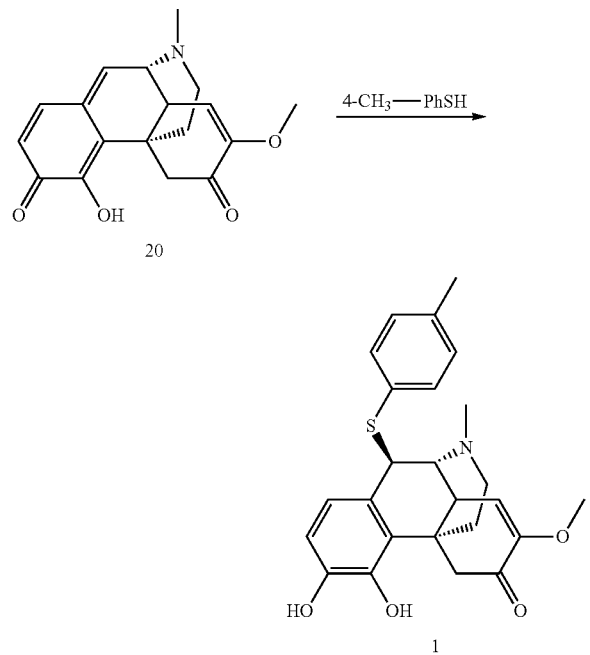

Compound 20 (0.615 g, 1.96 mmol) and dichloromethane (10 mL) are added in a 50 mL pear-shaped flask. The mixture is stirred at room temperature. P-tolyl mercaptan (0.368 g, 2.96 mmol, 1.5 equiv.) is added. The stirring is continued after the addition until TLC shows the disappearance of the starting material. To work up, petroleum ether is added to the reaction solution to precipitate the product, which is collected by suction filtration, washed with petroleum ether, and evaporated to give a final product (0.68 g, 79%).

M.p. 224-225° C. (dec.); $[\alpha]_D^{26}$=7.0 (c 0.50, CHCl$_3$—CH$_3$OH=10:1); $^1$H NMR (DMSO-d$_6$, 400 MHz): δ 9.47 (1H, s), 8.18 (1H, s), 7.57 (2H, d, J=8.0 Hz), 7.25 (2H, d, J=7.6 Hz), 7.02 (1H, d, J=8.4 Hz), 6.67 (1H, d, J=8.0 Hz), 6.27 (1H, d, J=2.0 Hz), 4.47 (1H, s), 4.18 (1H, d, J=15.2 Hz), 3.53 (3H, s), 3.11-3.18 (1H, m), 2.99 (1H, brs), 2.39 (1H, d, J=15.2 Hz), 2.33 (3H, s), 2.24-2.32 (1H, m), 1.93 (3H, s), 1.80 (1H, td, J=4.4, 10.8 Hz), 1.62-1.76 (2H, m); $^{13}$C NMR (DMSO-d$_6$, 75 MHz): δ 192.4, 149.4, 143.9, 137.3, 132.7, 132.0, 129.8, 128.3, 123.7, 120.3, 117.8, 113.3, 59.7, 53.9, 48.4, 45.9, 44.7, 43.6, 41.7, 35.5, 20.6; IR (KBr): 3325.9, 2940.9, 2831.0, 1666.8, 1619.8, 1491.3, 1291.3, 1202.0, 1151.8, 1092.9, 808.1, 497.4 cm$^{-1}$; HRMS (ESI, m/z) C$_{25}$H$_{28}$N$_1$O$_4$S$_1$ (M+H$^+$) calculated: 438.1734, detected: 438.1742.

Example 2

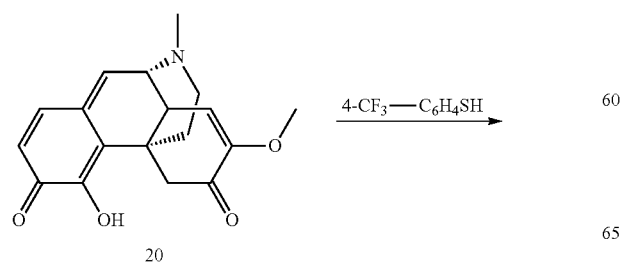

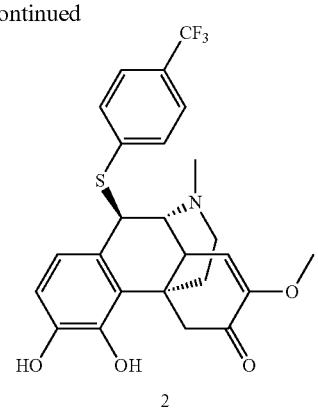

Compound 20 (1.0 g, 3.19 mmol) and dichloromethane (30 mL) are added in a 50 mL pear-shaped flask. The mixture is cooled in an ice bath. 4-trifluoromethylbenzene mercaptan (0.62 g, 3.51 mmol, 1.1 equiv.) is added. The stirring is continued after the addition, and the reaction is allowed to warm up to room temperature until TLC shows the disappearance of the starting material. To work up, the reaction solution is evaporated to dryness, and the residue is purified on a column to give a white solid (1.21 g, 77%).

M.p. 240-241° C. (dec.); $[\alpha]_D^{27}$=−19.9 (c 0.60, DMSO); $^1$H NMR (DMSO-d$_6$, 400 MHz): δ 9.53 (1H, s), 8.24 (1H, s), 7.82 (2H, d, J=8.4 Hz), 7.75 (2H, d, J=8.0 Hz), 6.96 (1H, d, J=8.4 Hz), 6.68 (1H, d, J=8.0 Hz), 6.19 (1H, d, J=2.0 Hz), 4.79 (1H, s), 4.19 (1H, d, J=15.2 Hz), 3.53 (3H, s), 3.18 (1H, d, J=2.8 Hz), 3.03 (1H, s), 2.41 (1H, d, J=15.2 Hz), 2.31-2.39 (1H, m), 2.16 (3H, s), 1.84-1.97 (1H, m), 1.68-1.78 (2H, m); $^{19}$F NMR (CDCl$_3$, 400 MHz): δ-59.69; IR (KBr): ν$_{max}$ 3437.6, 2954.3, 1692.0, 1682.3, 1629.7, 1484.1, 1323.9, 1286.4, 1202.8, 1173.2, 1116.4, 1091.5, 1061.8, 812.2 cm$^{-1}$; MS (ESI, m/z): 492.0 (M+H)$^+$, C$_{25}$H$_{24}$F$_3$NO$_4$S elemental analysis, calculated: C, 61.09; H, 4.92; N, 2.85. detected: C, 60.97; H, 4.98; N, 2.68.

Example 3

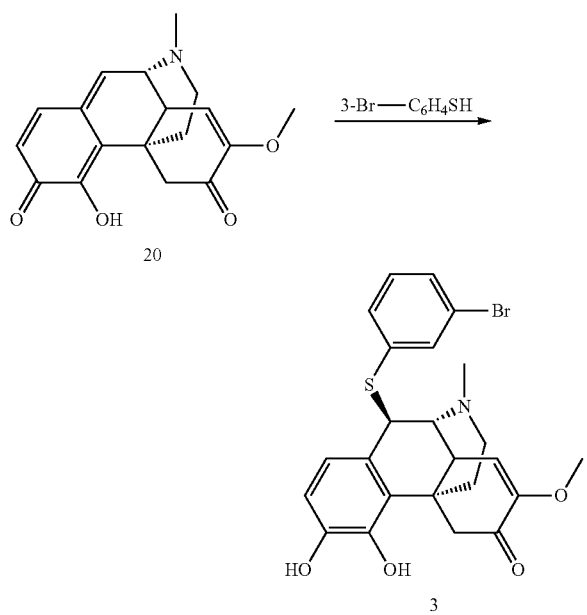

Compound 20 (1.0 g, 3.19 mmol) and dichloromethane (30 mL) are added in a 50 mL pear-shaped flask. The mixture is stirred in an ice bath. A solution of 3-bromobenzene mercaptan (0.36 mL, 3.51 mmol, 1.1 equiv.) in dichloromethane (15 mL) is added dropwise. The stirring is continued after the addition. The solution is allowed to warm up to room temperature and stirred until TLC shows the disappearance of the starting material. To work up, the reaction solution is evaporated to dryness, and the residue is purified on a column to give a white solid (1.25 g, 78%).

M.p. 205-207° C. (dec.); $[\alpha]_D^{27}$=14.7 (c 0.50, DMSO); $^1$H NMR (DMSO-d$_6$, 400 MHz): δ 9.50 (1H, s), 8.20 (1H, s), 7.90 (1H, t, J=1.6 Hz), 7.65 (1H, d, J=8.0 Hz), 7.53 (1H, d, J=8.0 Hz), 7.37 (1H, t, J=8.0 Hz), 7.00 (1H, d, J=8.4 Hz), 6.67 (1H, d, J=8.4 Hz), 6.23 (1H, d, J=2.0 Hz), 4.66 (1H, s), 4.18 (1H, d, J=15.2 Hz), 3.52 (3H, s), 3.15 (1H, d, J=2.8 Hz), 3.01 (1H, s), 2.40 (1H, d, J=15.2 Hz), 2.28-2.36 (1H, m), 2.06 (3H, s), 1.79-1.91 (1H, m), 1.66-1.78 (2H, m); $^{13}$C NMR (DMSO-d$_6$, 100 MHz): δ 192.4, 149.5, 144.1, 144.0, 138.4, 133.4, 131.0, 130.4, 130.1, 127.6, 123.8, 122.1, 120.5, 117.7, 113.3, 59.9, 53.9, 48.4, 45.9, 44.6, 43.3, 41.7, 39.7, 35.3; IR (KBr): ν$_{max}$ 3457.1, 2932.2, 1694.1, 1626.4, 1556.6, 1484.5, 1449.8, 1379.7, 1286.9, 1203.5, 1175.0, 1146.3, 1085.5, 1001.8, 911.9, 787.3, 514.0 cm$^{-1}$; HRMS (ESI, m/z) C$_{24}$H$_{25}$NO$_4$SBr (M+H$^+$) calculate: 502.0682, detected: 502.0691.

Example 4

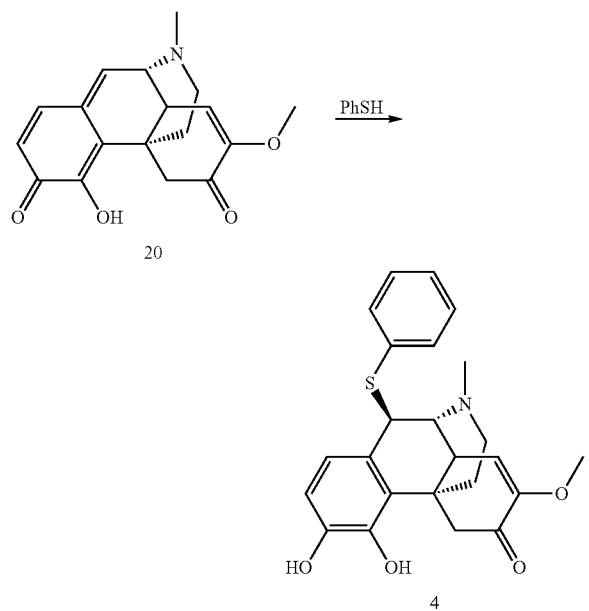 [SMILES: COC1=CC2[C@@H]3C=C4C=CC(=O)C(O)=C4[C@]2(CCN3C)CC1=O ; "PhSH" ; COC1=CC2[C@@H]3[C@H](Sc4ccccc4)c4ccc(O)c(O)c4[C@]2(CCN3C)CC1=O]

Compound 20 (0.5 g, 1.6 mmol) and dichloromethane (10 mL) are added in a 100 mL pear-shaped flask. The mixture is stirred in an ice bath. A solution of benzene mercaptan (0.18 mL, 1.75 mmol, 1.1 equiv.) in dichloromethane (5 mL) is added dropwise. The stirring is continued after the addition. The solution is allowed to warm up to room temperature and stirred until TLC shows the disappearance of the starting material. To work up, anhydrous ether is added to the reaction solution to precipitate the solids, which are collected by suction filtration, washed with ether, and evaporated to give the product (0.55 g, 81%).

M.p. 210-212° C. (dec.); $[\alpha]_D^{25}$=−3.4 (c 0.20, CHCl$_3$-CH$_3$OH=10:1); $^1$H NMR (DMSO-d$_6$, 400 MHz): δ 9.49 (1H, s), 8.19 (1H, s), 7.68 (1H, d, J=7.2 Hz), 7.43 (2H, t, J=7.2 Hz), 7.36 (1H, t, J=7.2 Hz), 7.01 (1H, d, J=8.4 Hz), 6.67 (1H, d, J=8.0 Hz), 6.26 (1H, d, J=2.0 Hz), 4.55 (1H, s), 4.18 (1H, d, J=15.2 Hz), 3.53 (3H, s), 3.15 (1H, d, J=2.8 Hz), 3.00 (1H, brs), 2.39 (1H, d, J=15.2 Hz), 2.26-2.34 (1H, m), 1.96 (3H, s), 1.82 (1H, td, J=4.8, 10.8 Hz), 1.67-1.76 (2H, m); $^{13}$C NMR (DMSO-d$_6$, 75 MHz): δ 192.5, 149.4, 144.0, 144.0, 135.6, 132.3, 129.2, 128.2, 127.6, 123.8, 120.3, 117.8, 113.3, 59.8, 53.9, 48.4, 46.0, 44.7, 43.4, 41.7, 35.5; IR (KBr): 3449.4, 2932.2, 2497.0, 1692.9, 1630.6, 1580.5, 1481.4, 1381.9, 1286.7, 1202.0, 1145.5, 1001.2, 812.9, 750.2 cm$^{-1}$; HRMS (ESI, m/z) C$_{24}$H$_{26}$N$_1$O$_4$S$_1$ (M+H$^+$) calculated: 424.1577, detected: 424.1577.

Example 5

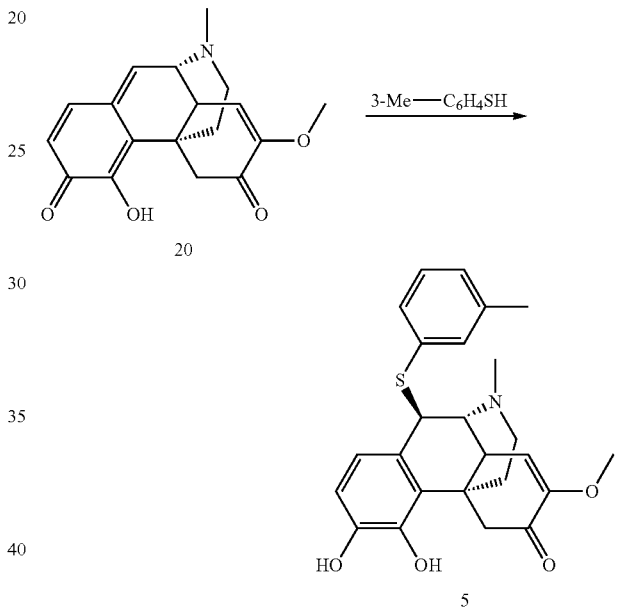

Compound 20 (1.0 g, 3.19 mmol) and dichloromethane (30 mL) are added in a 50 mL pear-shaped flask. The mixture is stirred in an ice bath. A solution of 3-methylbenzene mercaptan (0.42 mL, 3.51 mmol, 1.1 equiv.) in dichloromethane (15 mL) is added dropwise. The stirring is continued after the addition. The solution is allowed to warm up to room temperature and stirred until TLC shows the disappearance of the starting material. To work up, the reaction solution is evaporated to dryness, and the residue is purified on a column to give a white solid (1.12 g, 80%).

M.p. 230-231° C. (dec.); $[\alpha]_D^{27}$=1.7 (c 0.60, DMSO); $^1$H NMR (DMSO-d$_6$, 400 MHz): δ 9.50 (1H, s), 8.21 (1H, s), 7.49 (1H, s), 7.45 (1H, d, J=7.2 Hz), 7.30 (1H, t, J=7.2 Hz), 7.16 (1H, d, J=6.8 Hz), 7.01 (1H, d, J=8.4 Hz), 6.67 (1H, d, J=8.0 Hz), 6.26 (1H, s), 4.55 (1H, s), 4.19 (1H, d, J=15.2 Hz), 3.53 (3H, s), 3.16 (1H, s), 2.99 (1H, s), 2.39 (1H, d, J=15.6), 2.33 (3H, s), 2.21-2.36 (1H, m), 1.99 (3H, s), 1.78-1.90 (1H, m), 1.60-1.78 (2H, m); $^{13}$C NMR (DMSO-d$_6$, 100 MHz): δ 192.4, 149.4, 144.0, 138.6 135.4, 132.4, 129.0, 128.2, 123.7, 120.3, 117.8, 113.3, 59.8, 53.9, 48.4, 45.9, 44.7, 43.2, 41.7, 35.4, 20.7; IR (KBr): ν$_{max}$ 3435.5, 2938.8, 1693.4, 1625.5, 1483.7, 1450.5, 1275.0, 1202.9, 1023.8, 787.6, 726.6, 516.8 cm$^{-1}$; HRMS (MALDI m/z) C$_{25}$H$_{28}$NO$_4$S (M+H$^+$) calculated: 438.1734, detected: 438.1741.

Example 6

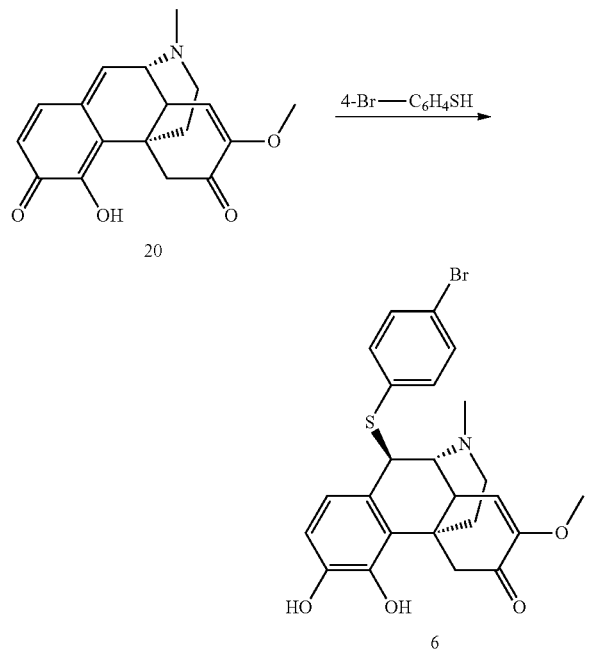

Compound 20 (1.0 g, 3.19 mmol) and dichloromethane (30 mL) are added in a 50 mL pear-shaped flask. The mixture is stirred in an ice bath. p-Bromobenzene mercaptan (0.66 g 3.51 mmol, 1.1 equiv.) is added. The stirring is continued after the addition. The solution is allowed to warm up to room temperature and stirred until TLC shows the disappearance of the starting material. To work up, the reaction solution is evaporated to dryness, and the residue is purified on a column to give a white solid (1.54 g, 96%).

M.p. 224-225° C. (dec.); $[\alpha]_D^{27}$=−20.5 (c 0.50, DMSO); $^1$H NMR (DMSO-d$_6$, 400 MHz): δ 9.53 (1H, s), 8.22 (1H, s), 7.55-7.73 (4H, m), 6.99 (1H, d, J=8.4 Hz), 6.67 (1H, d, J=8.4 Hz), 6.22 (1H, d, J=2.0 Hz), 4.57 (1H, s), 4.18 (1H, d, J=15.2 Hz), 3.51 (3H, s), 3.14 (1H, d, J=2.8 Hz), 3.00 (1H, s), 2.40 (1H, d, J=15.6 Hz), 2.27-2.35 (1H, m), 2.01 (3H, s), 1.77-1.88 (1H, m), 1.65-1.77 (2H, m); $^{13}$C NMR (DMSO-d$_6$, 100 MHz): δ 192.5, 149.5, 144.2, 144.0, 135.2, 134.0, 132.1, 127.8, 123.8, 120.7, 120.4, 117.7, 113.3, 59.9, 54.0, 48.4, 45.9, 44.7, 43.5, 41.8, 39.8, 35.4; IR (KBr): ν$_{max}$ 3311.5, 2936.4, 1665.3, 1621.8, 1490.8, 1472.3, 1587.2, 1490.8, 1472.3, 1380.1, 1290.5, 1177.4, 1150.7, 1089.9, 1005.2, 813.5, 611.9 cm$^{-1}$; HRMS (MALDI, m/z) C$_{24}$H$_{25}$NO$_4$SBr (M+H$^+$) calculated: 502.0682, detected: 502.0697.

Example 7

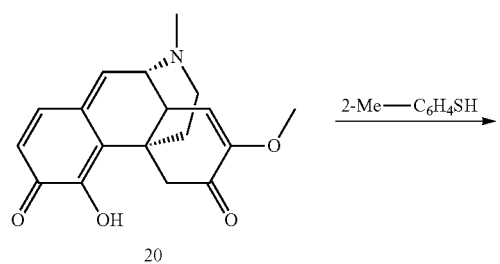

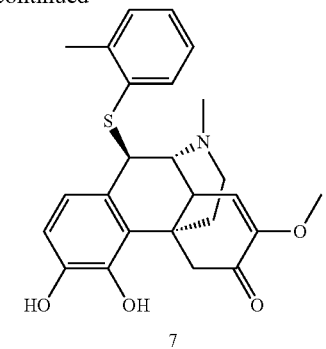

Compound 20 (1.0 g, 3.19 mmol) and dichloromethane (30 mL) are added in a 50 mL pear-shaped flask. The mixture is stirred in an ice bath. A solution of 2-methylbenzene mercaptan (0.41 mL, 3.51 mmol, 1.1 equiv.) in dichloromethane (15 mL) is added dropwise. The stiffing is continued after the addition. The solution is allowed to warm up to room temperature and stirred until TLC shows the disappearance of the starting material. To work up, the reaction solution is evaporated to dryness, and the residue is purified on a column to give a white solid (1.06 g, 76%).

M.p. 216-217° C. (dec.); $[\alpha]_D^{27}$=−18.4 (c 0.50, DMSO); $^1$H NMR (DMSO-d$_6$, 400 MHz): δ 9.49 (1H, s), 8.19 (1H, s), 7.70-7.78 (1H, m), 7.31-7.38 (1H, m), 7.22-7.31 (2H, m), 7.02 (1H, d, J=8.4 Hz), 6.68 (1H, d, J=8.4 Hz), 6.36 (1H, d, J=2.0 Hz), 4.45 (1H, s), 4.19 (1H, d, J=15.2 Hz), 3.53 (3H, s), 3.13 (1H, d, J=3.2 Hz), 3.02 (1H, s), 2.41 (1H, d, J=15.2 Hz), 2.26-2.36 (1H, m), 1.94 (3H, s), 1.84 (1H, dt, J=4.8, 11.2 Hz), 1.65-1.78 (2H, m); $^{13}$C NMR (DMSO-d$_6$, 100 MHz): δ 192.4, 149.5, 144.0, 144.0, 139.2, 134.5, 132.7, 130.5, 128.3, 127.5, 126.5, 123.9, 120.2, 117.8, 113.4, 60.1, 53.9, 48.5, 45.9, 44.6, 42.4, 41.7, 39.8, 35.3, 20.3; IR (KBr): ν$_{max}$ 3448.4, 2944.5, 1683.1, 1647.4, 1479.5, 1379.7, 1283.3, 1200.7, 1146.3, 912.9, 812.5, 761.9 cm$^{-1}$; HRMS (MALDI, m/z) C$_{25}$H$_{28}$NO$_4$S (M+H$^+$) calculated: 438.1734, detected: 438.1750.

Example 8

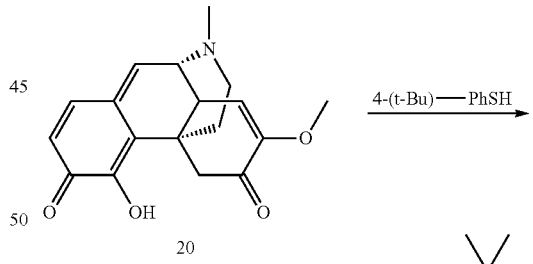

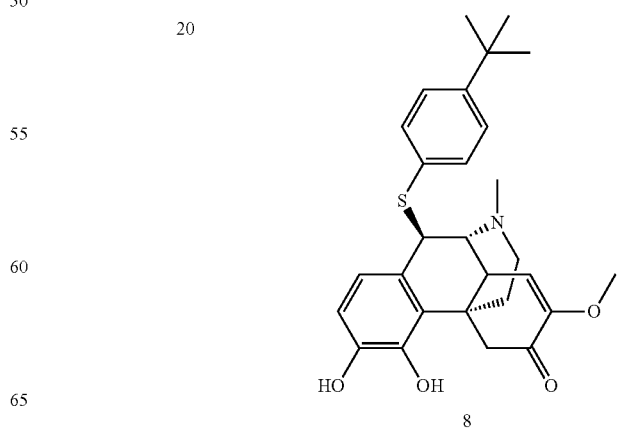

Compound 20 (0.5 g, 1.6 mmol) and dichloromethane (10 mL) are added in a 50 mL pear-shaped flask. The mixture is stirred in an ice bath. A solution of p-tert-butylbenzene mercaptan (0.29 mL, 1.68 mmol, 1.05 equiv.) in dichloromethane (5 mL) is added dropwise. The stirring is continued after the addition. The solution is allowed to warm up to room temperature and stirred until TLC shows the disappearance of the starting material. To work up, the reaction solution is evaporated to dryness, and the residue is purified on a column to give a white solid (0.51 g, 67%).

M.p. 232-233° C. (dec.); $[\alpha]_D^{25}$=5.84 (c 0.30, CHCl$_3$—CH$_3$OH=10:1); $^1$H NMR (DMSO-d$_6$, 400 MHz): δ 9.47 (1H, s), 8.18 (1H, s), 7.58 (2H, d, J=8.0 Hz), 7.44 (2H, d, J=8.4 Hz), 7.00 (1H, d, J=8.4 Hz), 6.67 (1H, d, J=8.4 Hz), 6.26 (1H, d, J=1.6 Hz), 4.51 (1H, s), 4.18 (1H, d, J=15.2 Hz), 3.53 (3H, s), 3.14 (1H, brs), 2.99 (1H, brs), 2.39 (1H, d, J=15.2 Hz), 2.25-2.35 (1H, m), 1.96 (3H, s), 1.82 (1H, td, J=4.8, 10.8 Hz), 1.66-1.76 (2H, m), 1.29 (9H, s); $^{13}$C NMR (CDCl$_3$/CD$_3$OD=10/1, 75 MHz): δ 195.0, 151.2, 150.2, 143.9, 143.4, 132.4, 132.2, 128.9, 126.2, 122.7, 121.0, 117.8, 113.6, 60.6, 54.6, 48.9, 46.5, 45.5, 43.9, 41.8, 40.3, 35.9, 34.5, 31.1; IR (KBr): 3439.7, 2935.5, 2866.3, 2359.0, 1693.1, 1631.3, 1482.2, 1286.6, 1202.5, 1146.2, 813.6 cm$^{-1}$; HRMS (ESI, m/z) $C_{28}H_{34}N_1O_4S_1$ (M+H$^+$) calculated: 480.2203, detected: 480.2208.

Example 9

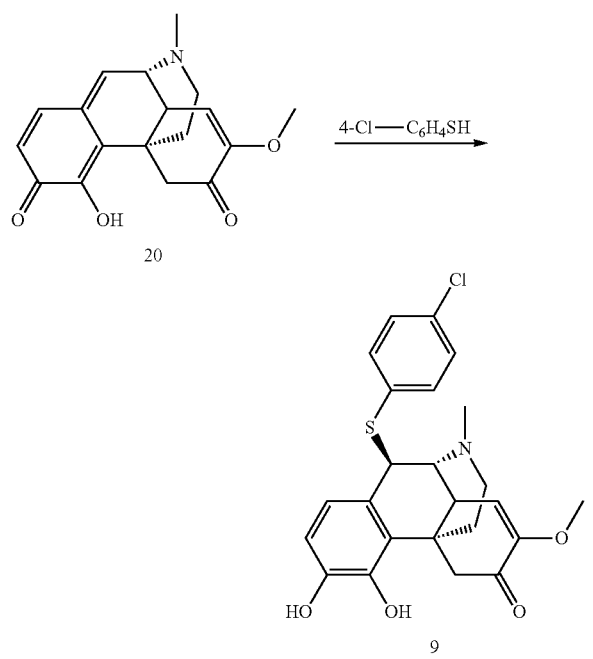

9

Compound 20 (1.0 g, 3.19 mmol) and dichloromethane (30 mL) are added in a 50 mL pear-shaped flask. The mixture is stirred in an ice bath. p-Chlorobenzene mercaptan (0.51 g, 3.51 mmol, 1.1 equiv.) is added. The stirring is continued after the addition. The solution is allowed to warm up to room temperature and stirred until TLC shows the disappearance of the starting material. To work up, the reaction solution is evaporated to dryness, and the residue is purified on a column to give a white solid (1.32 g, 90%).

M.p. 230-231° C. (dec.); $[\alpha]_D^{27}$=−10.6 (c 0.40, DMSO); $^1$H NMR (DMSO-d$_6$, 400 MHz): δ 9.48 (1H, s), 8.18 (1H, s), 7.70 (2H, d, J=8.4 Hz), 7.48 (2H, d, J=8.4 Hz), 7.00 (1H, d, J=8.0 Hz), 6.67 (1H, d, J=8.4 Hz), 6.24 (1H, d, J=2.0 Hz), 4.56 (1H, s), 4.18 (1H, d, J=15.2 Hz), 3.52 (3H, s), 3.14 (1H, d, J=2.1 Hz), 3.00 (1H, s), 2.40 (1H, d, J=15.6 Hz), 2.26-2.35 (1H, m), 2.00 (3H, s), 1.83 (1H, dt, J=5.6, 11.2 Hz), 1.65-1.76 (2H, m); $^{13}$C NMR (DMSO-d$_6$, 100 MHz): δ 192.4, 149.5, 144.1, 144.0, 134.6, 133.8, 132.3, 129.1, 127.9, 123.8, 120.4, 117.7, 113.3, 59.9, 53.9, 48.4, 45.9, 44.7, 43.6, 41.8, 39.7, 35.4; IR (KBr): $v_{max}$ 3350.8, 2940.3, 1665.9, 1620.6, 1490.8, 1474.9, 1290.9, 1203.1, 1152.0, 1093.0, 815.3 cm$^{-1}$; HRMS (MALDI, m/z) $C_{24}H_{25}NO_4SCl$ (M+H$^+$) calculated: 458.1187, detected: 458.1195.

Example 10

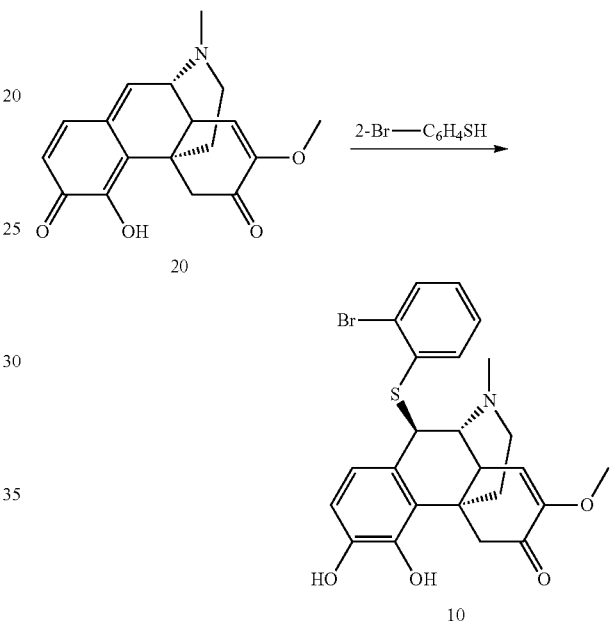

10

Compound 20 (1.0 g, 3.19 mmol) and dichloromethane (30 mL) are added in a 50 mL pear-shaped flask. The mixture is stirred in an ice bath. A solution of 2-bromobenzene mercaptan (0.42 mL, 3.51 mmol, 1.1 equiv.) in dichloromethane (15 mL) is added dropwise. The stirring is continued after the addition. The solution is allowed to warm up to room temperature and stirred until TLC shows the disappearance of the starting material. To work up, the reaction solution is evaporated to dryness, and the residue is purified on a column to give a white solid (1.52 g, 95%).

M.p. 204-205° C. (dec.); $[\alpha]_D^{27}$=0.4 (c 0.50, DMSO); $^1$H NMR (DMSO-d$_6$, 400 MHz): δ 9.53 (1H, s), 8.22 (1H, s), 7.93 (1H, dd, J=1.2, 8.0 Hz), 7.75 (1H, dd, J=1.2, 8.0 Hz), 7.47 (1H, dt, J=1.2, 7.6 Hz), 7.29 (1H, dt, J=1.2, 8.0 Hz), 7.08 (1H, d, J=8.4 Hz), 6.69 (1H, d, J=8.4 Hz), 6.42 (1H, d, J=2.0 Hz), 4.66 (1H, s), 4.19 (1H, d, J=15.2 Hz), 3.54 (3H, s), 3.06 (1H, d, J=2.8 Hz), 3.03 (1H, s), 2.41 (1H, d, J=15.6 Hz), 2.28-2.36 (1H, m), 1.96 (3H, s), 1.85 (1H, dt, J=4.2, 10.0 Hz), 1.67-1.78 (2H, m); $^{13}$C NMR (DMSO-d$_6$, 100 MHz): δ 192.4, 149.5, 144.3, 144.1, 135.9, 134.1, 133.2, 129.3, 128.4, 127.4, 126.6, 124.1, 120.3, 117.8, 113.4, 59.7, 54.1, 48.5, 45.9, 44.5, 42.8, 41.7, 39.8, 35.3; IR (KBr): $v_{max}$ 3467.2, 2948.6, 1677.2, 1617.6, 1486.7, 1447.7, 1378.9, 1281.5, 1199.7, 1146.9, 1099.5, 819.1, 761.5 cm$^{-1}$; HRMS (ESI, m/z) $C_{24}H_{25}NO_4SBr$ (M+H$^+$) calculated: 502.0682, detected: 502.0695.

Example 11

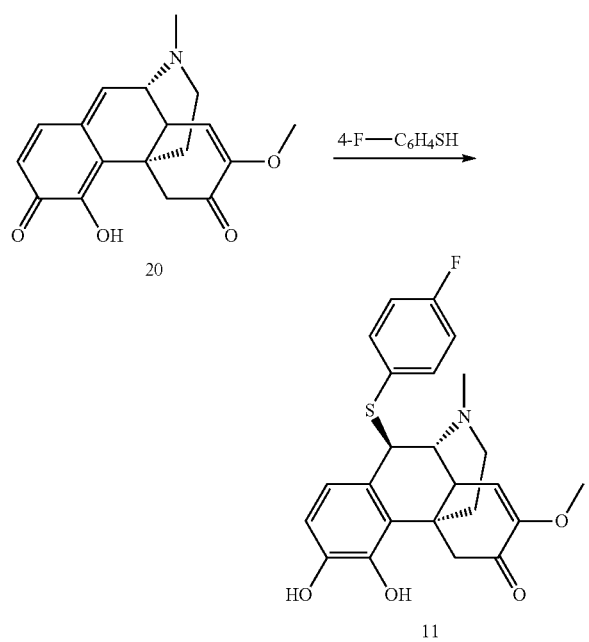

Compound 20 (1.0 g, 3.19 mmol) and dichloromethane (30 mL) are added in a 50 mL pear-shaped flask. The mixture is stirred in an ice bath. p-Fluorobenzene mercaptan (0.45 g, 3.51 mmol, 1.1 equiv.) is added. The stirring is continued after the addition. The solution is allowed to warm up to room temperature and stirred until TLC shows the disappearance of the starting material. To work up, the reaction solution is evaporated to dryness, and the residue is purified on a column to give a yellow solid (1.22 g, 87%).

M.p. 220-221° C. (dec.); $[\alpha]_D^{27}=-11.1$ (c 0.60, DMSO); $^1$H NMR (DMSO-d$_6$, 400 MHz): δ 9.48 (1H, s), 8.19 (1H, s), 7.72-7.79 (2H, m), 7.28 (2H, t, J=8.8 Hz), 7.04 (1H, d, J=8.0 Hz), 6.67 (1H, d, J=8.4 Hz), 6.27 (1H, d, J=2.0 Hz), 4.46 (1H, s), 4.18 (1H, d, J=15.2 Hz), 3.52 (3H, s), 3.14 (1H, d, J=3.2 Hz), 3.00 (1H, s), 2.39 (1H, d, J=15.2 Hz), 2.25-2.35 (1H, m), 1.91 (3H, s), 1.80 (1H, dt, J=4.4, 10.8 Hz), 1.65-1.75 (2H, m); $^{13}$C NMR (DMSO-d$_6$, 100 MHz): δ 192.4, 161.8 (d, J=244.1 Hz), 149.5, 144.1, 144.0, 135.3 (d, J=8.4 Hz), 131.0 (d, J=3.0 Hz), 128.0, 123.8, 120.4, 117.8, 116.2 (d, J=21.7 Hz), 113.3, 59.6, 53.9, 48.4, 45.9, 44.8, 44.1, 41.6, 39.8, 35.5; $^{19}$F NMR (CHCl$_3$/MeOH=1:1, 300 MHz): −113.89; IR (KBr): $v_{max}$ 3350.0, 2948.4, 2836.5, 1666.2, 1615.2, 1589.9, 1489.4, 1291.7, 1200.2, 1176.0, 1092.6, 904.8, 814.0 cm$^{-1}$; HRMS (ESI, m/z) C$_{24}$H$_{25}$NO$_4$SF (M+H$^+$) calculated: 442.1483, detected: 442.1496.

Example 12

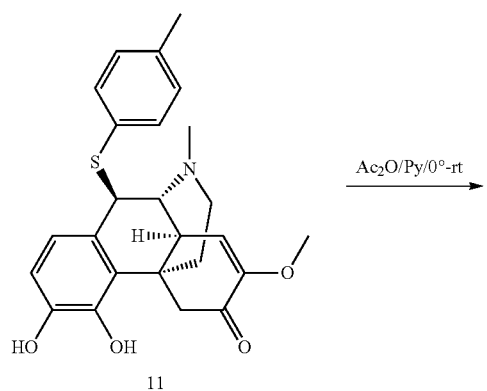

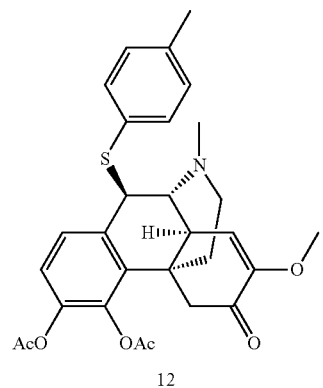

Compound 1 (398 mg, 0.91 mmol) is dissolved in pyridine (4 mL). The mixture is stirred in an ice bath, and acetic anhydride (172 μL, 1.82 mmol, 2.0 equiv.) is added dropwise. The solution is allowed to warm up to room temperature and the reaction is continued until TLC shows the disappearance of the starting material. To work up, the reaction solution is evaporated to dryness, and the residue is purified on a column to give a white solid (427 mg, 90%).

M.p. 206-207° C.; $[\alpha]_D^{26}=-42.9$ (c 0.40, CHCl$_3$); $^1$H NMR (CDCl$_3$, 400 MHz): δ 7.67 (1H, d, J=8.8 Hz), 7.50 (2H, d, J=8.0 Hz), 7.16-7.24 (3H, m), 6.28 (1H, d, J=2.0 Hz), 4.41 (1H, s), 3.77 (1H, d, J=16.0 Hz), 3.64 (3H, s), 3.43 (1H, d, J=3.2 Hz), 3.08 (1H, s), 2.51 (1H, d, J=16.0 Hz), 2.38 (3H, s), 2.37 (3H, s), 2.32-2.37 (1H, m), 2.22 (3H, s), 2.04 (3H, s), 1.94 (1H, dt, J=2.8, 12.0 Hz), 1.84 (1H, dt, J=4.4, 12.4 Hz), 1.56 (1H, d, J=12.0 Hz); $^{13}$C NMR (CDCl$_3$, 100 MHz): δ 191.7, 168.0, 167.5, 150.9, 142.2, 141.0, 138.5, 136.3, 133.2, 132.0, 130.9, 130.2, 128.0, 121.8, 116.8, 60.7, 54.9, 50.2, 46.0, 45.7, 44.3, 42.1, 40.8, 37.5, 21.2, 21.0, 20.9; IR (KBr): $v_{max}$ 3418.8, 2929.8, 1774.5, 1689.6, 1622.1, 1472.0, 1372.9, 1262.9, 1203.3, 1177.8, 1144.3, 1088.3, 1013.3, 929.7, 812.0, 500.0 cm$^{-1}$; MS (MALDI, m/z): 522.1 (M+H)$^+$, C$_{29}$H$_{31}$NO$_6$S elemental analysis, calculated: C, 66.77; H, 5.99; N, 2.69. detected: C, 66.86; H, 6.02; N, 2.79.

Example 13

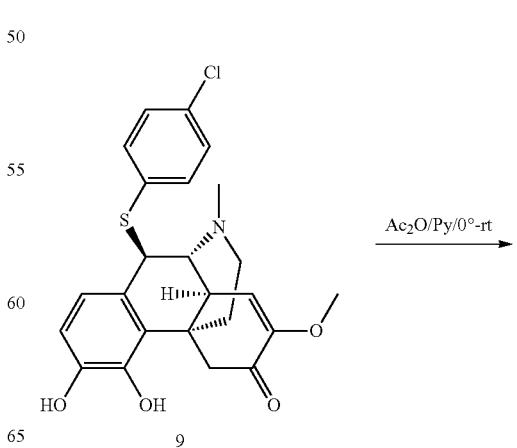

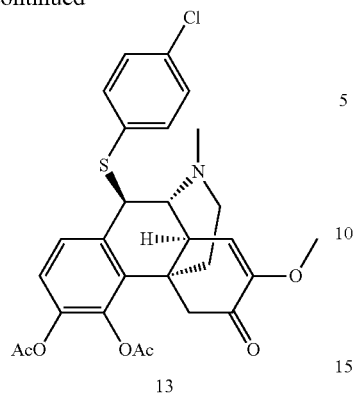

13

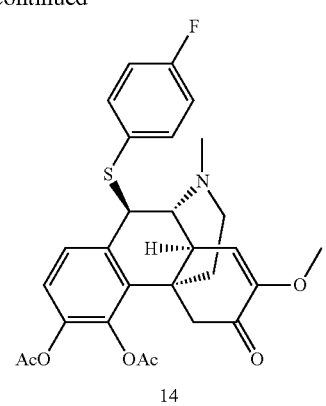

14

Compound 9 (417 mg, 0.91 mmol) is dissolved in pyridine (4 mL). The mixture is stirred in an ice bath, and acetic anhydride (172 µL, 1.82 mmol, 2.0 equiv.) is added dropwise. The solution is allowed to warm up to room temperature and the reaction is continued until TLC shows the disappearance of the starting material. To work up, the reaction solution is evaporated to dryness, and the residue is purified on a column to give a white solid (431 mg, 87%).

M.p. 176-178° C.; $[\alpha]_D^{26}=-60.4$ (c 0.50, CHCl$_3$); $^1$H NMR (CDCl$_3$, 400 MHz): δ 7.62 (1H, d, J=8.8 Hz), 7.54 (2H, d, J=8.4 Hz), 7.39 (2H, d, J=8.4 Hz), 7.20 (1H, d, J=8.8 Hz), 6.20 (1H, d, J=2.0 Hz), 4.44 (1H, s), 3.77 (1H, d, J=15.6 Hz), 3.63 (3H, s), 3.41 (1H, d, J=3.2 Hz), 3.10 (1H, s), 2.51 (1H, d, J=16.0 Hz), 2.37-2.44 (1H, m), 2.38 (3H, s), 2.22 (3H, s), 2.10 (3H, s), 1.96 (1H, dt, J=2.8, 12.4 Hz), 1.86 (1H, dt, J=4.4, 12.0 Hz), 1.57 (1H, d, J=12.0 Hz); $^{13}$C NMR (CDCl$_3$, 100 MHz): δ 191.6, 167.9, 167.5, 151.0, 142.3, 141.0, 135.7, 134.7, 134.1, 133.9, 130.9, 129.6, 127.9, 121.9, 116.3, 60.9, 54.9, 50.1, 45.8, 45.5, 44.4, 42.1, 40.7, 37.3, 20.9, 20.8; IR (KBr): $v_{max}$ 3448.4, 2932.9, 1774.5, 1693.0, 1624.7, 1475.0, 1438.9, 1370.6, 1263.6, 1202.0, 1171.1, 1145.8, 1093.1, 1011.7, 931.2, 818.3 cm$^{-1}$; MS (ESI, m/z): 541.9 (M+H)$^+$, C$_{28}$H$_{28}$ClNO$_6$S elemental analysis, calculated: C, 62.04; H, 5.21; N, 2.58. detected: C, 61.75; H, 5.33; N, 2.73.

Compound 11 (402 mg, 0.91 mmol) is dissolved in pyridine (4 mL). The mixture is stirred in an ice bath, and acetic anhydride (172 µL, 1.82 mmol, 2.0 equiv.) is added dropwise. The solution is allowed to warm up to room temperature and the reaction is continued until TLC shows the disappearance of the starting material. To work up, the reaction solution is evaporated to dryness, and the residue is purified on a column to give a pale yellow solid (406 mg, 85%).

M.p. 185-187° C.; $[\alpha]_D^{26}=-53.6$ (c 0.50, CHCl$_3$); $^1$H NMR (CDCl$_3$, 400 MHz): δ 7.65 (1H, d, J=8.4 Hz), 7.57-7.63 (2H, m), 7.20 (1H, d, J=8.4 Hz), 7.07-7.17 (2H, m), 6.24 (1H, d, J=2.0 Hz), 4.36 (1H, s), 3.77 (1H, d, J=16.0 Hz), 3.63 (3H, s), 3.42 (1H, d, J=3.2 Hz), 3.10 (1H, s), 2.51 (1H, d, J=16.0 Hz), 2.36-2.43 (1H, m), 2.38 (3H, s), 2.22 (3H, s), 2.02 (3H, s), 1.93 (1H, dt, J=2.8, 12.4 Hz), 1.85 (1H, dt, J=4.4, 12.4 Hz), 1.57 (1H, d, J=12.4 Hz); $^{19}$F NMR (CDCl$_3$, 400 MHz): −110.93; $^{13}$C NMR (CDCl$_3$, 100 MHz): δ 191.6, 167.9, 167.5, 162.8 (d, J=248 Hz), 151.0, 142.2, 141.0, 135.8, 135.5 (d, J=8.2 Hz), 130.9, 130.6 (d, J=3.4 Hz), 127.9, 121.8, 116.6 (d, J=21.8 Hz), 116.4, 60.7, 54.9, 50.1, 45.8, 45.5, 44.8, 41.9, 40.7, 37.3, 20.9, 20.8; IR (KBr): $v_{max}$ 3435.1, 2928.5, 1774.2, 1694.0, 1624.1, 1587.8, 1489.2, 1474.4, 1371.7, 1263.7, 1202.7, 1173.2, 1145.2, 1089.1, 1012.8, 931.1, 836.6, 816.8 cm$^{-1}$; HRMS (MALDI, m/z) C$_{28}$H$_{29}$NO$_6$SF (M+H$^+$) calculated: 526.1694, detected: 526.1701.

Example 14

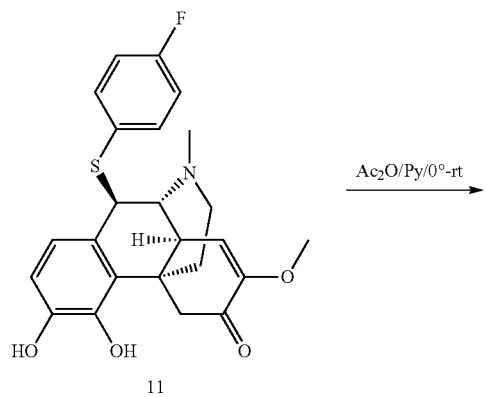

11

Ac$_2$O/Py/0°-rt →

Example 15

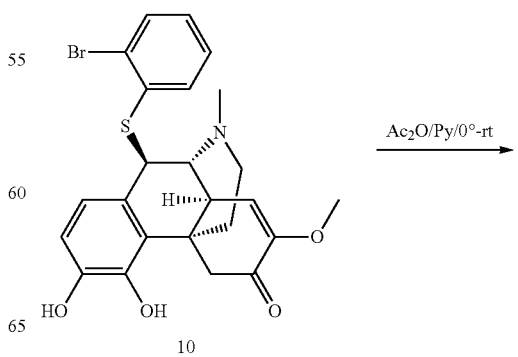

10

Ac$_2$O/Py/0°-rt →

51

-continued

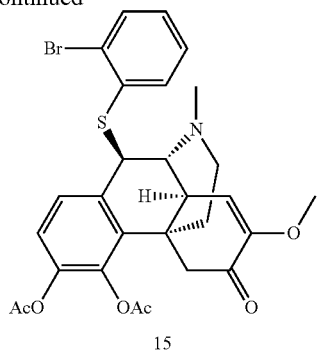

15

Compound 10 (457 mg, 0.91 mmol) is dissolved in pyridine (4 mL). The mixture is stirred in an ice bath, and acetic anhydride (172 μL, 1.82 mmol, 2.0 equiv.) is added dropwise. The solution is allowed to warm up to room temperature and the reaction is continued until TLC shows the disappearance of the starting material. To work up, the reaction solution is evaporated to dryness, and the residue is purified on a column to give a pale yellow solid (480 mg, 90%).

M.p. 196-198° C. (dec.); $[\alpha]_D^{26}=-11.8$ (c 0.50, CHCl$_3$); $^1$H NMR (CDCl$_3$, 400 MHz): δ 7.78 (1H, d, J=8.8 Hz), 7.67-7.76 (2H, m), 7.39 (1H, dt, J=1.2, 7.6 Hz), 7.18-7.25 (2H, m), 6.45 (1H, d, J=2.0 Hz), 4.62 (1H, s), 3.78 (1H, d, J=16.0 Hz), 3.66 (3H, s), 3.32 (1H, d, J=12.8 Hz), 3.10 (1H, s), 2.52 (1H, d, J=16.0 Hz), 2.35-2.43 (1H, m), 2.38 (3H, s), 2.22 (3H, s), 2.01 (3H, s), 1.93-2.00 (1H, m), 1.86 (1H, dt, J=4.4, 12.4 Hz), 1.53-1.58 (1H, m); IR (KBr): $v_{max}$ 3435.3, 2932.1, 1774.6, 1693.6, 1618.6, 1473.0, 1442.5, 1420.9, 1369.9, 1263.4, 1200.6, 1174.8, 1143.9, 1017.1, 928.8, 877.9, 751.5 cm$^{-1}$; MS (MALDI, m/z): 586.3 (M+H)$^+$, C$_{28}$H$_{28}$BrNO$_6$S elemental analysis, calculated: C, 57.34; H, 4.81; N, 2.39. detected: C, 57.09; H, 4.79; N, 2.25.

Example 16

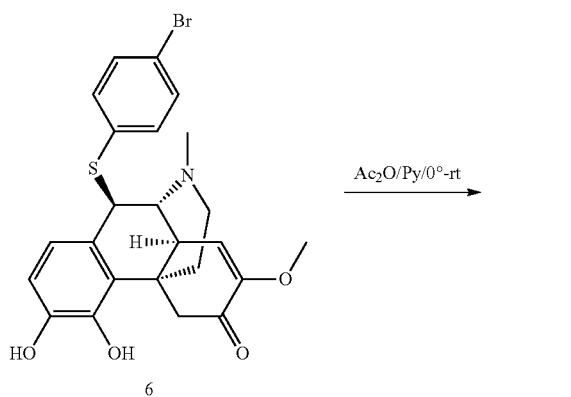

Compound 6 (457 mg, 0.91 mmol) is dissolved in pyridine (4 mL). The mixture is stirred in an ice bath, and acetic anhydride (172 μL, 1.82 mmol, 2.0 equiv.) is added dropwise. The solution is allowed to warm up to room temperature and the reaction is continued until TLC shows the disappearance of the starting material. To work up, the reaction solution is evaporated to dryness, and the residue is purified on a column to give a white solid (464 mg, 87%).

M.p. 122-124° C.; $[\alpha]_D^{26}=-46.8$ (c 0.40, CHCl$_3$); $^1$H NMR (CDCl$_3$, 400 MHz): δ 7.61 (1H, d, J=8.8 Hz), 7.54 (2H, d, J=8.4 Hz), 7.46 (2H, d, J=8.4 Hz), 7.20 (1H, d, J=8.8 Hz), 6.19 (1H, d, J=2.0 Hz), 4.45 (1H, s), 3.77 (1H, d, J=15.6 Hz), 3.63 (3H, s), 3.41 (1H, d, J=3.2 Hz), 3.10 (1H, s), 2.51 (1H, d, J=15.6 Hz), 2.38-2.45 (1H, m), 2.38 (3H, s), 2.22 (3H, s), 2.11 (3H, s), 1.96 (1H, dt, J=2.4, 12.0 Hz), 1.86 (1H, dt, J=4.4, 12.4 Hz), 1.57 (1H, d, J=12.4 Hz); $^{13}$C NMR (CDCl$_3$, 100 MHz): δ 191.5, 167.9, 167.5, 151.0, 142.3, 141.0, 135.6, 134.7, 134.0, 132.5, 130.9, 127.9, 122.3, 121.9, 116.2, 60.9, 54.8, 50.0, 45.8, 45.4, 44.2, 42.1, 40.7, 37.2, 20.9, 20.8; IR (KBr): $v_{max}$ 3400.7, 2931.5, 1774.0, 1692.0, 1624.7, 1473.6, 1370.4, 1263.6, 1201.5, 1170.3, 1145.0, 1088.6, 1007.2, 930.8, 816.6 cm$^{-1}$; HRMS (MALDI, m/z) C$_{28}$H$_{29}$NO$_6$SBr (M+H$^+$) calculated: 586.0894, detected: 586.0908.

Example 17

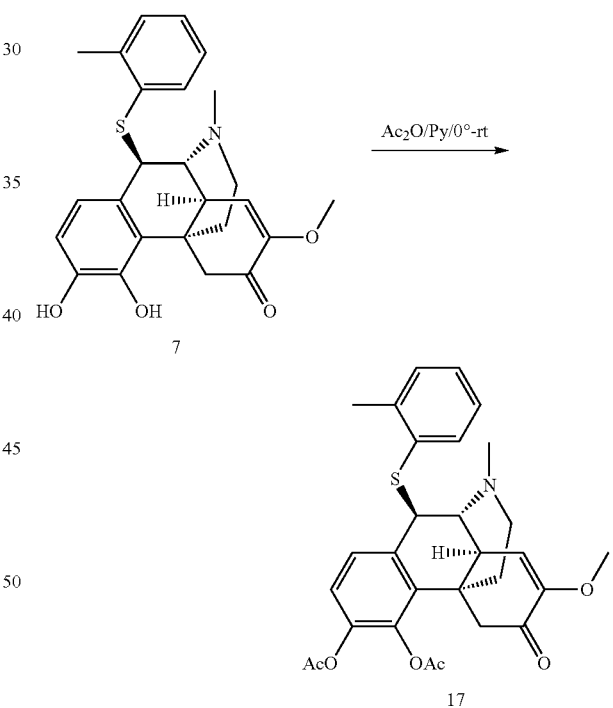

Compound 7 (398 mg, 0.91 mmol) is dissolved in pyridine (4 mL). The mixture is stirred in an ice bath, and acetic anhydride (172 μL, 1.82 mmol, 2.0 equiv.) is added dropwise. The solution is allowed to warm up to room temperature and the reaction is continued until TLC shows the disappearance of the starting material. To work up, the reaction solution is evaporated to dryness, and the residue is purified on a column to give a white solid (437 mg, 92%).

M.p. 188-190° C.; $[\alpha]_D^{26}=-38.9$ (c 0.50, CHCl$_3$); $^1$H NMR (CDCl$_3$, 400 MHz): δ 7.66 (1H, d, J=9.2 Hz), 7.59-7.64 (1H, m), 7.23-7.33 (3H, m), 7.20 (1H, d, J=8.4 Hz), 6.36 (1H, d, J=2.0 Hz), 4.41 (1H, s), 3.78 (1H, d, J=16.0 Hz), 3.65 (3H, s), 3.38 (1H, d, J=3.2 Hz), 3.10 (1H, s), 2.56 (3H, s), 2.52 (1H, d, J=16.0 Hz), 2.33-2.42 (1H, m), 2.38 (3H, s), 2.22 (3H, s), 2.01 (3H, s), 1.96 (1H, dt, J=2.8, 12.4 Hz), 1.85 (1H, dt, J=4.4, 12.4 Hz), 1.57 (1H, d, J=12.4 Hz); $^{13}$C NMR (CDCl$_3$, 100 MHz): δ 191.6, 167.9, 167.5, 150.9, 142.1, 141.0, 140.2, 136.1, 134.3, 133.5, 131.0, 130.9, 128.3, 127.7, 126.7, 121.8, 116.7, 60.6, 54.8, 50.2, 45.8, 45.5, 42.8, 41.9, 40.7, 37.3, 20.9, 20.9, 20.8; IR (KBr): $v_{max}$ 3444.8, 2919.7, 1774.3, 1693.2, 1621.3, 1470.8, 1373.3, 1262.6, 1201.8, 1144.1, 1013.3, 930.7 cm$^{-1}$; MS (ESI, m/z): 522.0 (M+H)$^+$, C$_{29}$H$_{31}$NO$_6$S elemental analysis, calculated: C, 66.77; H, 5.99; N, 2.69. detected: C, 66.78; H, 6.05; N, 2.81.

Example 18

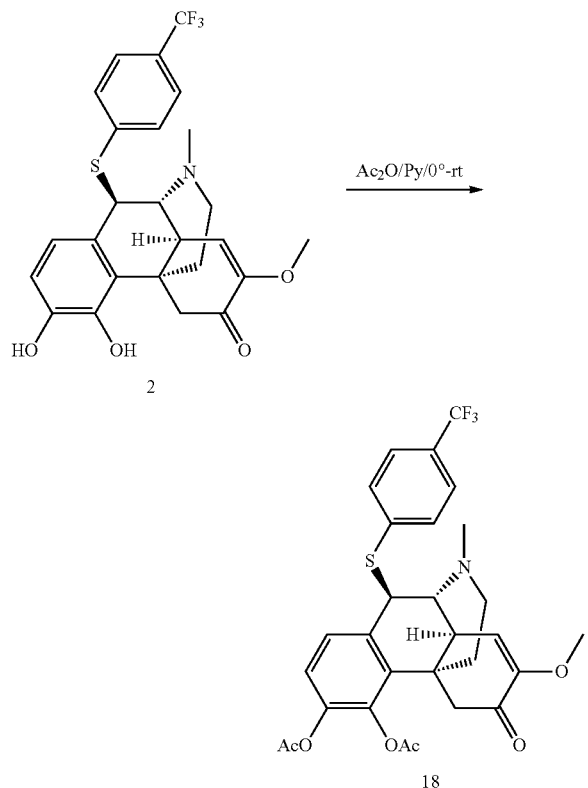

Compound 2 (447 mg, 0.91 mmol) is dissolved in pyridine (4 mL). The mixture is stirred in an ice bath, and acetic anhydride (172 μL, 1.82 mmol, 2.0 equiv.) is added dropwise. The solution is allowed to warm up to room temperature and the reaction is continued until TLC shows the disappearance of the starting material. To work up, the reaction solution is evaporated to dryness, and the residue is purified on a column to give a white solid (508 mg, 97%).

M.p. 111-113° C.; $[\alpha]_D^{26}$=−44.1 (c 0.50, CHCl$_3$); $^1$H NMR (CDCl$_3$, 400 MHz): δ 7.62-7.69 (4H, m), 7.57 (1H, d, J=8.8 Hz), 7.20 (1H, d, J=8.4 Hz), 6.16 (1H, d, J=2.0 Hz), 4.62 (1H, s), 3.78 (1H, d, J=16.0 Hz), 3.64 (3H, s), 3.43 (1H, d, J=3. Hz), 3.12 (1H, s), 2.53 (1H, d, J=16.0 Hz), 2.40-2.47 (1H, m), 2.39 (3H, s), 2.23 (3H, s), 2.22 (3H, s), 2.02 (1H, dt, J=2.8, 12.4 Hz), 1.87 (1H, dt, J=4.4, 12.4 Hz), 1.57 (1H, d, J=12.8 Hz); $^{19}$F NMR (CDCl$_3$, 400 MHz): δ-61.40; $^{13}$C NMR (CDCl$_3$, 100 MHz): δ 191.5, 167.9, 167.5, 151.1, 142.4, 141.1, 140.9, 135.3, 130.9, 129.6 (q, J=42.7 Hz), 127.9, 126.2 (q, J=3.6 Hz), 125.2, 122.5, 122.0, 116.0, 61.3, 54.8, 50.0, 45.8, 45.2, 43.5, 42.3, 40.7, 37.1, 20.9, 20.8; IR (KBr): $v_{max}$ 3521.5, 2934.7, 1776.8, 1693.3, 1626.0, 1604.4, 1475.9, 1372.6, 1326.3, 1263.4, 1202.5, 1169.8, 1121.4, 1061.9, 1013.2, 946.1, 819.9 cm$^{-1}$; HRMS (MALDI, m/z) C$_{29}$H$_{29}$NO$_6$SF$_3$ (M+H$^+$) calculated: 576.1662, detected: 576.1681.

Example 19

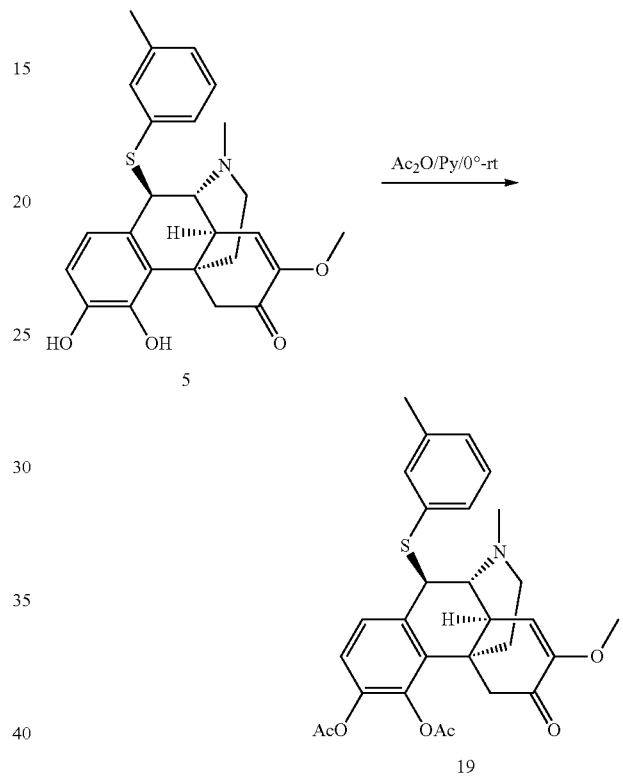

Compound 5 (398 mg, 0.91 mmol) is dissolved in pyridine (4 mL). The mixture is stirred in an ice bath, and acetic anhydride (172 μL, 1.82 mmol, 2.0 equiv.) is added dropwise. The solution is allowed to warm up to room temperature and the reaction is continued until TLC shows the disappearance of the starting material. To work up, the reaction solution is evaporated to dryness, and the residue is purified on a column to give a white solid (394 mg, 83%).

M.p. 166-168° C. (dec.); $[\alpha]_D^{26}$=−28.8 (c 0.50, CHCl$_3$); $^1$H NMR (CDCl$_3$, 400 MHz): δ 7.66 (1H, d, J=8.4 Hz), 7.40 (2H, d, J=8.0 Hz), 7.26-7.32 (1H, m), 7.20 (1H, d, J=8.8 Hz), 7.16 (1H, d, J=7.6 Hz), 6.27 (1H, d, J=2.0 Hz), 4.48 (1H, s), 3.77 (1H, d, J=16.0 Hz), 3.65 (3H, s), 3.44 (1H, d, J=2.8 Hz), 3.10 (1H, s), 2.51 (1H, d, J=15.6 Hz), 2.38-2.45 (1H, m), 2.39 (3H, s), 2.38 (3H, s), 2.22 (3H, s), 2.08 (3H, s), 1.97 (1H, dt, J=2.8, 12.4 Hz), 1.86 (1H, dt, J=4.4, 12.4 Hz), 1.57 (1H, d, J=12.4 Hz); $^{13}$C NMR (CDCl$_3$, 100 MHz): δ 191.6, 167.9, 167.5, 150.9, 142.1, 140.9, 139.3, 136.0, 135.2, 133.1, 130.8, 129.5, 129.2, 128.9, 128.0, 121.8, 116.6, 60.7, 54.9, 50.1, 45.9, 45.5, 43.9, 41.9, 40.7, 37.3, 21.3, 20.9, 20.8; IR (KBr): $v_{max}$ 3428.0, 2930.0, 1771.0, 1695.6, 1629.2, 1476.0, 1370.5, 1262.9, 1203.2, 1174.5, 1144.4, 1012.8, 879.0 cm$^{-1}$; HRMS (MALDI, m/z) C$_{29}$H$_{32}$NO$_6$S (M+H$^+$) calculated: 522.1945, detected: 522.1850.

Example 20

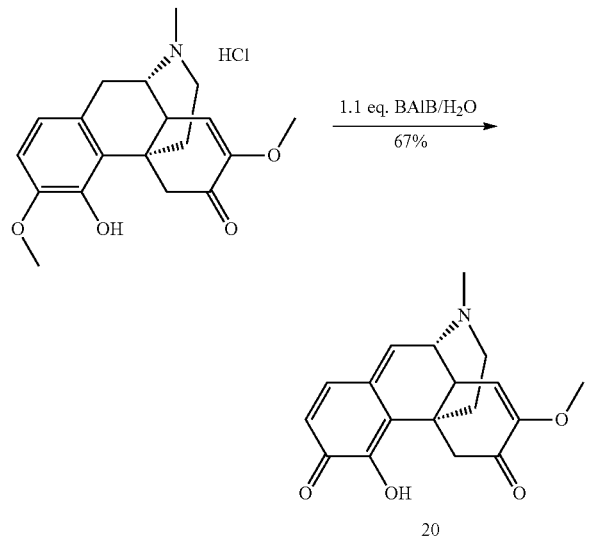

Sinomenine HCl salt (21 g, 57.4 mmol, 1 equiv.) is dissolved in distilled water (420 mL) in a 1 L pear-shaped flask. The mixture is stirred at room temperature, and iodobenzene diacetate (21 g, 65.2 mmol, 1.1 equiv.) is added. After addition, the reaction is stirred at room temperature for 1 hour. The reaction solution turned reddish brown. To work up, the reaction solution is adjusted to alkaline with solid sodium bicarbonate. The solution is then extracted with dichloromethane. The dichloromethane extract is washed with water, saturated NaCl, and dried with anhydrous $Na_2SO_4$. The solution is filtered, dried, and the residue is purified on a column, using dichloromethane/acetone (1:1) as a mobile phase, to obtain a product (12 g, 67%).

M.p. 187-188° C. (dec.); $[\alpha]_D^{25}$=563.3 (c 0.80, CHCl$_3$); $^1$H NMR (CDCl$_3$, 400 MHz): δ 7.04 (1H, d, J=9.6 Hz), 6.56 (1H, d, J=5.6 Hz), 6.44 (1H, d, J=9.2 Hz), 5.28 (1H, d, J=2.0 Hz), 4.06 (1H, d, J=16.0 Hz), 3.73 (1H, dd, J=2.8, J=5.6 Hz), 3.48 (3H, s), 2.96 (1H, brs), 2.58-2.65 (1H, m), 2.42 (3H, s), 2.37 (1H, d, J=16.4 Hz), 2.05 (1H, td, J=3.6, 12.8 Hz), 1.89-1.95 (1H, m), 1.84 (1H, td, J=5.2, 12.8 Hz); $^{13}$C NMR (CDCl$_3$, 100 MHz): δ 192.5, 181.1, 152.4, 147.0, 141.0, 140.3, 139.1, 124.8, 116.9, 114.8, 58.0, 54.9, 48.1, 46.5, 45.7, 43.0, 40.2, 35.7; IR (KBr): 2946.3, 2829.9, 2254.0, 1684.7, 1627.4, 1466.7, 1363.2, 1199.8, 1150.1, 727.0 cm$^{-1}$; HRMS (ESI, m/z) $C_{18}H_{20}N_1O_4$ (M+H$^+$) calculated: 314.1387, detected: 314.1399.

Example 21

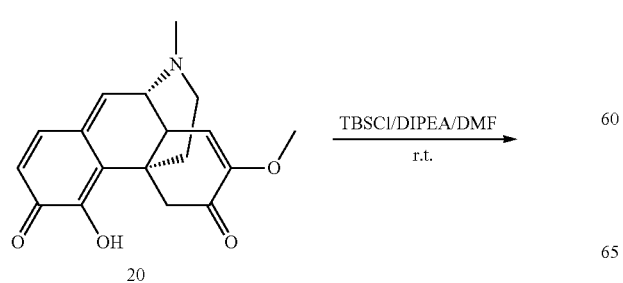

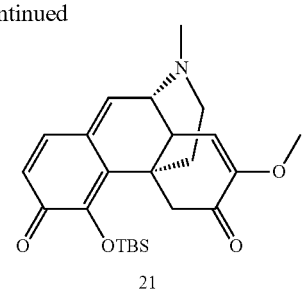

Compound 20 (4.0 g, 12.8 mmol, 1 equiv.) is dissolved in N,N-dimethyl formamide (50 mL) in a 250 mL pear-shaped flask. To the mixture is added tert-butyl-dimethylsilyl chloride (TBSCl) (2.9 g, 19.3 mmol, 1.5 equiv.). After the addition, the reaction is cooled in an ice bath. Then, diisopropylethyl amine (3.2 mL, 19.4 mmol, 1.5 equiv.) is slowly added. The stirring is continued after the addition. The solution is allowed to warm up to room temperature, and reaction is continued until TLC shows the disappearance of the starting material. Water is then added slowly to the reaction mixture (about 100 mL) and a large amount of yellow solid is precipitated, which are collected by suction filtration and washed with water. The solid is dissolved in dichloromethane and dried with anhydrous sodium sulfate. The solution is filtered and evaporated to give the product (5.0 g, 92%).

$[\alpha]_D^{26}$=387.6 (c 1.18, CHCl$_3$); $^1$H NMR (CDCl$_3$, 300 MHz): δ 6.94 (1H, d, J=9.3), 6.47 (1H, d, J=5.7), 6.30 (1H, d, J=9.6), 5.23 (1H, s), 4.22 (1H, d, J=16.2), 3.65 (1H, dd, J=5.7, 2.7), 3.47 (3H, s), 2.89 (1H, brs), 2.52-2.65 (1H, m), 2.42 (3H, s), 2.30 (1H, d, J=15.9), 2.12 (1H, td, J=12.6, 3), 1.98 (1H, d, J=12.9), 1.80 (1H, td, J=4.8, 12.6), 1.01 (9H, s), 0.34 (3H, s), 0.21 (3H, s); $^{13}$C NMR (CDCl$_3$, 75 MHz): δ 191.9, 181.5, 152.2, 148.2, 140.1, 139.5, 138.4, 126.6, 122.9, 114.9, 57.8, 54.8, 47.6, 46.6, 45.9, 43.0, 40.4, 35.8, 26.9, 19.7, −1.9, −2.2; IR (KBr): 3063.8, 2953.5, 2934.7, 2904.5, 2856.9, 2798.7, 1693.6, 1630.0, 1560.0, 1373.0, 1249.9, 1200.5, 1150.0, 838.3, 807.0, 784.0 cm$^{-1}$; HRMS (ESI, m/z) $C_{24}H_{34}N_1O_4Si_1$ (M+H$^+$) calculated: 428.22516, detected: 428.22532.

Example 22

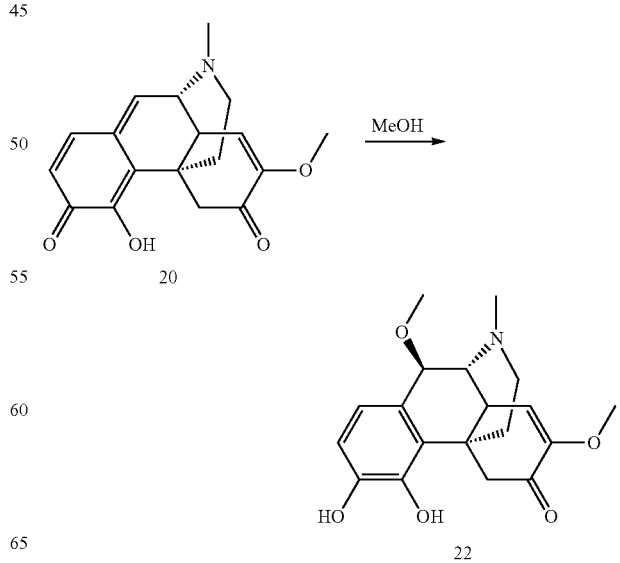

Compound 20 (2.0 g, 6.38 mmol) and methanol (20 mL) are added to a 100 mL pear-shaped flask. After the addition, the reaction is stirred at room temperature until TLC shows the disappearance of the starting material. To work up, the solution is evaporated to dryness, and the residue is purified on a column, using dichloromethane/methanol (30/1) as a mobile phase, to obtain the product (1.4 g, 64%).

M.p. 159-160° C. (dec.); $[\alpha]_D^{25}=-56.8$ (c 0.26, CHCl$_3$—CH$_3$OH=10:1); $^1$H NMR (DMSO-d$_6$, 400 MHz): δ 9.38 (1H, s), 8.05 (1H, s), 6.63 (2H, s), 5.76 (1H, d, J=2.0 Hz), 4.14 (1H, d, J=15.2 Hz), 4.06 (1H, s), 3.45 (3H, s), 3.30 (3H, s), 3.21-3.25 (1H, m), 2.90 (1H, brs), 2.40 (3H, s), 2.36 (1H, d, J=15.6 Hz), 1.75-1.85 (1H, m), 1.67-1.73 (2H, m); $^{13}$C NMR (DMSO-d$_6$, 100 MHz): δ 192.4, 149.4, 143.6, 144.1, 130.4, 122.7, 120.5, 119.0, 113.1, 72.1, 57.2, 56.9, 53.8, 48.6, 46.3, 44.1, 42.1, 40.2, 35.1; IR (KBr): 3284.2, 2941.2, 2811.4, 1674.4, 1629.6, 1479.1, 1363.6, 1288.5, 1200.2, 1150.5, 1087.3, 1073.9, 1007.0, 919.5, 828.6 cm$^{-1}$; HRMS (ESI, m/z) C$_{19}$H$_{24}$N$_1$O$_5$ (M+H$^+$) calculated: 346.1649, detected: 346.1665.

Example 23

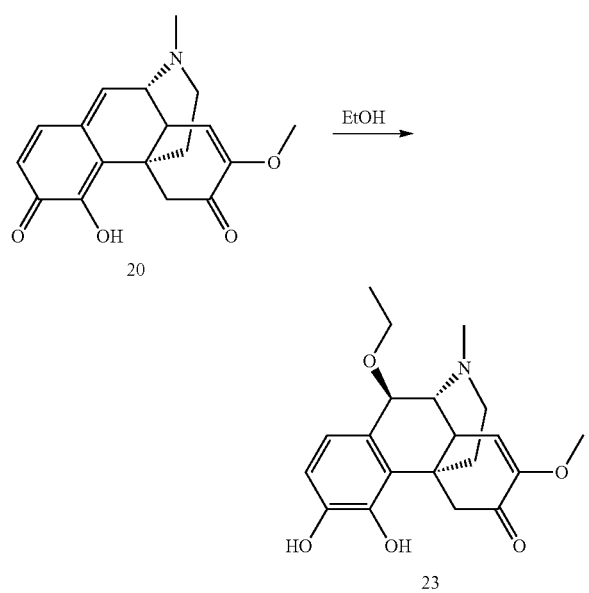

Compound 20 (0.6 g, 1.91 mmol) and ethanol (20 mL) are added to a 100 mL pear-shaped flask. After the addition, the reaction is stirred at room temperature until TLC shows the disappearance of the starting material. To work up, the solution is evaporated to dryness, and the residue is purified on a column, using dichloromethane/methanol (30/1) as a mobile phase, to obtain the product (0.3 g, 44%).

M.p. 191-193° C. (dec.); $[\alpha]_D^{26}=-28.3$ (c 0.40, CHCl$_3$—CH$_3$OH=10:1); $^1$H NMR (DMSO-d$_6$, 300 MHz): δ 9.41 (1H, brs), 8.09 (1H, s), 6.64 (1H, d, J=8.1 Hz), 6.60 (1H, d, J=8.4 Hz), 5.82 (1H, d, J=1.8 Hz), 4.16 (1H, s), 4.14 (1H, d, J=15.3 Hz), 3.68-3.81 (1H, m), 3.53-3.66 (1H, m), 3.32 (3H, s), 3.17-3.22 (1H, m), 2.90 (1H, brs), 2.39 (3H, s), 2.31-2.38 (2H, m), 1.80 (1H, td, J=5.1, 10.2 Hz), 1.64-1.75 (2H, m), 1.17 (3H, t, J=6.9 Hz); $^{13}$C NMR (DMSO-d$_6$, 75 MHz): δ 192.4, 149.1, 144.2, 143.5, 130.60, 122.7, 120.5, 119.2, 113.2, 70.1, 64.1, 57.8, 53.7, 48.5, 46.3, 44.0, 42.1, 40.2, 35.1, 15.6; IR (KBr): 3414.2, 3288.8, 2968.7, 2935.2, 2901.7, 1697.7, 1681.6, 1627.3, 1483.2, 1349.3, 1291.3, 1198.6, 1152.1, 1090.8, 1071.2, 921.7 cm$^{-1}$; HRMS (ESI, m/z) C$_{20}$H$_{25}$N$_1$Na$_1$O$_5$ (M+Na$^+$) calculated: 382.1625, detected: 382.1640.

Example 24

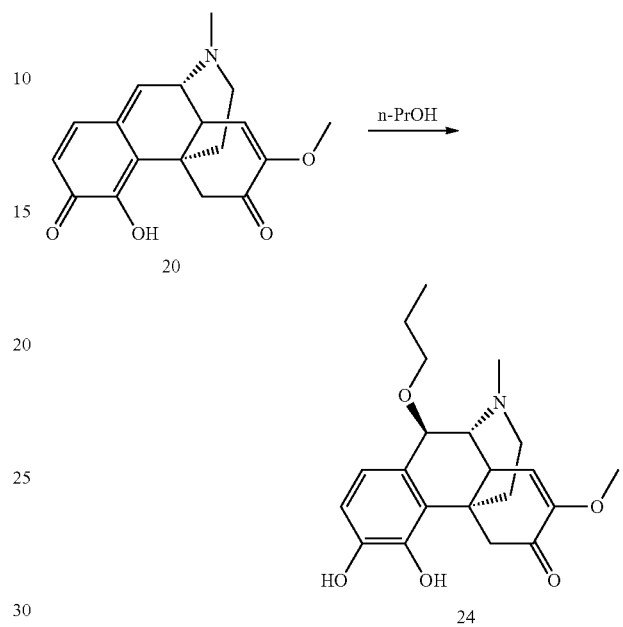

Compound 20 (0.5 g, 1.6 mmol) and n-propanol (10 mL) are added to a 50 mL pear-shaped flask. After the addition, the reaction is stirred at room temperature until TLC shows the disappearance of the starting material. To work up, the solution is evaporated to dryness, and the residue is purified on a column, using dichloromethane/methanol (30/1) as a mobile phase, to obtain the product (0.39 g, 65%).

M.p. 188-190° C. (dec.); $[\alpha]_D^{26}=-29.7$ (c 0.50, CHCl$_3$—CH$_3$OH=10:1); $^1$H NMR (DMSO-d$_6$, 300 MHz): δ 9.40 (1H, brs), 8.10 (1H, brs), 6.64 (1H, d, J=8.4 Hz), 6.60 (1H, d, J=8.1 Hz), 5.79 (1H, d, J=1.8 Hz), 4.15 (1H, s), 4.14 (1H, d, J=15.3 Hz), 3.62-3.72 (1H, m), 3.46-3.57 (1H, m), 3.31 (3H, s), 3.17-3.23 (1H, m), 2.90 (1H, brs), 2.39 (3H, s), 2.31-2.38 (2H, m), 1.80 (1H, td, J=5.1, 10.2 Hz), 1.64-1.75 (2H, m), 1.49-1.63 (2H, m), 0.93 (3H, t, J=7.2 Hz); $^{13}$C NMR (DMSO-d$_6$, 75 MHz): δ 192.4, 149.3, 144.1, 143.5, 130.8, 122.7, 120.4, 119.0, 113.2, 70.9, 70.4, 57.8, 53.7, 48.6, 46.3, 44.1, 42.1, 40.2, 35.1, 23.0, 10.8; IR (KBr): 3269.1, 2956.7, 2931.3, 2909.5, 1682.0, 1625.3, 1490.0, 1348.7, 1306.0, 1286.3, 1197.6, 1071.5, 807.6 cm$^{-1}$; HRMS (ESI, m/z) C$_{21}$H$_{28}$N$_1$O$_5$ (M+H$^+$) calculated: 374.1962, detected: 374.1958.

Example 25

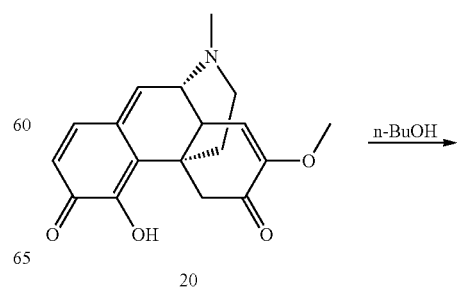

-continued

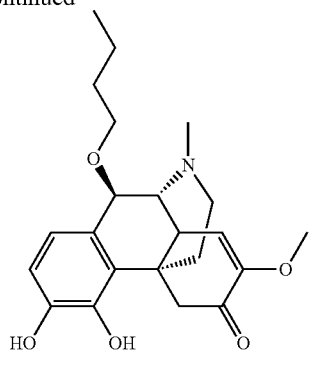

25

Compound 20 (0.5 g, 1.6 mmol) and n-butanol (15 mL) are added to a 100 mL pear-shaped flask. After the addition, the reaction is stirred at room temperature until TLC shows the disappearance of the starting material. To work up, the solution is evaporated to dryness, and the residue is purified on a column, using dichloromethane/methanol (30/1) as a mobile phase, to obtain the product (0.35 g, 57%).

M.p. 182-184° C. (dec.); $[\alpha]_D^{25}$=−26.3 (c 0.50, CHCl$_3$—CH$_3$OH=10:1); $^1$H NMR (DMSO-d$_6$, 400 MHz): δ 9.38 (1H, brs), 8.07 (1H, brs), 6.64 (1H, d, J=8.4 Hz), 6.60 (1H, d, J=8.4 Hz), 5.78 (1H, d, J=2.0 Hz), 4.15 (1H, s), 4.14 (1H, d, J=15.2 Hz), 3.67-3.75 (1H, m), 3.50-3.58 (1H, m), 3.32 (3H, s), 3.14-3.22 (1H, m), 2.90 (1H, brs), 2.39 (3H, s), 2.31-2.38 (2H, m), 1.81 (1H, td, J=4.8, 10.8 Hz), 1.64-1.75 (2H, m), 1.46-1.60 (2H, m), 1.32-1.43 (2H, m), 0.91 (3H, t, J=7.2 Hz); $^{13}$C NMR (DMSO-d$_6$, 75 MHz): δ 192.3, 149.3, 144.1, 143.5, 130.8, 122.7, 120.4, 119.0, 113.2, 70.5, 68.7, 57.8, 53.6, 48.5, 46.3, 44.0, 42.1, 40.2, 35.0, 31.8, 18.9, 13.6; IR (KBr): 3443.0, 2953.3, 2912.2, 2858.5, 2508.6, 1690.8, 1633.3, 1582.1, 1483.4, 1289.9, 1229.7, 1147.6, 1073.3, 1005.7, 795.5 cm$^{-1}$; HRMS (ESI, m/z) C$_{22}$H$_{30}$N$_1$O$_5$ (M+H$^+$) calculated: 388.2119, detected: 388.2135.

Example 26

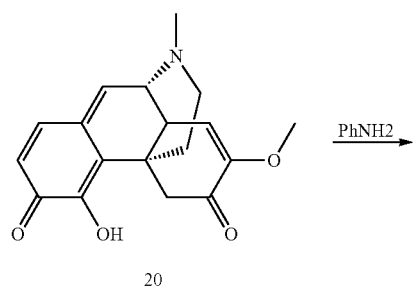

Compound 20 (0.5 g, 1.6 mmol) and dichloromethane (10 mL) are added to a 100 mL pear-shaped flask. The reaction is cooled in an ice bath. To the solution is added aniline (0.18 mL, 1.92 mmol, 1.1 equiv.) dropwise. After the addition, the stirring is continued. The solution is allowed to warm up to the room temperature, and the reaction is continued until TLC shows the disappearance of the starting material. To work up, anhydrous ether is added to the reaction to precipitate solids, which are collected by suction filtration, washed with ethery, and evaporated to obtain the product (0.4 g, 65%).

M.p. 195-197° C. (dec.); $[\alpha]_D^{26}$=25.1 (c 0.60, CHCl$_3$—CH$_3$OH=10:1); $^1$H NMR (CDCl$_3$/CD$_3$OD=10/1, 400 MHz): δ 7.17 (2H, t, J=7.6 Hz), 6.61-6.75 (3H, m), 6.58 (2H, d, J=7.6 Hz), 5.79 (1H, s), 4.58 (1H, s), 4.34 (1H, d, J=15.2 Hz), 3.47 (3H, s), 3.36 (1H, brs), 2.99 (1H, brs), 2.66 (3H, s), 2.43-2.53 (1H, m), 2.38 (1H, d, J=15.6 Hz), 2.07-2.22 (1H, m), 1.69-1.94 (3H, m); $^{13}$C NMR (CDCl$_3$/CD$_3$OD=10/1, 75 MHz): δ 194.9, 150.0, 146.2, 143.8, 130.8, 129.6, 122.1, 120.4, 117.3, 117.2, 113.9, 111.7, 58.6, 54.6, 48.8, 47.7, 46.7, 44.5, 42.4, 40.5, 35.2; IR (KBr): 3421.2, 3254.5, 2910.6, 2855.4, 1680.9, 1600.9, 1500.3, 1307.0, 1289.0, 1200.7, 749.2 cm$^{-1}$; HRMS (ESI, m/z) C$_{24}$H$_{27}$N$_2$O$_4$ (M+H$^+$) calculated: 407.1965, detected: 407.1965.

Example 27

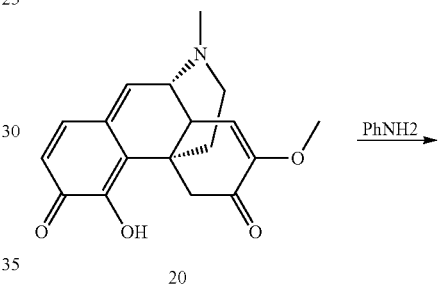

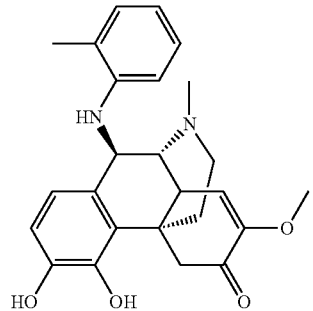

27

Compound 20 (0.5 g, 1.6 mmol) and dichloromethane (15 mL) are added to a 100 mL pear-shaped flask. After the addition, the reaction is stirred at room temperature, and o-methylaniline (0.2 mL, 1.91 mmol, 1.1 equiv.) is added. After the addition, the stirring is continued until TLC shows the disappearance of the starting material. To work up, the solution is evaporated to dryness, and the residue is purified on a column to obtain the product (0.38 g, 57%).

M.p. 165-168° C. (dec.); $[\alpha]_D^{25}$=14.0 (c 0.10, CHCl$_3$—CH$_3$OH=10:1); $^1$H NMR (DMSO-d$_6$, 500 MHz): δ 9.45 (1H, brs), 8.21 (1H, brs), 7.12 (1H, t, J=7.5 Hz), 7.04 (1H, d, J=7.0 Hz), 6.83 (1H, d, J=8.0 Hz), 6.67 (1H, d, J=8.0 Hz), 6.55-6.62 (2H, m), 5.90 (1H, s), 4.52 (1H, d, J=5.5 Hz), 4.22 (1H, d, J=15.0 Hz), 3.68 (1H, d, J=6.0 Hz), 3.43 (3H, s), 3.17 (1H, brs), 3.04 (1H, brs), 2.61 (3H, s), 2.40-2.47 (2H, m), 2.06-2.13 (1H, m), 2.04 (3H, s), 1.63-1.84 (2H, m); $^{13}$C NMR (DMSO-d$_6$, 125 MHz): δ 192.5, 150.1, 145.1, 144.1, 143.9, 131.5, 130.1, 127.1, 123.2, 120.8, 119.1, 117.3, 116.1, 113.9,

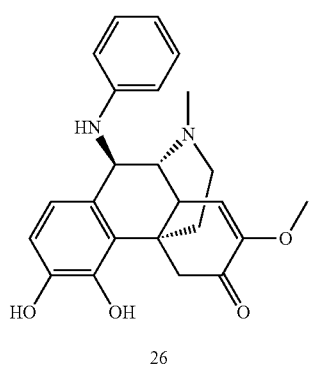

26

108.4, 59.6, 54.1, 48.7, 48.5, 46.0, 43.3, 42.6, 40.2, 34.3, 17.4; IR (KBr): 3503.2, 3461.0, 3011.8, 2928.6, 2848.8, 1685.8, 1615.9, 1603.6, 1584.5, 1503.9, 1446.5, 1308.5, 1283.9, 1197.6, 758.9 cm$^{-1}$; HRMS (ESI, m/z) C$_{25}$H$_{29}$N$_2$O$_4$ (M+H$^+$) calculated: 421.2122, detected: 421.2120.

Example 28

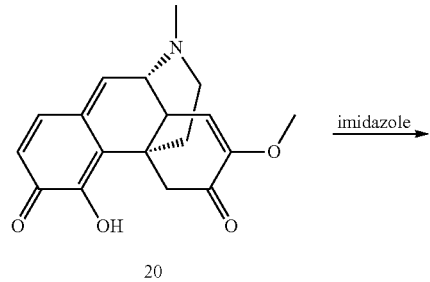

20

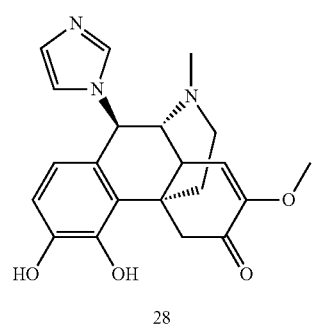

28

Compound 20 (0.5 g, 1.6 mmol) and DMF (n,N-dimethylformamide) (10 mL) are added to a 50 mL pear-shaped flask. After the reaction is stirred at room temperature, and imidazole (0.163 g, 2.39 mmol, 1.5 equiv.) is added. After the addition, the stirring is continued until TLC shows the disappearance of the starting material. To work up, the solution is evaporated to dryness, and the residue is purified on a column to obtain the product (0.18 g, 29%).

M.p. 211-213° C. (dec.); [α]$_D^{26}$=82.8 (c 0.40, CHCl$_3$—CH$_3$OH=10:1); $^1$H NMR (DMSO-d$_6$, 400 MHz): δ 9.73 (1H, brs), 8.41 (1H, brs), 7.12 (1H, s), 7.01 (1H, s), 6.93 (1H, s), 6.73 (1H, d, J=8.4 Hz), 6.51 (1H, d, J=8.0 Hz), 5.32 (1H, s), 4.66 (1H, d, J=2.4 Hz), 4.25 (1H, d, J=15.2 Hz), 3.14 (3H, s), 2.97 (1H, brs), 2.54 (1H, s), 2.42-2.48 (1H, m), 2.43 (1H, d, J=15.2 Hz), 1.83-1.96 (1H, m), 1.69-1.82 (2H, m); $^{13}$C NMR (DMSO-d$_6$, 75 MHz): δ 192.3, 149.7, 145.0, 144.4, 137.0, 127.9, 125.0, 124.2, 120.7, 119.5, 115.5, 113.6, 62.6, 53.2, 50.1, 48.3, 46.3, 43.8, 42.3, 35.4; IR (KBr): 3410.7, 2937.8, 2917.8, 2850.4, 2536.1, 1697.0, 1628.4, 1586.1, 1485.1, 1390.8, 1295.2, 1223.1, 1150.9, 1068.4, 917.5, 742.5, 497.0 cm$^{-1}$; HRMS (ESI, m/z) C$_{21}$H$_{23}$N$_3$Na$_1$O$_4$ (M+Na$^+$) calculated: 404.1581, detected: 404.1586.

Example 29

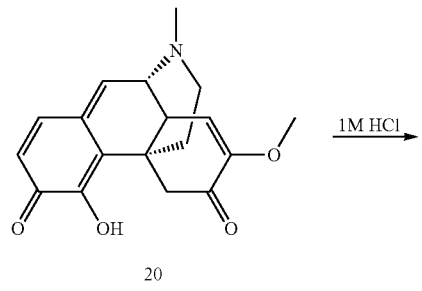

20

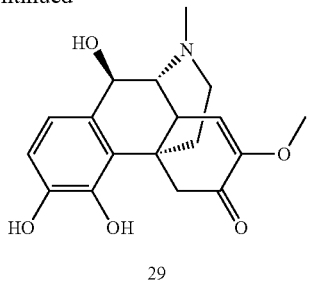

29

Compound 20 (0.5 g, 1.6 mmol) and 1M HCl aqueous solution (10 mL) are added to a 50 mL pear-shaped flask. After the addition, the stirring is continued until TLC shows the disappearance of the starting material. To work up, a solution of saturated sodium bicarbonate is added to the reaction mixture to make it alkaline. The solution is evaporated and the residue is purified on a column to obtain the product (0.14 g, 53%).

M.p. 171-173° C. (dec.); [α]$_D^{26}$=-44.9 (c 0.10, CHCl$_3$—CH$_3$OH=10:1); $^1$H NMR (DMSO-d$_6$, 400 MHz): δ 9.33 (1H, brs), 8.04 (1H, brs), 6.69 (1H, d, J=8.4 Hz), 6.64 (1H, d, J=8.0 Hz), 5.89 (1H, d, J=2.0 Hz), 4.93 (1H, brs), 4.53 (1H, s), 4.15 (1H, d, J=15.2 Hz), 3.34 (3H, s), 3.09 (1H, brs), 2.90 (1H, brs), 2.27-2.46 (5H, m), 1.77-1.90 (1H, m), 1.61-1.75 (2H, m); $^{13}$C NMR (DMSO-d$_6$, 75 MHz): δ 192.5, 149.2, 143.9, 143.5, 132.8, 122.4, 120.0, 119.2, 113.3, 62.5, 61.7, 53.8, 48.6, 46.3, 43.8, 42.4, 40.3, 35.0; IR (KBr): 3383.0, 2960.5, 2897.1, 1674.2, 1621.2, 1492.5, 1285.5, 1201.6, 1155.2, 1103.7, 1025.1, 831.2 cm$^{-1}$; HRMS (ESI, m/z) C$_{18}$H$_{22}$N$_1$O$_5$ (M+H$^+$) calculated: 332.1493, detected: 332.1490.

Example 30

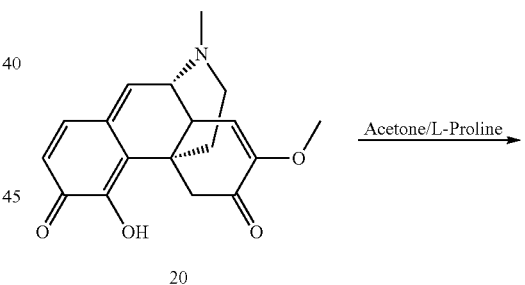

20

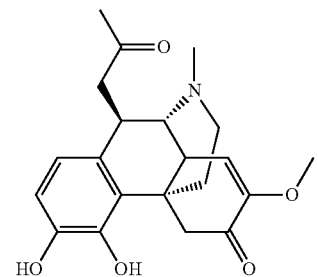

30

Compound 20 (1 g, 3.2 mmol, 1 equiv.) and DMSO (dimethylsulfoxide) (10 mL) are added to a 100 mL pear-shaped flask. After the addition, the reaction is stirred at room temperature, and acetone (2.5 mL, 33.8 mmol, 10.6 equiv.) and L-proline (0.1 g, 0.87 mmol, 0.27 equiv.) are added. After the addition, the stirring is continued until TLC shows the disappearance of the starting material. To work up, water is added to the reaction mixture, and the resulting mixture is then extracted with dichloromethane several times. The combined dichloromethane extracts are washed with water, saturated NaCl, and dried with anhydrous sodium sulfate. The solution is filtered, dried, and the residue is purified on a column to obtain the product (0.17 g, 14%).

M.p. 219-221° C.; $[\alpha]_D^{26}=-64.9$ (c 0.30, CHCl$_3$—CH$_3$OH=10:1); $^1$H NMR (DMSO-d$_6$, 500 MHz): δ 9.20 (1H, brs), 8.01 (1H, brs), 6.57 (1H, d, J=8.0 Hz), 6.40 (1H, d, J=8.0 Hz), 5.83 (1H, s), 4.19 (1H, d, J=15.0 Hz), 3.44 (3H, s), 3.41 (1H, dd, J=8.5, 5.0 Hz), 2.91-3.00 (3H, m), 2.82 (1H, dd, J=15.0, 4.5 Hz), 2.36 (1H, d, J=15.0 Hz), 2.33-2.36 (1H, m), 2.32 (3H, s), 2.17 (3H, s), 1.83-1.93 (1H, m), 1.67-1.75 (2H, m); $^{13}$C NMR (DMSO-d$_6$, 125 MHz): δ 207.5, 192.6, 150.2, 143.9, 142.6, 133.2, 122.9, 117.5, 116.9, 113.5, 60.1, 54.1, 51.7, 48.6, 46.2, 45.2, 42.3, 35.8, 30.0, 27.9; IR (KBr): 3486.4, 3017.7, 2931.8, 2859.7, 1688.6, 1626.8, 1488.0, 1450.5, 1365.7, 1286.2, 1203.7, 1147.4, 1086.0, 807.9 cm$^{-1}$; HRMS (ESI, m/z) C$_{21}$H$_{26}$N$_1$O$_5$ (M+H$^+$) calculated: 372.1806, detected: 372.1820.

Example 31

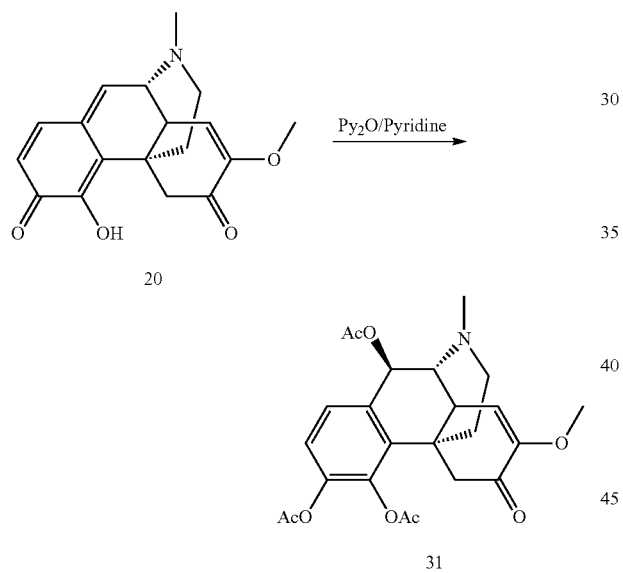

Compound 20 (0.507 g, 1.6 mmol, 1 equiv.) is dissolved in pyridine (10 mL) in a 100 mL pear-shaped flask. To the solution, acetic anhydride (0.2 mL, 2 mmol, 1.2 equiv.) is added dropwise. After the addition, the reaction is stirred at room temperature until TLC shows the disappearance of the starting material. To work up, the reaction solution is evaporated to dryness, and then a saturated sodium bicarbonate solution is added to make it alkaline. The solution is extracted with dichloromethane several times. The combined dichloromethane extracts are washed with water, saturated NaCl, and dried with anhydrous sodium sulfate. The solution is filtered and evaporated to obtain the product (0.565 g, 79%).

M.p. 198-199° C.; $[\alpha]_D^{26}=-82.0$ (c 0.50, CHCl$_3$); $^1$H NMR (DMSO-d$_6$, 400 MHz): δ 7.22 (1H, d, J=8.8 Hz), 7.18 (1H, d, J=8.4 Hz), 5.89 (1H, d, J=2.0 Hz), 3.50 (1H, d, J=15.6 Hz), 3.39 (3H, s), 3.26 (1H, d, J=1.8 Hz), 3.06 (1H, brs), 2.73 (1H, 15.6), 2.46 (3H, s), 2.39-2.45 (1H, m), 2.36 (3H, s), 2.22 (3H, s), 2.09 (3H, s), 1.76-1.88 (2H, m), 1.38 (1H, d, J=9.6 Hz); $^{13}$C NMR (DMSO-d$_6$, 75 MHz): δ 190.7, 169.6, 167.7, 149.8, 142.6, 140.7, 135.1, 130.9, 127.4, 122.2, 117.6, 64.0, 58.6, 54.0, 49.0, 45.6, 43.4, 42.2, 40.4, 35.9, 21.0, 20.5, 20.4; MS (ESI, m/z): 458.7 (M+H$^+$). IR (KBr): 3411.8, 2938.0, 2845.7, 1777.1, 1727.3, 1691.0, 1632.9, 1375.0, 1234.9, 1200.7, 1146.6, 1014.8 cm$^{-1}$; HRMS (ESI, m/z) C$_{24}$H$_{28}$N$_1$O$_8$ (M+H$^+$) calculated: 458.1804, detected: 458.1804.

Example 32

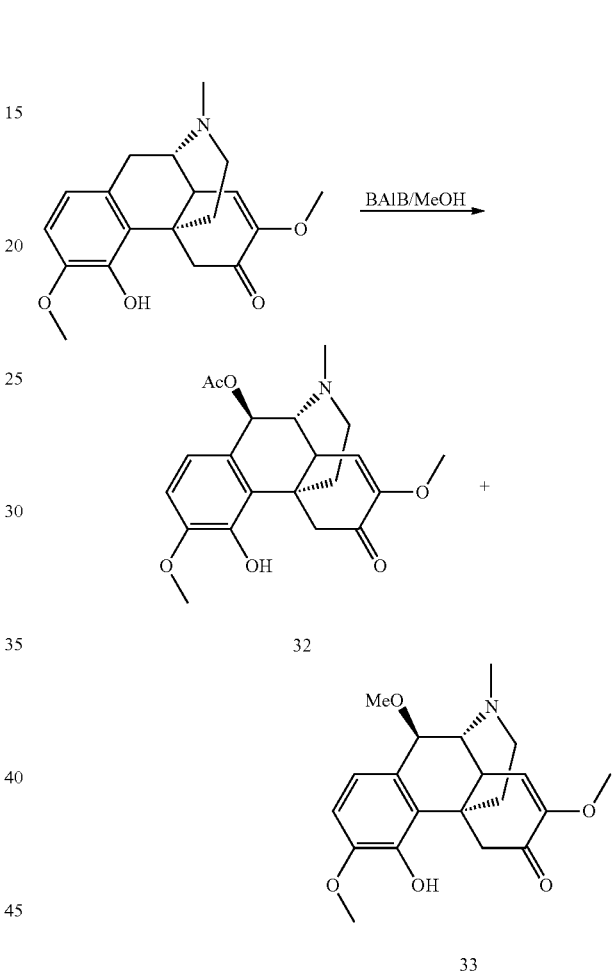

Sinomenine (0.1 g, 0.30 mmol, 1 equiv.) is dissolved in methanol (2.5 mL) in a 25 mL pear-shaped flask. The mixture is stirred at room temperature, and iodobenzene diacetate (0.1 g, 0.31 mmol, 1 equiv.) is added. The reaction solution turned pale yellow. TLC shows the starting material has disappeared. To work up, a solution of saturated sodium bicarbonate is added to the solution. The solution is then extracted with dichloromethane (DCM). The combined organic extract is washed with saturated NaCl, and dried with anhydrous Na$_2$SO$_4$. The solution is filtered, dried, and the residue is purified with column chromatography to obtain the products, 10β-acetoxysinomenine (12 mg, 10%) and 10β-methoxysinomenine (58 mg, 53%).

Compound 32 m.p. 232-234° C. (dec.); $[\alpha]_D^{25}=-73.5$ (c 1.4, CHCl$_3$); $^1$H NMR (CDCl$_3$, 400 MHz): δ 6.70-6.76 (2H, m), 6.12 (1H, brs), 6.03 (1H, s), 5.62 (1H, d, J=2.0 Hz), 4.34 (1H, d, J=15.6 Hz), 3.83 (3H, s), 3.50 (3H, s), 3.22 (1H, brs), 3.10 (1H, brs), 2.60 (3H, s), 2.53-2.61 (1H, m), 2.45 (1H, d, J=15.6 Hz), 2.10 (3H, s), 2.05 (1H, td, J=11.6, 4.8 Hz), 1.83-1.96 (2H, m); $^{13}$C NMR (CDCl$_3$, 75 MHz): δ 193.4, 170.2, 150.9, 146.8, 144.3, 129.4, 122.4, 120.6, 116.6, 109.3, 65.0, 60.8, 55.9, 54.5, 49.1, 46.8, 44.8, 42.8, 40.7, 35.8, 21.5; IR (KBr): 3373.8, 2938.9, 2840.3, 2248.7, 1725.8, 1682.0, 1634.5, 1488.2, 1463.7, 1283.7, 1234.2, 1145.9, 1058.2, 1006.4, 947.2, 729.7 cm$^{-1}$; HRMS (ESI, m/z) C$_{21}$H$_{26}$N$_1$O$_6$ (M+H$^+$) Calculated: 388.1755, detected: 388.1755.

Compound 33 m.p. 201-203° C. (dec.); $[α]_D^{25}$=−38.8 (c 1.4, CHCl$_3$); $^1$H NMR (CDCl$_3$, 300 MHz): δ 6.85 (1H, d, J=8.4 Hz), 6.72 (1H, d, J=8.4 Hz), 6.07 (1H, brs), 5.73 (1H, d, J=2.1 Hz), 4.32 (1H, d, J=15.9 Hz), 4.17 (1H, s), 3.82 (3H, s), 3.55 (3H, s), 3.45 (3H, s), 3.32 (1H, d, J=3.0 Hz), 3.03 (1H, brs), 2.54 (3H, s), 2.45-2.53 (1H, m), 2.41 (1H, d, J=15.6 Hz), 1.99 (1H, td, J=3.6, 11.7 Hz), 1.77-1.93 (2H, m); $^{13}$C NMR (CDCl$_3$, 75 MHz): δ 193.6, 150.6, 146.3, 144.2, 131.8, 121.9, 120.8, 117.8, 109.1, 72.5, 58.5, 57.6, 56.0, 54.7, 49.3, 46.9, 45.0, 42.6, 40.9, 35.8; IR (KBr): 3441.6, 2917.4, 2848.2, 2247.1, 1687.1, 1628.8, 1486.4, 1439.7, 1278.0, 1202.5, 1150.5, 1078.4, 1056.1, 1029.7, 948.8, 827.2, 731.7 cm$^{-1}$; HRMS (ESI, m/z) C$_{20}$H$_{26}$N$_1$O$_5$ (M+H$^+$) calculated: 360.1806, detected: 360.1809.

Example 33

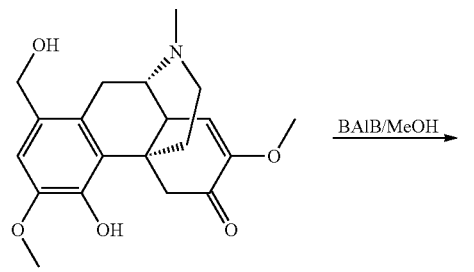

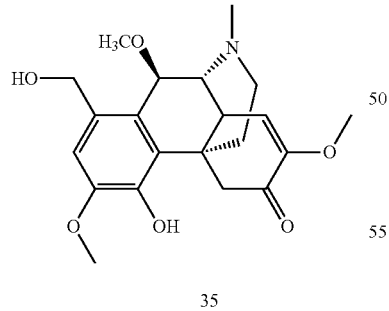

1-Hydroxymethyl-sinomenine (0.1 g, 0.28 mmol, 1 equiv.) is dissolved in methanol (2.5 mL) in a reaction flask. The mixture is stirred at room temperature, and iodobenzene diacetate (0.1 g, 0.31 mmol, 1.1 equiv.) is added. The reaction solution turned pale yellow. TLC shows the starting material has disappeared. To work up, a solution of saturated sodium bicarbonate is added to the solution. The solution is then extracted with dichloromethane (DCM). The combined organic extract is washed with saturated NaCl, and dried with anhydrous Na$_2$SO$_4$. The solution is filtered, dried, and the residue is purified with column chromatography to obtain the products, 1-hydroxymethyl-10β-acetoxysinomenine (18 mg, 22%) and 1-hydroxymethyl-10β-methoxysinomenine (59 mg, 54%).

Compound 34 m.p. 176-178° C. (dec.); $[α]_D^{26}$=−54.3 (c 0.2, CHCl$_3$); $^1$H NMR (CDCl$_3$, 500 MHz): δ 6.96 (1H, s), 6.23 (1H, brs), 6.15 (1H, s), 5.54 (1H, d, J=1.5 Hz), 4.50 (1H, d, J=13.0), 4.42 (1H, d, J=12.5 Hz), 4.38 (1H, d, J=15.5 Hz), 3.85 (3H, s), 3.49 (3H, s), 3.31 (1H, brs), 3.18 (1H, brs), 2.66 (3H, s), 2.58-2.63 (1H, m), 2.46 (1H, d, J=16.0 Hz), 2.09 (3H, s), 2.01-2.08 (1H, m), 1.91-1.96 (2H, m); $^{13}$C NMR (CDCl$_3$, 125 MHz): δ 193.3, 169.7, 150.9, 147.2, 143.8, 131.6, 125.0, 122.5, 116.0, 109.9, 63.2, 62.0, 60.6, 56.0, 54.5, 48.8, 47.1, 43.8, 42.5, 40.6, 35.1, 21.3; IR (KBr): 3419.3, 2937.2, 2842.3, 1730.0, 1688.5, 1631.2, 1464.3, 1438.5, 1371.0, 1288.7, 1230.0, 1150.2, 1107.5, 1076.1, 1014.7 cm$^{-1}$; HRMS (ESI, m/z) C$_{22}$H$_{28}$N$_1$O$_7$ (M+H$^+$) Calculated: 418.1860, detected: 418.1871.

Compound 35 m.p. 167-169° C.; $[α]_D^{26}$=−62.3 (c 0.2, CHCl$_3$); $^1$H NMR (CDCl$_3$, 500 MHz): δ 6.85 (1H, s), 5.66 (1H, s), 4.55 (1H, d, J=12.0 Hz), 4.56 (3H, s), 4.37 (1H, d, J=12.0 Hz), 4.35 (1H, d, J=15.5 Hz), 3.81 (3H, s), 3.56 (3H, s), 3.50 (1H, brs), 3.42 (3H, s), 3.21 (1H, brs), 2.59-2.63 (1H, m), 2.61 (3H, s), 2.44 (1H, d, J=16.0 Hz), 2.02-2.08 (1H, m), 1.89-1.98 (2H, m); $^{13}$C NMR (CDCl$_3$, 125 MHz): δ 193.3, 150.8, 146.8, 143.9, 132.6, 128.6, 122.1, 116.6, 111.5, 71.1, 63.7, 57.4, 55.9, 55.7, 54.7, 48.8, 47.0, 43.6, 42.1, 40.8, 34.6; IR (KBr): 3381.2, 2938.1, 1685.9, 1630.0, 1600.9, 1465.8, 1289.6, 1202.4, 1107.1, 1073.7, 1035.7, 947.8 cm$^{-1}$; HRMS (ESI, m/z) C$_{21}$H$_{28}$N$_1$O$_6$ (M+H$^+$) calculated: 390.1911, detected: 390.1912.

Example 34

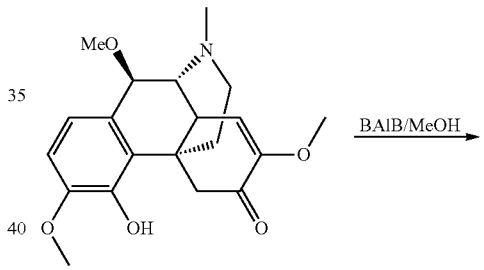

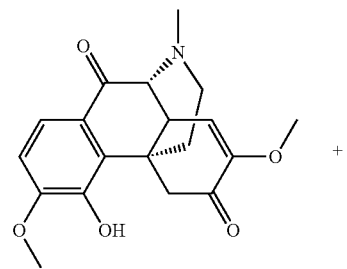

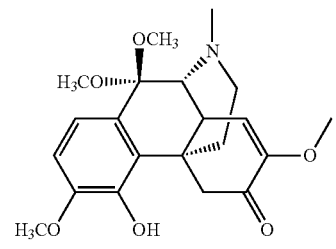

Compound 33 (0.1 g, 0.28 mmol, 1 equiv.) is dissolved in methanol (2.5 mL) in a reaction flask. The mixture is stirred at room temperature, and iodobenzene diacetate (0.09 g, 0.28 mmol, 1 equiv.) is added. The reaction solution turned pale yellow. TLC shows the starting material has disappeared. To work up, a solution of saturated sodium bicarbonate is added to the solution. The solution is then extracted with dichloromethane (DCM). The combined organic extract is washed with saturated NaCl, and dried with anhydrous $Na_2SO_4$. The solution is filtered, dried, and the residue is purified with column chromatography to obtain the products, 10-oxosinomenine (11 mg, 12%) and 10,10-dimethoxy-sinomenine (41 mg, 41%).

Compound 37 m.p. 219-221° C. (dec.); $[\alpha]_D^{25}=-190.5$ (c 0.7, $CHCl_3$); $^1H$ NMR ($CDCl_3$, 400 MHz): δ 7.65 (1H, d, J=8.4 Hz), 6.80 (1H, d, J=8.4 Hz), 6.11 (1H, brs), 5.35 (1H, d, J=2.0 Hz), 4.35 (1H, d, J=16.0 Hz), 3.91 (3H, s), 3.43 (3H, s), 3.37 (1H, d, J=3.6 Hz), 3.19-3.24 (1H, m), 2.64-2.73 (1H, m), 2.47 (1H, d, J=16.0 Hz), 2.39 (3H, s), 1.94-2.12 (3H, m); $^{13}C$ NMR ($CDCl_3$, 75 MHz): δ 193.2, 192.7, 152.9, 151.9, 144.1, 129.7, 126.2, 119.5, 113.4, 108.8, 67.0, 56.1, 54.9, 49.3, 47.2, 46.4, 43.1, 41.4, 35.2; IR (KBr): 3421.2, 2937.8, 2842.4, 2248.6, 1691.2, 1627.3, 1590.9, 1482.8, 1457.9, 1351.0, 1310.5, 1275.5, 1201.8, 1174.7, 1152.1, 1099.3, 1050.8, 733.6 cm$^{-1}$; HRMS (ESI, m/z) $C_{19}H_{22}N_1O_5$ (M+H$^+$) calculated: 344.1493, detected: 344.1496.

Compound 36 m.p. 181-183° C. (dec.); $[\alpha]_D^{25}=-28.8$ (c 1.5, $CHCl_3$); $^1H$ NMR ($CDCl_3$, 300 MHz): δ 7.15 (1H, d, J=8.7 Hz), 6.73 (1H, d, J=8.7 Hz), 5.86 (1H, d, J=1.8 Hz), 4.29 (1H, d, J=15.3 Hz), 3.84 (3H, s), 3.49 (3H, s), 3.40 (3H, s), 3.24-3.32 (2H, m), 2.95 (3H, s), 2.72 (3H, s), 2.54 (1H, td, J=3.3, 12.6 Hz), 2.36-2.47 (2H, m), 1.89 (1H, td, J=4.8, 12.6 Hz), 1.53-1.63 (1H, m); $^{13}C$ NMR ($CDCl_3$, 75 MHz): δ 194.1, 148.9, 147.0, 144.0, 128.7, 122.4, 119.6, 119.4, 107.8, 97.5, 61.3, 55.9, 54.5, 49.4, 48.9, 48.3, 45.4, 43.4, 42.5, 41.8, 32.8; IR (KBr): 3436.1, 2918.4, 2848.9, 1686.0, 1625.9, 1482.2, 1439.0, 1310.9, 1273.6, 1203.5, 1151.1, 1115.7, 1075.8, 732.5 cm$^{-1}$; HRMS (ESI, m/z) $C_{21}H_{28}N_1O_6$ (M+H$^+$) calculated: 390.1911, detected: 390.1919.

Example 35

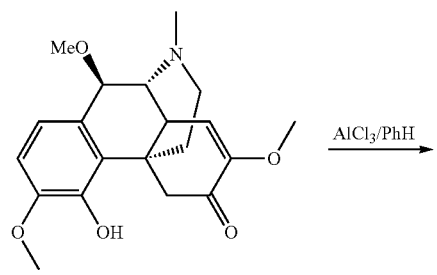

33

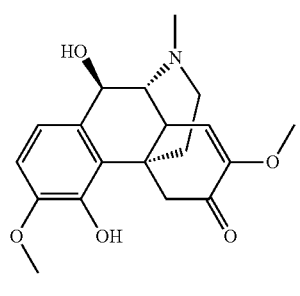

38

Compound 33 (0.1 g, 0.28 mmol, 1 equiv.) and aluminium trichloride (0.1 g, 0.42 mmol, 1.5 equiv.) are added to a reaction flask. The atmosphere in the flask is replaced with nitrogen gas, and benzene (5 mL) is added. The mixture is heated to reflux. The reaction mixture turned cloudy, and many insoluble materials adhere to the side of the flask. The reaction is continued until TLC shows the starting material has disappeared. To work up, a solution of saturated sodium bicarbonate is added to the solution. The solution is filtered through diatomite, and the solid is washed with DCM. The filtrate is extracted with DCM. The combined organic extract is washed with water, saturated NaCl, and dried with anhydrous $Na_2SO_4$. The solution is filtered, dried, and the residue is purified with column chromatography to obtain the product (43 mg, 45%).

$[\alpha]_D^{25}=-28.9$ (c=0.80, $CHCl_3$); $^1H$ NMR ($CDCl_3$, 300 MHz): δ 6.93 (1H, d, J=8.4), 6.78 (1H, d, J=8.4), 6.21 (1H, brs), 5.87 (1H, brs), 4.84 (1H, s), 4.36 (1H, d, J=15.6), 3.85 (3H, s), 3.46-3.59 (1H, m), 3.54 (3H, s), 3.27 (1H, brs), 2.67 (3H, s), 2.57-2.66 (1H, m), 2.49 (1H, d, J=15.6), 2.08-2.21 (1H, m), 1.86-2.06 (2H, m); $^{13}C$ NMR ($CDCl_3$, 75 MHz): δ 193.3, 150.9, 146.7, 144.4, 132.6, 121.1, 120.2, 116.1, 109.8, 63.6, 62.6, 56.1, 54.9, 48.9, 47.1, 43.8, 42.5, 40.5, 35.1; IR (KBr): 3436.1, 2918.4, 2848.9, 1686.0, 1625.9, 1482.2, 1439.0, 1310.9, 1273.6, 1203.5, 1151.1, 1115.7, 1075.8, 732.5 cm$^{-1}$; MS 346.2. (M+1)$^+$.

Example 36

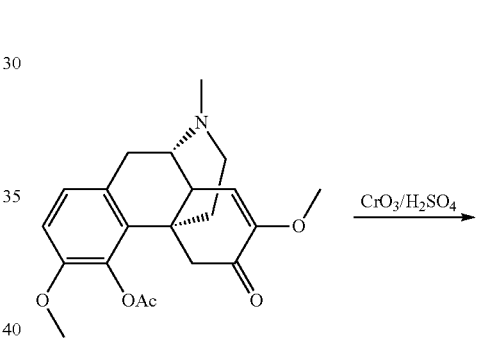

41

4-Acetyl-sinomenine (0.5 g, 1.35 mmol, 1 equiv.) in 1.5M aqueous sulfuric acid solution (8 mL) is added to a reaction flask. The reaction is stirred at room temperature and solid $CrO_3$ (0.27 g, 2.70 mmol, 2 equiv.) is added with stirring. After addition, concentrated sulfuric acid (0.36 mL, 6.62 mmol, 4.9 equiv.) is added to the reaction solution. After the addition, the reaction is stirred at room temperature overnight. To work up, a solution of saturated sodium sulfite is added to the solution, followed by addition of saturated sodium hydroxide to make the solution alightly acidic and addition of saturated sodium bicarbonate to make it alkaline. The solution is extracted with DCM. The combined dichloromethane extract is washed with water, saturated NaCl, and dried with anhydrous $Na_2SO_4$. The solution is filtered, dried, and the residue is purified with column chromatography to obtain the product (0.17 g, 32%).

$^1$H NMR (CDCl$_3$, 400 MHz): δ 7.98 (1H, d, J=8.4), 6.91 (1H, d, J=8.8), 5.35 (1H, d, J=2.4), 3.82-3.91 (1H, m), 3.84 (3H, s), 3.43 (3H, s), 3.34 (1H, d, J=3.6), 3.19 (1H, t, J=1.8), 2.62-2.71 (1H, m), 2.53 (1H, d, J=16.0), 2.38 (3H, s), 2.37 (3H, s), 2.10 (1H, td, J=12.4, 3.2), 1.99 (1H, td, J=12.8, 4.8), 1.70-1.81 (1H, m); MS 385.9 (M+1)$^+$.

Example 37

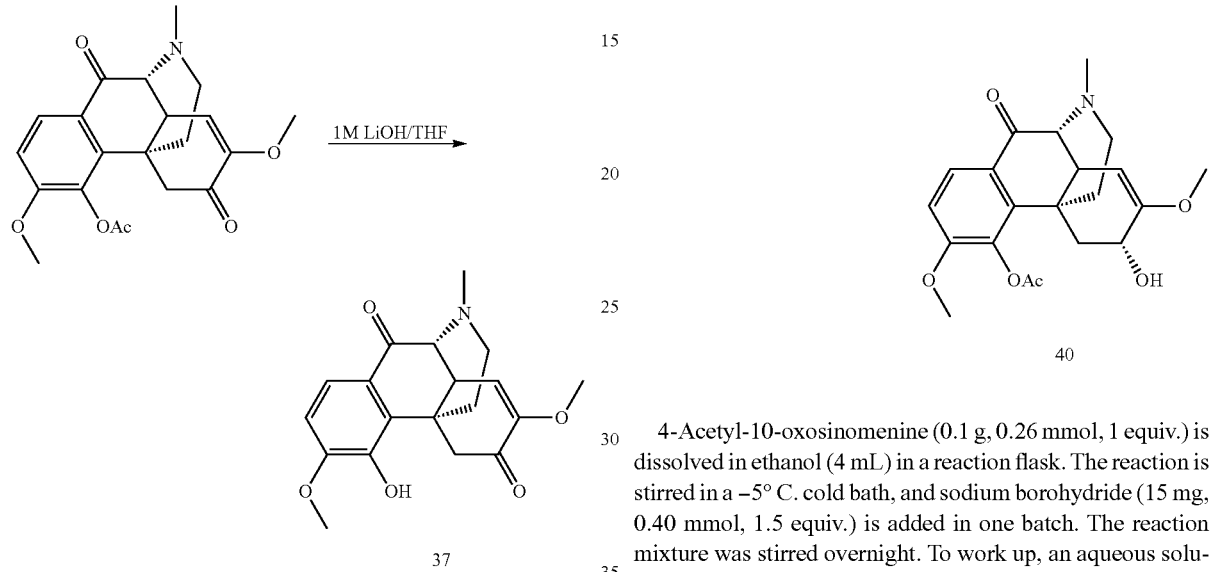

4-Acetyl-10-oxosinomenine (0.5 g, 1.3 mmol, 1 equiv.) is dissolved in tetrahydrofuran (10 mL) in a reaction flask. The reaction is stirred in an ice bath, and 1M LiOH aqueous solution is added dropwise. After the addition, the reaction is allowed to warm up to room temperature and the reaction is continued until TLC shos the disappearance of the starting material. To work up, a solution of dilute hydrochloric acid is added to the solution to make it slightly acidic, followed by addition of saturated sodium bicarbonate to make it alkaline. Tetrahydrofuran is evaporated. The solution is extracted with DCM. The combined dichloromethane extract is washed with water, saturated NaCl, and dried with anhydrous Na$_2$SO$_4$. The solution is filtered and evaporated to obtain the product, 10-oxosinomenine (0.4 g, 90%).

Analysis data are the same as those in Example 34.

Example 38

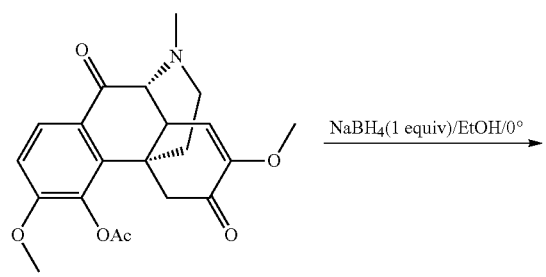

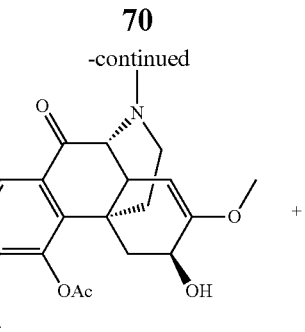

4-Acetyl-10-oxosinomenine (0.1 g, 0.26 mmol, 1 equiv.) is dissolved in ethanol (4 mL) in a reaction flask. The reaction is stirred in a −5° C. cold bath, and sodium borohydride (15 mg, 0.40 mmol, 1.5 equiv.) is added in one batch. The reaction mixture was stirred overnight. To work up, an aqueous solution of acetic acid is added to quench the reaction. The solvents are removed by rotary evaporation. A saturated sodium bicarbonate solution is added to make it alkaline. The solution is extracted with DCM. The combined dichloromethane extract is washed with water, saturated NaCl, and dried with anhydrous Na$_2$SO$_4$. The solution is filtered and dried, and the residue is purified on a column to obtain the products, Compound 39 (44 mg, 44%) and Compound 40 (23 mg, 23%).

Compound 39 $^1$H NMR (CDCl$_3$, 400 MHz): δ 7.65 (1H, d, J=8.4), 6.86 (1H, d, J=8.8), 5.96 (1H, s), 5.25 (1H, d, J=4.8), 4.55 (1H, d, J=1.6), 3.95 (3H, s), 3.73 (1H, d, J=15.2), 3.39 (3H, s), 3.25 (1H, d, 3.2), 2.74-2.77 (1H, m), 2.63-2.71 (1H, m), 2.33 (3H, s), 1.94-2.08 (2H, m), 1.80 (3H, s), 1.63-1.79 (2H, m); $^{13}$C NMR (CDCl$_3$, 75 MHz): δ 194.4, 170.5, 153.5, 150.7, 144.4, 129.9, 129.2, 119.1, 108.5, 97.8, 68.2, 68.0, 56.1, 54.6, 48.0, 45.6, 42.9, 37.2, 35.4, 35.1, 20.9; IR (KBr): 3246.0, 2936.8, 2906.0, 2798.8, 1722.4, 1663.7, 1587.5, 1482.4, 1370.2, 1309.9, 1275.6, 1238.9, 1203.3, 1171.0, 1085.0, 1060.7, 1020.6, 863.4 cm$^{-1}$; MS 388.0 (M+1)$^+$.

Compound 40 [α]$_D^{25}$=−158.4 (c 1.5, CHCl$_3$); $^1$H NMR (CDCl$_3$, 400 MHz): δ 7.96 (1H, d, J=8.8), 6.93 (1H, d, J=8.4), 4.32 (1H, s), 7.06-7.16 (1H, m), 3.87 (3H, s), 3.39 (3H, s), 3.19 (1H, d, J=3.2), 2.99-3.18 (1H, m), 2.91 (1H, brs), 2.60-2.70 (1H, m), 2.49 (1H, brs), 2.37 (3H, s), 2.33 (3H, s), 2.04 (1H, brs), 1.89 (1H, td, J=4.8, 12.8), 1.59-1.79 (2H, m); $^{13}$C NMR (CDCl$_3$, 75 MHz): δ 193.6, 168.5, 156.5, 156.1, 138.4, 136.2, 129.5, 125.8, 110.2, 94.3, 67.4, 66.1, 56.1, 54.6, 47.4, 46.2, 43.0, 41.7, 38.5, 36.2, 20.9; MS 388.0 (M+1)$^+$.

Example 39

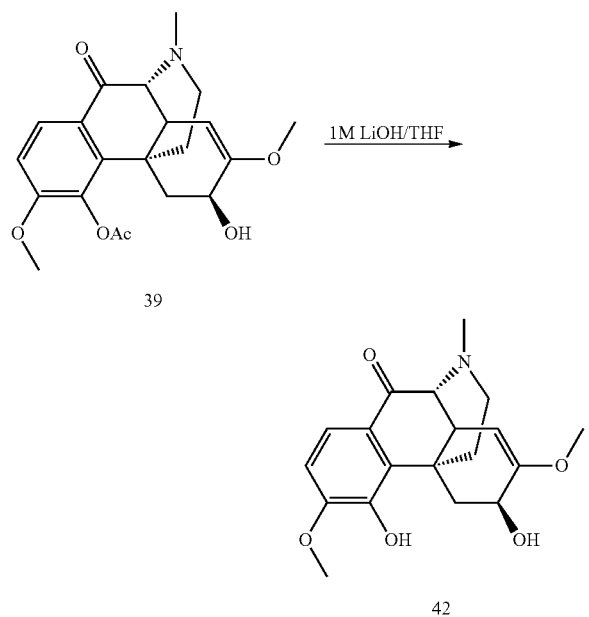

Compound 39 (0.2 g, 0.52 mmol) is dissolved in tetrahydrofuran (10 mL) in a reaction flask. An aqueous solution of 1M LiOH (10 mL) is added dropwise. After the addition, the reaction is continued and allowed to warm up to room temperature. The reaction is continued until TCL shows the disappearance of the starting material. To work up, an aqueous solution of dilute hydrochloric acid is added to make it acidic, followed by addition of a saturated sodium bicarbonate solution to make it alkaline. Tetrahydrofuran is removed by rotary evaporation. The solution is extracted with DCM. The combined dichloromethane extract is washed with water, saturated NaCl, and dried with anhydrous $Na_2SO_4$. The solution is filtered and evaporated to obtain the product, 10-oxosinomenine (0.18 g, 100%).

$^1$H NMR (CDCl$_3$, 300 MHz): δ 7.64 (1H, d, J=8.7), 6.83 (1H, d, J=8.4), 6.26 (1H, brs), 4.40 (1H, s), 4.21 (1H, d, J=5.1), 3.92 (3H, s), 3.69 (1H, d, J=15.0), 3.41 (3H, s), 3.24 (1H, d, J=3.3), 2.70-2.75 (1H, m), 2.62-2.71 (1H, m), 2.34 (3H, s), 2.04-2.11 (1H, m), 1.94-2.02 (1H, m), 1.89 (1H, brs), 1.66-1.82 (2H, m); $^{13}$C NMR (CDCl$_3$, 100 MHz): δ 194.5, 156.76, 151.4, 144.1, 129.7, 129.5, 119.5, 108.6, 95.1, 68.3, 66.2, 56.1, 54.51, 47.9, 45.8, 42.9, 40.0, 35.7, 35.2; IR (KBr): 3432.3, 2910.0, 2844.7, 1668.4, 1592.3, 1483.4, 1441.4, 1349.9, 1308.2, 1276.6, 1206.1, 1170.8, 1052.9, 791.6, 518.7 cm$^{-1}$; MS 346.0 (M+1)$^+$.

Example 40

Figure 2:
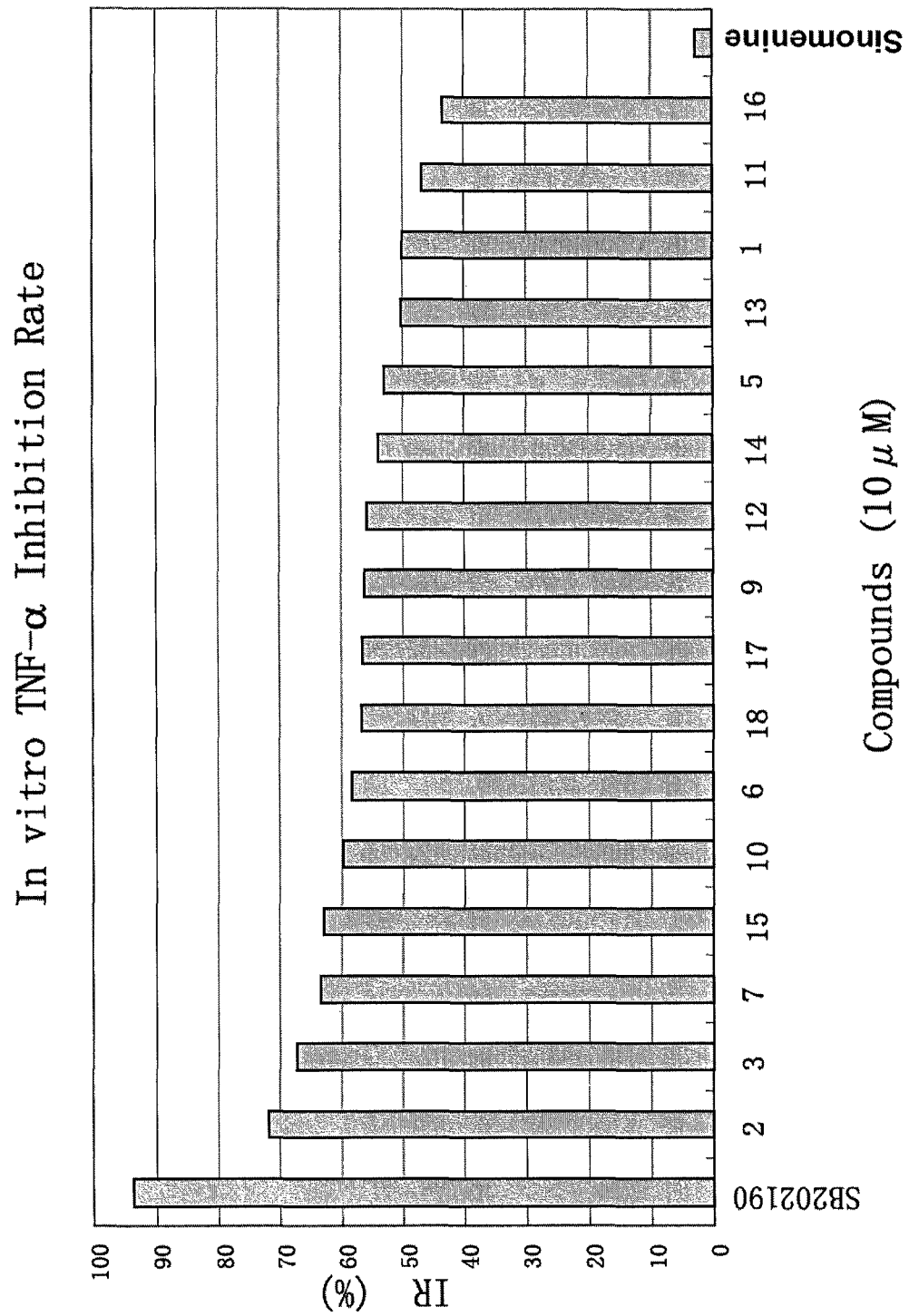
FIG. 2 shows results of anti-inflamatory and immune suppression activities of preferred compounds of the invention based on in vitro TNF-α inhibition assays. The horizontal axis indicates the compound numbers corresponding to the examples, and the vertical axis indicates the inhibition rate (IR) of TNF-α. The concentration used in the assays is 10 μM.

In vitro inhibition of TNF-α: inoculate 48 well plates with mice macrophase cell line J774, at 1×10$^5$ cells/well. Incubate in DMEM containing 10% FBS under 6% $CO_2$ for 12 hours. Use DMEM medium containing 1 μg/mL LPS to dilute the small molecule compounds to a final concentration of 10$^{-5}$ mol/L and use that to replace the original culture medium. The incubation is continued for another 5 hours. Collect the supernatants and determine TNF-α using ELISA. Results are shown in FIG. 1 and FIG. 2. In this experiment, compound SB 202190 (4-(4-fluorophenyl)-2-(4-hydroxyphenyl)-5-(4-pyridyl)-1H-imidazole, CAS 152121-30-7, was purchased from Sigma. This compound is a specific inhibitor of p38 MAPK. Through inhibition of p38 phosphorylation, it inhibits the production of TNF-α) is used as a positive control.

SB202190

Based on the results shown in FIG. 1, most compounds exhibit anti-inflammatory activities, especially Compounds 1, 4, 31, 39, 8, and 40, which show apparent activities. In addition, Compounds 33, 34, and 35 show TNF-α stimulating effects.

Based on results shown in FIG. 2, sinomenine derivatives having a sulfur-containing substituent at position 10 all shown relatively good anti-inflammatory activities.

Example 41

Experiments Using Endotoxin Shock Model

Materials: C57BL/6 mice (6-8 week old) are purchased from Shanghai Laboratory Animal Center (SLAC). Animals are kept, with sufficient water and standard diets, in the Laboratory Animal Center (clean room) in the Institute of Biochemistry and Cell Biology at the Shanghai Institute for Biological Sciences, Chinese Academy of Sciences.

Lipopolysaccharides (LPS) was purchased from Sigma (St. Louis, Mo.) was dissolved in sterile physiological saline and aliquots are stored at −70° C. (The LPS used in the cell testing has a catalog No. L4391, and used in animal testing has a catalog No. L3129.)

Cytokine (TNF-alpha) ELISA test kit (Catalog No. MTA00) was purchased from R&D Co.

Steps: (1) 6-8 week old male C57BL/6 mice are randomly grouped in 5 mice per group for use in endotoxin model tests;

(2) weigh each mouse, and inject peritoneally 200 μL different concentrations of small molecule Compound 1 in physiological saline (the injection doses for the low, medium, and high groups are respectively 25 mg/Kg, 50 mg/Kg, and 100 mg/Kg body weight). The control group was injected with 200 μL physiological saline;

(3) 1 hour after administration of the drug, the animals were injected with 100 μL LPS (injection dose: 2.5 mg/Kg body weight) to induce the inflammation model;

(4) 1.5 hours after the LPS injections, 200 μL blood samples were taken from eye sockets. The blood samples were placed at 4° C. for 12 hours, and then centrifuged at 6,000 rpm for 10 minutes to separate the upper plasma layers;

(5) Use the ELISA test kits to determine the pro-inflammatory cytokine TNF-alpha levels in the plasma samples.

Figure 3:
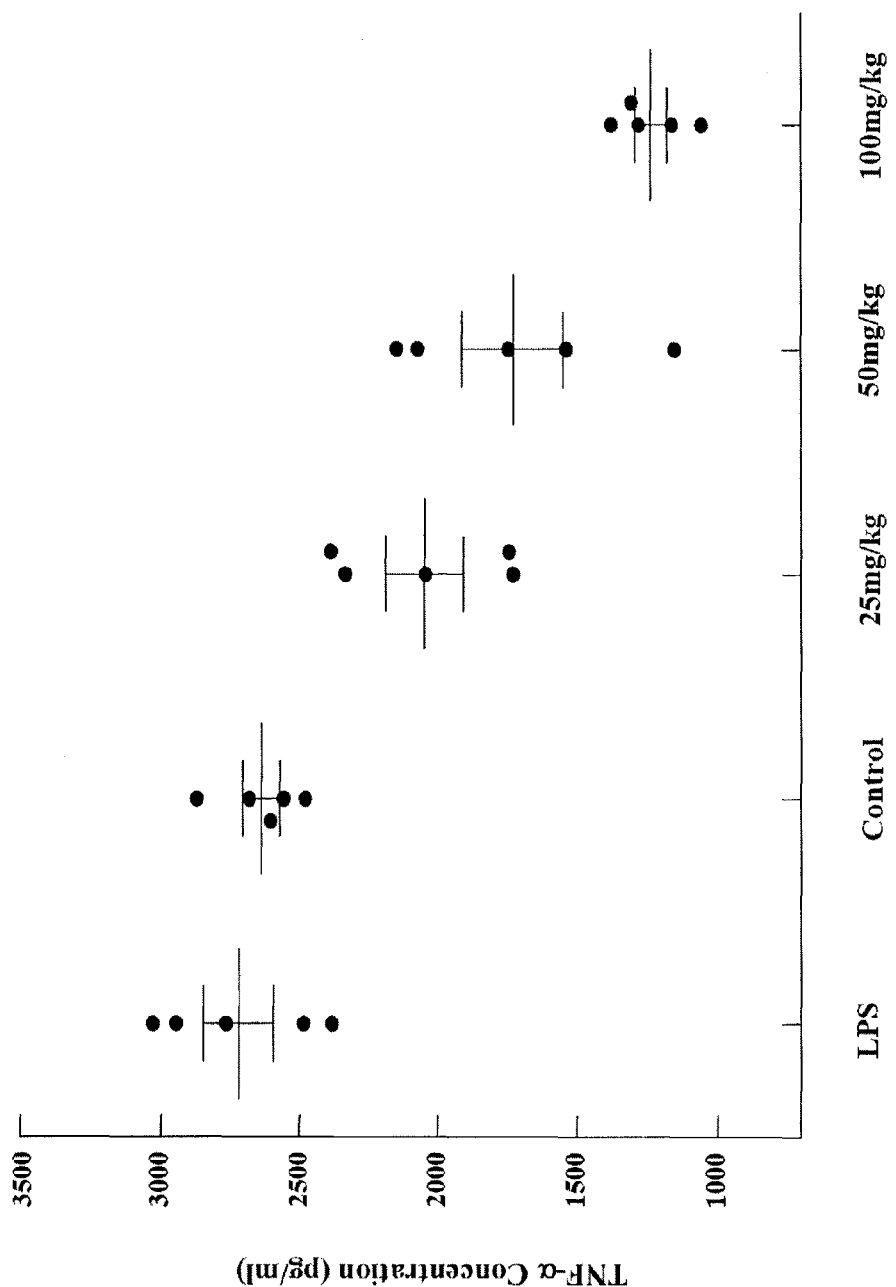
FIG. 3 shows results of anti-inflamatory activity of Compound 1, which is representative of preferred compounds of the invention, verified with an LPS-induced endotoxin shock model. The horizontal axis indicates the compound numbers corresponding to the examples or the amount of Compound 1 used in mg/Kg of mouse body weight. The vertical axis indicates the concentrations of TNF-α.

Based on the results shown in FIG. 3, Compound 1 has a substantial inhibitory effect on the pro-inflammatory cytokine TNF-α. Furthermore, this effect is dose dependent.

All references cited in this application are incorporated by reference as if each of them had been individually cited herein. In addition, it should be appreciated that after reading the content of this description, one skilled in the art in this field would know how to vary and modify the embodiments described herein. These equivalent embodiments are within the scope of the invention as defined in the attached claims.

What is claimed is:

1. A sinomenine derivative, or a pharmaceutically acceptable salt, ester, or solvate thereof, wherein the sinomenine derivative has the following structure:

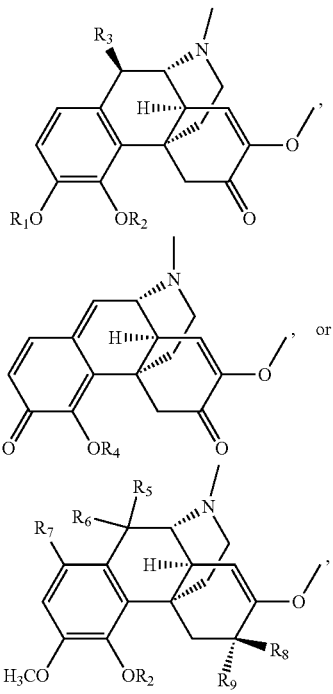

wherein $R_1$=H or $R_{10}$CO; $R_2$=H or $R_{10}$CO; $R_3$=$R_{11}$O, $R_{12}$S, $R_{13}R_{14}$N, OH, $R_{10}$COO, or

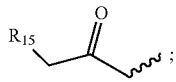

$R_4$=H or $R_{16}R_{17}R_{18}$Si; $R_5$=$R_{11}$O, OH, or $CH_3$COO; $R_6$=H or $R_{11}$O; or $R_5$ and $R_6$ together form an oxo group; $R_7$=H, halogen, or hydroxymethyl; $R_8$=hydroxyl or H; $R_9$=hydroxyl or H; or $R_8$ and $R_9$ together form an oxo group; $R_{10}$=$C_{1-4}$ hydrocarbyl; $R_{11}$=$C_{1-10}$ hydrocarbyl; $R_{12}$=$C_{1-10}$ hydrocarbyl, a 5-membered or 6-membered aromatic ring that is unsubstituted or contains 1-3 substituents, a 5-membered or 6-membered nitrogen-containing heterocycle that is unsubstituted or contains 1-3 substituents, a 5-membered or 6-membered oxygen-containing heterocycle that is unsubstituted or contains 1-3 substituents, or a 5-membered or 6-membered sulfur-containing heterocycle that is unsubstituted or contains 1-3 substituents, wherein the substituent is $C_{1-10}$ hydrocarbyl, halogen, $C_{1-4}$ alkyl, or $C_{1-4}$ fluoroalkyl, nitro, cyano, methoxy, or hydroxyl group; $R_{13}$=$C_{1-10}$ hydrocarbyl, a 5-membered or 6-membered aromatic ring that is unsubstituted or contains 1-3 substituents, a 5-membered or 6-membered nitrogen-containing heterocycle that is unsubstituted or contains 1-3 substituents, a 5-membered or 6-membered oxygen-containing heterocycle that is unsubstituted or contains 1-3 substituents, or a 5-membered or 6-membered sulfur-containing heterocycle that is unsubstituted or contains 1-3 substituents, wherein the substituent is $C_{1-10}$ hydrocarbyl, halogen, $C_{1-4}$ alkyl, or $C_{1-4}$ fluoroalkyl, nitro, cyano, $C_{1-4}$ alkoxy, or hydroxyl group; $R_{14}$H or $C_{1-10}$ hydrocarbyl; or $R_{13}$ and $R_{14}$ together with the N atom, to which they are attached, form a 5-membered or 6-membered nitrogen-containing heterocycle that is unsubstituted or contains 1-3 substituents, wherein the substituent is halogen, $C_{1-4}$ alkyl, or $C_{1-4}$ fluoroalkyl, nitro, cyano, $C_{1-4}$ alkoxy, or hydroxyl group; $R_{15}$=H or $C_{1-10}$ alkyl; $R_{16}$=$C_{1-10}$ hydrocarbyl or phenyl; $R_{17}$=$C_{1-10}$ hydrocarbyl or phenyl; $R_{18}$=$C_{1-10}$ hydrocarbyl or phenyl.

2. The sinomenine derivative, or the pharmaceutically acceptable salt, ester, or solvate thereof accordingly to claim 1, wherein $R_1$=H or $R_{10}$CO; $R_2$=H or $R_{10}$CO; $R_3$=$R_{11}$O, $R_{12}$S, $R_{13}R_{14}$N, OH, $R_{10}$COO, or

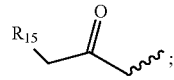

$R_4$=H or $R_{16}R_{17}R_{18}$Si; $R_5$=$R_{11}$O, OH, or $CH_3$COO; $R_6$=H or $R_{11}$O; or $R_5$ and $R_6$ together form an oxo group; $R_7$=H, halogen, or hydroxymethyl; $R_8$=hydroxyl or H; $R_9$=hydroxyl or H; or $R_8$ and $R_9$ together form an oxo group; $R_{10}$=$C_{1-6}$ alkyl; $R_{11}$=$C_{1-6}$ alkyl; $R_{12}$=$C_{1-6}$ alkyl, a phenyl group that is unsubstituted or contains 1-3 substituents, an imidazolyl group that is unsubstituted or contains 1-3 substituents, a furanyl or pyranyl group that is unsubstituted or contains 1-3 substituents, or a thienyl group that is unsubstituted or contains 1-3 substituents, wherein the substituent is halogen, $C_{1-4}$ alkyl, or $C_{1-4}$ fluoroalkyl, nitro, cyano, $C_{1-4}$ alkoxy, or hydroxyl group; $R_{13}$=$C_{1-6}$ alkyl, a phenyl group that is unsubstituted or contains 1-3 substituents, an imidazolyl group that is unsubstituted or contains 1-3 substituents, a furanyl or pyranyl group that is unsubstituted or contains 1-3 substituents, or a thienyl group that is unsubstituted or contains 1-3 substituents, wherein the substituent is halogen, $C_{1-4}$ alkyl, or $C_{1-4}$ fluoroalkyl, nitro, cyano, $C_{1-6}$ alkoxy, or hydroxyl group; $R_{14}$=H or $C_{1-6}$ alkyl; or $R_{13}$ and $R_{14}$, together with the N atom, to which they are attached, form an imidazolyl group that is unsubstituted or contains 1-3 substituents, wherein the substituent is halogen, $C_{1-4}$ alkyl, $C_{1-4}$ fluoroalkyl, nitro, cyano, $C_{1-4}$ alkoxy, or hydroxyl group; $R_{15}$=H or $C_{1-6}$ alkyl; $R_{16}$=$C_{1-6}$ alkyl or phenyl; $R_{17}$=$C_{1-6}$ alkyl or phenyl; $R_{18}$=$C_{1-6}$ alkyl or phenyl.

3. The sinomenine derivative, or the pharmaceutically acceptable salt, ester, or solvate thereof accordingly to claim 1, wherein $R_1$=H or $R_{10}$CO; $R_2$=H or $R_{10}$CO; $R_3$=$R_{11}$O, $R_{12}$S, $R_{13}R_{14}$N, OH, $R_{10}$COO, or

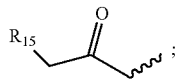

$R_4$=H or $R_{16}R_{17}R_{18}$Si; $R_5$=$R_{11}$O, OH, or $CH_3$COO; $R_6$=H or $R_{11}$O; or $R_5$ and $R_6$ together form an oxo group; $R_7$=H, halogen, or hydroxymethyl; $R_8$=hydroxyl or H; $R_9$=hydroxyl or H; or $R_8$ and $R_9$ together form an oxo group; $R_{10}$=$C_{1-4}$ alkyl; $R_{11}$=$C_{1-4}$ alkyl; $R_{12}$=$C_{1-4}$ alkyl, a phenyl group that is unsubstituted or contains 1-3 substituents, wherein the substituent is halogen, $C_{1-4}$ alkyl, $C_{1-4}$ fluoroalkyl, nitro, cyano, $C_{1-4}$ alkoxy, or hydroxyl group; $R_{13}=C_{1-4}$ alkyl, a phenyl group that is unsubstituted or contains 1-3 substituents, wherein the substituent is halogen, $C_{1-4}$ alkyl, $C_{1-4}$ fluoroalkyl, nitro, cyano, $C_{1-4}$ alkoxy, or hydroxyl group; $R_{14}$=H or $C_{1-6}$ alkyl; or $R_{13}$ and $R_{14}$ together with the N atom, to which they are attached, form an imidazolyl group that is unsubstituted or contains 1-3 substituents, wherein the substituent is halogen, $C_{1-4}$ alkyl, $C_{1-4}$ fluoroalkyl, nitro, cyano, $C_{1-4}$ alkoxy, or hydroxyl group; $R_{15}$=H or $C_{1-4}$ alkyl; $R_{16}=C_{1-4}$ alkyl; $R_{17}=C_{1-4}$ alkyl; $R_{18}=C_{1-4}$ alkyl.

4. The sinomenine derivative, or the pharmaceutically acceptable salt, ester, or solvate thereof accordingly to claim 1, wherein the structure is:

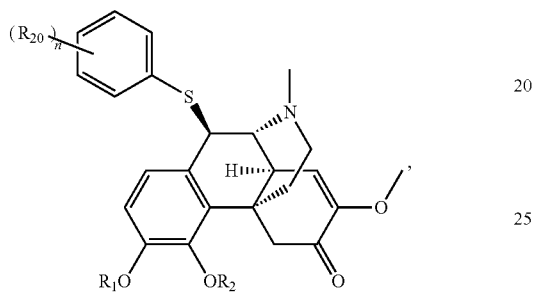

wherein $R^1$=H or $R_{10}$CO; $R_2$=H or $R_{10}$CO, wherein $R_{10}$ is $C_{1-6}$ alkyl, $R_{20}$ represents H or is selected from the following substituents: halogen, $C_{1-4}$ alkyl, $C_{1-4}$ fluoroalkyl, nitro, cyano, $C_{1-4}$ alkoxy, or hydroxyl group; n=1, 2, or 3.

5. The sinomenine derivative, or the pharmaceutically acceptable salt, ester, or solvate thereof accordingly to claim 4, wherein the derivative has the following structure:

1

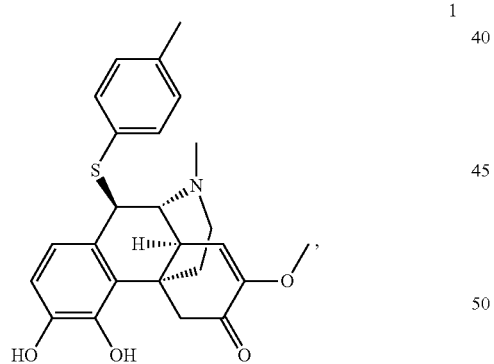

2

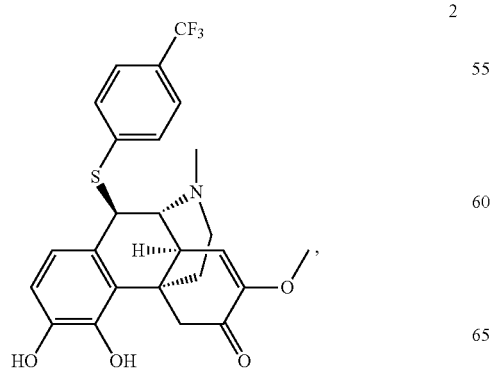

3

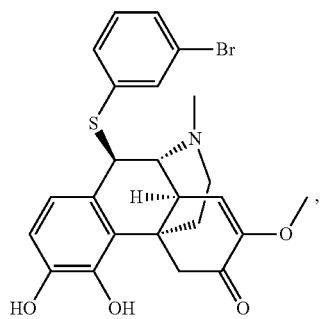

4

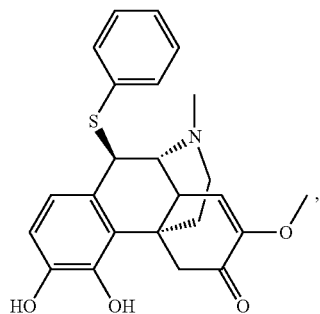

5

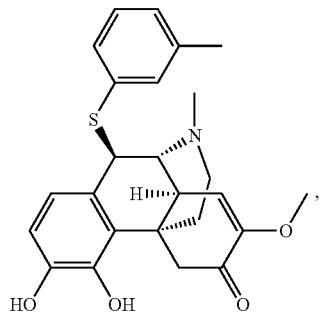

6

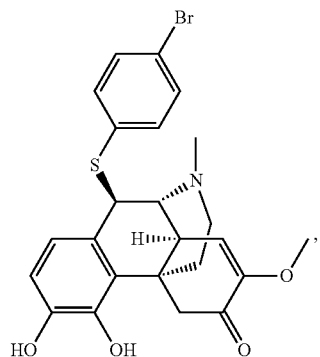

7

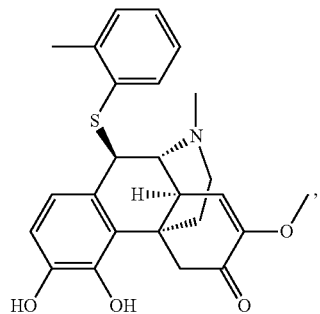

77
-continued
8
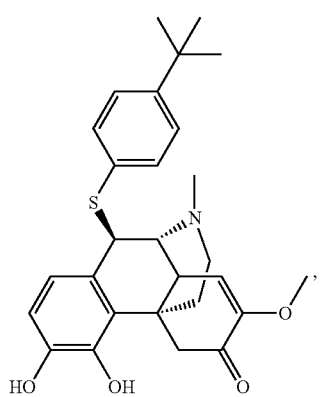
9
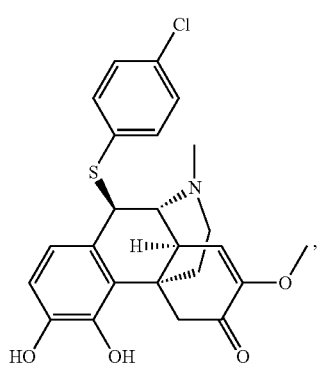
10
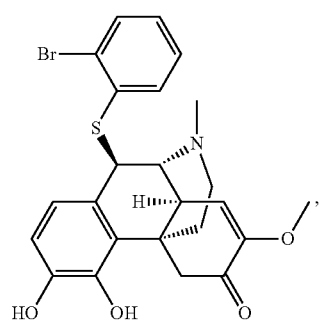
11
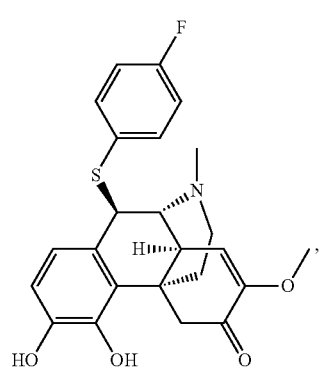
78
-continued
12
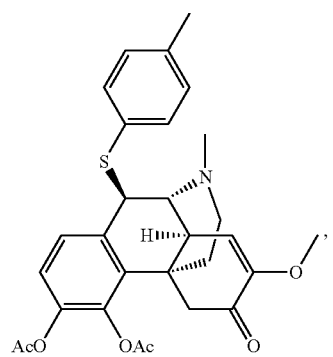
13
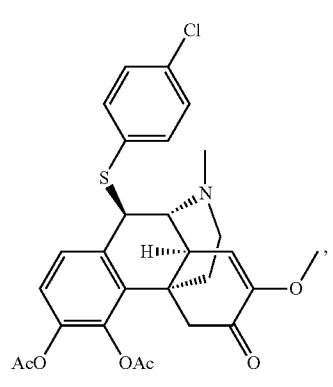
14
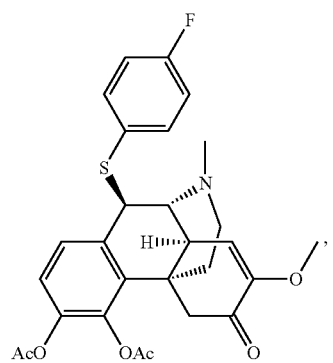
15
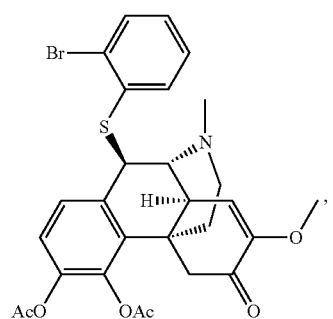

16
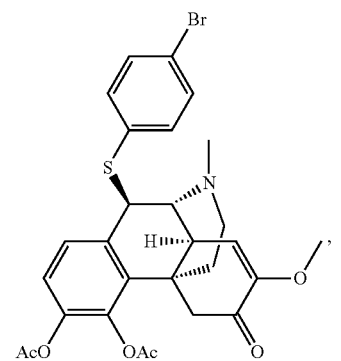
17
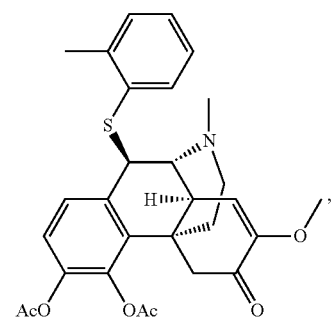
18
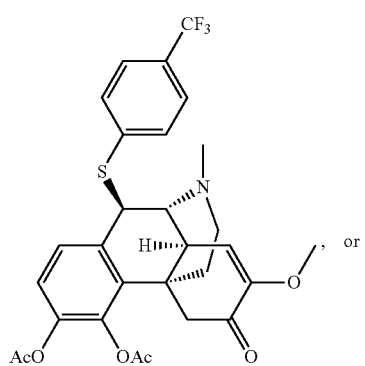
or
19
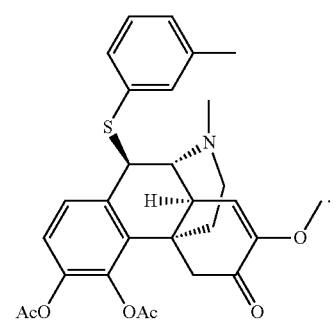
20
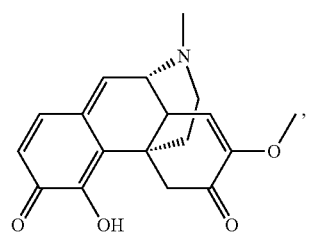
21
22
23
24
25
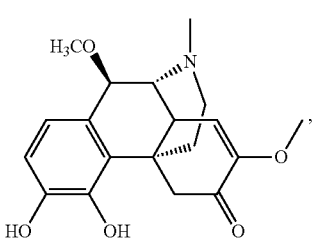
6. The sinomenine derivative, or the pharmaceutically acceptable salt, ester, or solvate thereof accordingly to claim 1, wherein the derivative has the following structure:

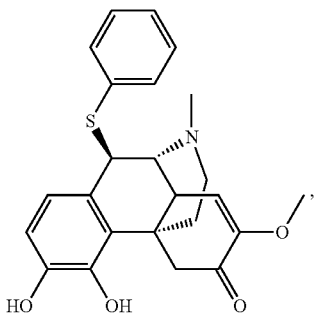
4
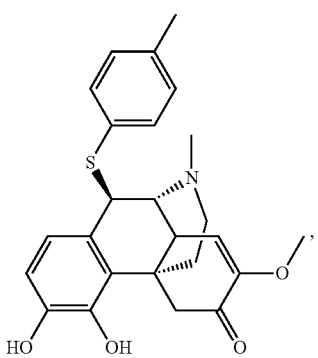
5
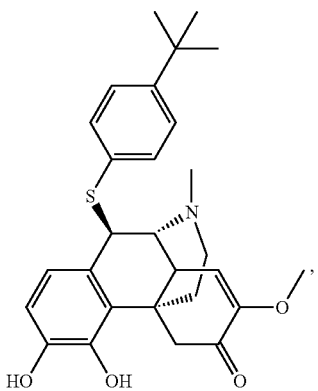
8
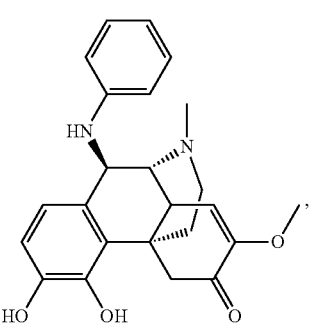
26
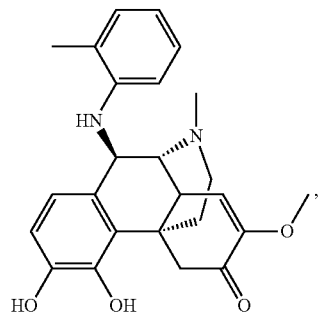
27
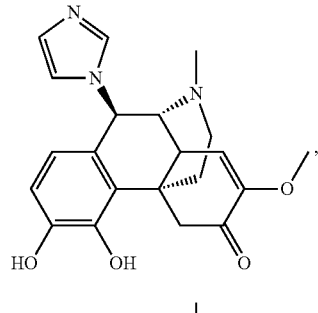
28
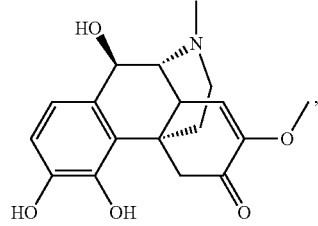
29
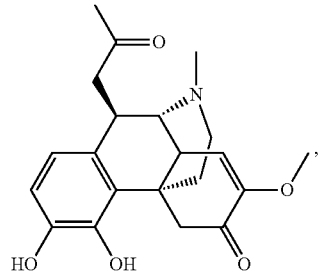
30
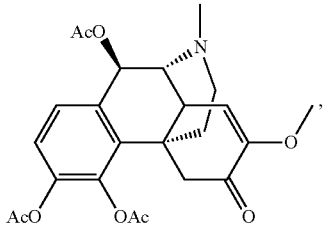
31
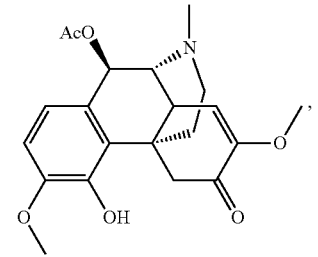
32

33

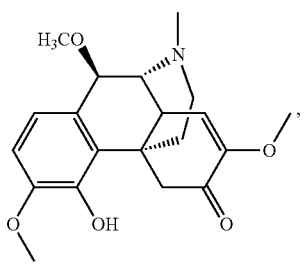

34

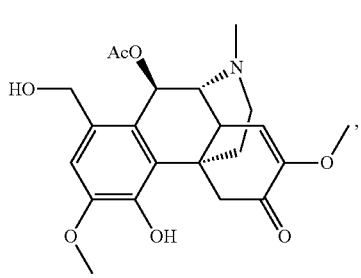

35

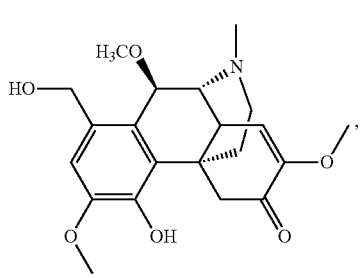

36

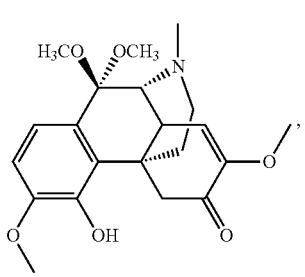

37

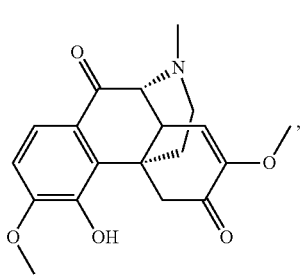

38

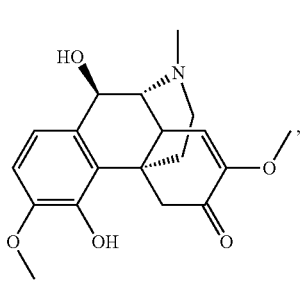

39

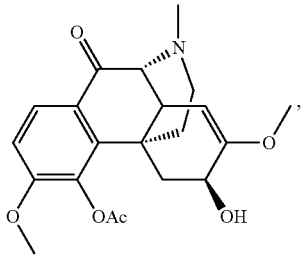

40

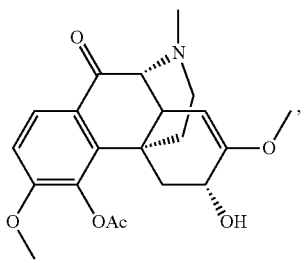

41

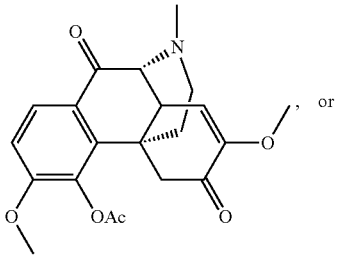, or

42

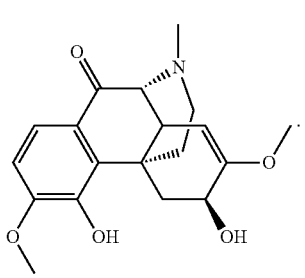

7. The sinomenine derivative, or the pharmaceutically acceptable salt, ester, or solvate thereof accordingly to claim 1, wherein the 5-membered or 6-membered aromatic ring is pentenyl or phenyl, the 5-membered or 6-membered nitrogen-containing heterocycle is pyrrolyl, imidazolyl, pyrazolyl, or pyrimidinyl, the 5-membered or 6-membered oxygen-containing heterocycle is furanyl or pyranyl, the 5-membered or 6-membered sulfur-containing heterocycle is thienyl.

8. A method for synthesizing the sinomenine derivative, or the pharmaceutically acceptable salt, ester, or solvate thereof accordingly to claim 1, the method comprising the following: step (1) alone, or steps (1)-(2), or step (3) alone, or steps (3)-(4), or steps (3) and (5), or step (6) alone, or steps (6)-(7):

(1) reacting sinomenine or a hydrochlorate salt thereof with iodobenzene diacetate in water at room temperature for 0.5-4 hours to produce compound C1, wherein a molar ratio of the sinomenine or the hydrochlorate salt thereof to the iodobenzene diacetate is 1:1-2;

(2) reacting compound C1 with $R_{11}OH$, $R_{12}SH$, $R_{13}R_{14}NH$, $H_2O$

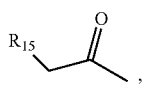

or $(R_{10}CO)_2O$ in an organic solvent for 0.5-48 hours to produce compound C2, or reacting compound C1 with $R_{16}R_{17}R_{18}SiX$ in an organic solvent for 0.5-48 hours to produce compound C3, wherein a molar ratio of compound C1 to $R_{11}OH$, $R_{12}SH$, $R_{13}R_{14}NH$, $H_2O$,

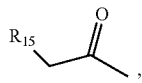

$(R_{10}CO)_2O$, or $R_{16}R_{17}R_{18}SiX$ is 1:1-10;

(3) reacting sinomenine or a derivative thereof with iodobenzene diacetate in methanol at room temperature for 0.5-48 hours to produce compound C4 or compound C5, wherein a molar ratio of the sinomenine or the derivative thereof to the iodobenzene diacetate is 1:1-2, wherein the sinomenine or the derivative has the following structure:

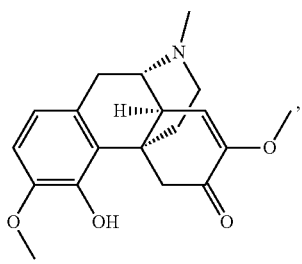

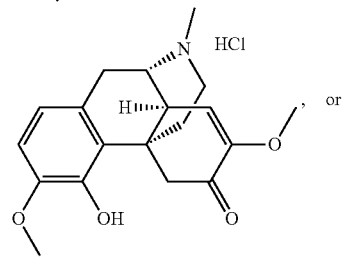

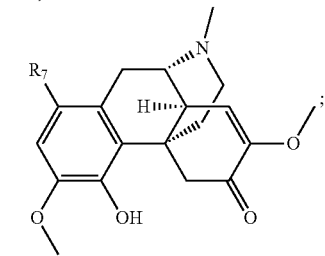

(4) reducing compound C4 in an organic solvent using sodium borohydride, at a temperature from 0° C. to room temperature, for 1-24 hours to produce compound C7, wherein a molar ration of compound C4 to sodium borohydride is 1:1-4; or reacting compound C4 with aluminium trichloride in an organic solvent under reflux for 1-24 hours to produce compound C6, wherein a molar ratio of compound C4 to aluminium trichloride is 1:1-5;

(5) reducing compound C5 in an organic solvent using sodium borohydride, at a temperature from about 0° C. to room temperature, for 1-24 hours to produce compound C8, wherein a molar ration of compound C5 to sodium borohydride is 1:1-4; or hydrolyzing compound C5 with a lithium hydroxide solution, at a temperature from about 0° C. to room temperature, for 0.5-24 hours to produce compound C6, wherein a molar ratio of compound C5 to lithium hydroxide is 1:1-10;

(6) reacting sinomenine or a derivative thereof with an acyl chloride or an acyl anhydride in an organic solvent, at a temperature from about 0° C. to room temperature, for 0.5-24 hours to produce compound C9, wherein a molar ratio of the sinomenine or the derivative thereof to the the acyl chloride or the acyl anhydride is 1:1-4, wherein the sinomenine or the derivative has the following structure:

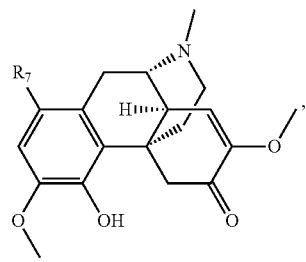

(7) reducing compound C10 in an organic solvent using sodium borohydride, at a temperature from about 0° C. to room temperature, for 1-24 hours to produce compound C11, wherein a molar ration of compound C105 to sodium borohydride is 1:1-4; or hydrolyzing compound C10 with a lithium hydroxide solution, at a temperature from about 0° C. to room temperature, for 0.5-24 hours to produce compound C11, wherein a molar ratio of compound C10 to lithium hydroxide is 1:1-10;

wherein compounds C1-C11 have the following structures:

C1

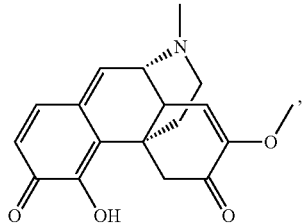

C2

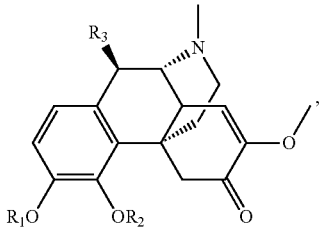

C3

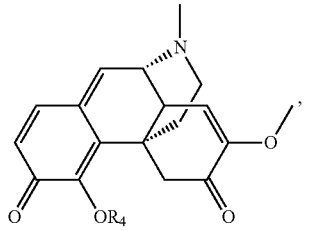

-continued

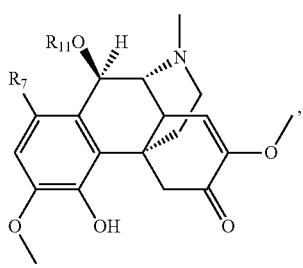

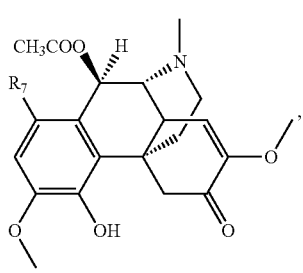

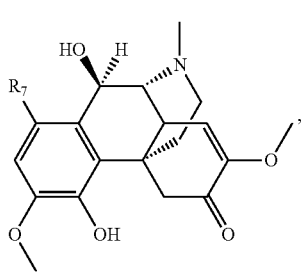

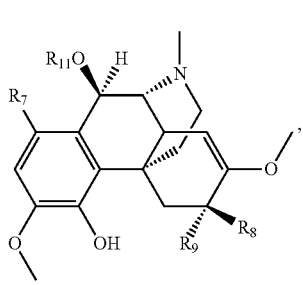

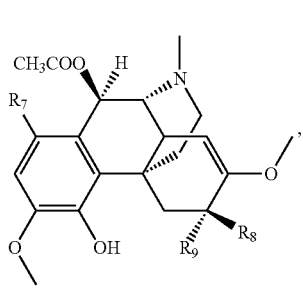

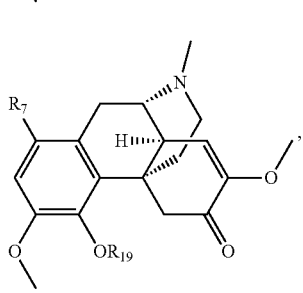

-continued

C4
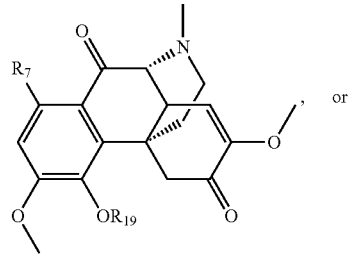

C5
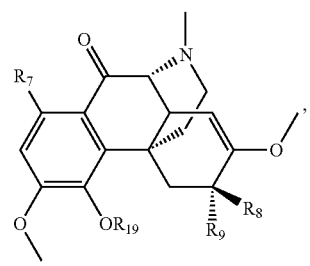

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ are as defined in claim 1; $R_{19}$=H or $R_{10}$CO, wherein X is halogen.

9. The method according to claim 8, wherein compound C1 and $R_{12}$SH are reacted in the organic solvent to produce compound C2, wherein a reaction time is 0.5-48 hours, wherein the molar ratio between compound C1 and $R_{12}$SH is 1:1-10; wherein $R_{12}$ represents

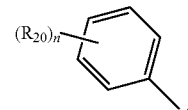

$R_{20}$ represents H or is selected from the following: halogen, $C_{1-4}$ alkyl, $C_{1-4}$ fluoroalkyl, nitro, cyano, $C_{1-4}$ alkoxy or hydroxyl; n=1, 2, or 3; wherein compound C1 has a structure as defined in claim 8, and compound C2 has the following structure:

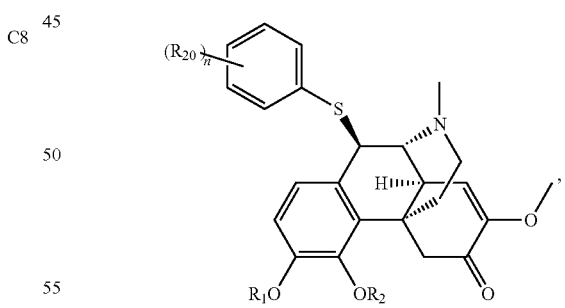

wherein $R_1$=H or $R_{10}$CO; $R_2$=H or $R_{10}$CO; $R_{10}$=$C_{1-6}$ alkyl.

10. The method according to claim 8, wherein
(1) compound C1 and $R_{12}$SH are reacted in an organic solvent to produce compound C2-1, wherein a molar ratio between compound C1 and $R_{12}$SH is 1:1-10;
(2) compound C2-1 is reacted in an organic solvent with an acyl chloride or an acyl anhydride, at a temperature between about 0° C. and room temperature, for 0.5-24 hours to produce compound C2-2, wherein a molar ratio between sinomenine or a derivative thereof and the acyl chloride or the acyl anhydride is 1:1-5, wherein compounds C1, C2-1, and C2-2 have the following structures:

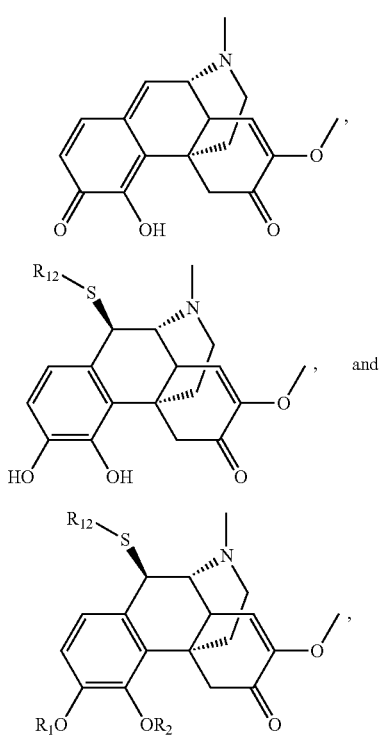

wherein $R_1$ represents $R_{10}CO$, $R_2$ is $R_{10}CO$; $R_{12}$ is

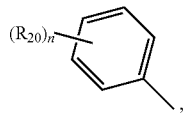

$R_{20}$ is H selected from the following: halogen, $C_{1-4}$ alkyl, $C_{1-4}$ fluoroalkyl, nitro, cyano, $C_{1-4}$ alkoxy or hydroxyl; n=1, 2, or 3; $R_{10}$=$C_{1-6}$ alkyl.

11. The method according to claim 8, wherein the organic solvent is methanol, ethanol, n-propanol, n-butanol, isopropanol, dichloromethane, chloroform, 1,2-dichloroethane, carbon tetrachloride, ether, tetrahydrofuran, benzene, toluene, xylene, acetone, butanone, acetonitrile, N,N-dimethylformamide, or dimethylsulfoxide.

12. A pharmaceutical composition comprising an effective amount of the sinomenine derivative, or pharmaceutically acceptable salt, ester, or solvate thereof accordingly to claim 1 and a pharmaceutically acceptable carrier, excipient, or diluent.

13. The pharmaceutical composition of claim 12, further comprising a therapeutic agent for an immune disease.

14. The pharmaceutical composition of claim 13, wherein the therapeutic agent for the immune disease is selected from a non-steroid anti-inflammatory agent, a glucocorticoid, and an immune suppressant.

15. A method for treating an immune disease, comprising administering to a subject suffering from said immune disease, the sinomenine derivative according to claim 1, wherein said immune disease is selected from inflammatory bowel disease, inflammation, rheumatoid arthritis, juvenile rheumatoid arthritis, psoriatic arthritic, osteoarthritis, refractory rheumatoid arthritis, chronic rheumatoid arthritis, Crohn's disease, or asthma.

16. A method for treating a disease associated with abnormal TNF-α activity in a mammal, comprising administering to a mammal suffering from said disease associated with abnormal TNF-α activity, the sinomenine derivative according to claim 1, wherein said disease associated with abnormal TNF-α activity is selected from inflammatory bowel disease, inflammation, rheumatoid arthritis, juvenile rheumatoid arthritis, psoriatic arthritic, osteoarthritis, refractory rheumatoid arthritis, chronic rheumatoid arthritis, Crohn's disease, or asthma.

* * * * *